US008329703B2

(12) United States Patent
Hu et al.

(10) Patent No.: US 8,329,703 B2
(45) Date of Patent: *Dec. 11, 2012

(54) PYRAZOLE COMPOUNDS

(75) Inventors: Youhong Hu, Ridgewood, NJ (US); Bin Xu, Wesley Hills, NY (US); Yun Liao, Glen Rock, NJ (US); Kenneth Nawoschik, Spring Valley, NY (US); Yixin Liu, Paramus, NJ (US); Anthony Sandrasagra, Princeton, NJ (US); Reza Fathi, Hohokus, NJ (US); Zhen Yang, Ridgewood, NJ (US)

(73) Assignee: XTL Biopharmaceuticals Ltd., Rehovot (IL)

(*) Notice: Subject to any disclaimer, the term of this patent is extended or adjusted under 35 U.S.C. 154(b) by 403 days.

This patent is subject to a terminal disclaimer.

(21) Appl. No.: 11/058,852

(22) Filed: Feb. 15, 2005

(65) Prior Publication Data
US 2006/0183751 A1    Aug. 17, 2006

(51) Int. Cl.
  *A61K 31/496* (2006.01)
  *A61K 31/454* (2006.01)
  *A61K 31/416* (2006.01)
(52) U.S. Cl. .................. 514/254.05; 514/326; 514/406; 544/371; 546/211; 548/364.1; 548/379.1
(58) Field of Classification Search .......................... None
See application file for complete search history.

(56) References Cited

U.S. PATENT DOCUMENTS

| | | | |
|---|---|---|---|
| 5,091,386 A | 2/1992 | Kesseler et al. | |
| 5,300,521 A | 4/1994 | Eberle et al. | |
| 6,916,839 B2 | 7/2005 | Ebenbeck et al. | |
| 7,238,722 B2 | 7/2007 | Ebenbeck et al. | |
| 2002/0156115 A1 | 10/2002 | Oda et al. | |
| 2002/0183366 A1 | 12/2002 | Garvey et al. | |
| 2003/0191171 A1 | 10/2003 | Oda et al. | |
| 2006/0030559 A1 | 2/2006 | Buettelmann et al. | |
| 2009/0041723 A1* | 2/2009 | Li et al. ........................ | 424/85.7 |

FOREIGN PATENT DOCUMENTS

| | | |
|---|---|---|
| AU | 2003266548 A1 | 4/2004 |
| EP | 1 219 173 | 7/2002 |
| JP | 2004359619 A | 12/2004 |
| WO | WO 01/20993 A1 | 3/2001 |
| WO | WO 02/051810 A2 | 7/2002 |
| WO | WO 2004/026839 A1 | 1/2004 |
| WO | WO 2005/033100 A1 | 4/2005 |
| WO | WO 2006/028524 A2 | 3/2006 |

OTHER PUBLICATIONS

Stoermer et al., caplus an 1907:8801.*
http://www.apath.com/Directory/Licensing/Technology/HCV_Replicon.asp.*
http://www.mayoclinic.com/health/hepatitis-c/DS00097/DSECTION=8.*
Chawla et al., "Challenges in Polymorphism of Pharmaceuticals", CRIPS vol. 5, No. 1, Jan.-Mar. 2004 (4 Pages).*
Newman et al., "Solid-state analysis of the active pharmaceutical ingredient in drug products", DDT vol. 8, No. 19, Oct. 2003, p. 898-905.*
Reimlinger et al., caplus an 1969:96697.*
Gough et al., caplus an 1933:35749.*
Chen et al., Bioorg. Med. Chem. Lett. 19 (2009) 1105-1109.*
HCV, HepatitisC, 2012, http://en.wikipedia.org/wiki/Hepatitis_C.*
HCV-Replicon, 2012, http://www.southernresearch.org/life-sciences/infectious-diseases/virology/hepatitis/vitro-evaluations.*
Ford et al., caplus 1973:84481.*
Replicon, http://www.apath.com/Directory/Licensing/Technology/HCVReplicon.asp (2007).*
Hepatitis, http://www.mayoclinic.comlhealthlhepatitis-cIDS000971DSECTION=8 (2007).*
International Search Report issued Feb. 12, 2007 in PCT/US2006/005236.

* cited by examiner

*Primary Examiner* — Sun Jae Loewe
(74) *Attorney, Agent, or Firm* — Fenwick & West LLP

(57) ABSTRACT

Aryl substituted pyrazole derivatives are provided, as well as processes for their preparation. The invention also provides compositions and methods for the treatment of HCV by administering a compound of the present invention, alone or in combination with additional antiviral agents, in a therapeutically effective amount.

20 Claims, No Drawings

PYRAZOLE COMPOUNDS

BACKGROUND OF THE INVENTION

Strategies in new drug discovery often look to natural products for leads in finding new chemical compounds with therapeutic properties. One of the recurring problems in drug discovery is the availability of organic compounds derived from natural sources. Techniques employing combinatorial chemistry attempt to overcome this problem by allowing the high throughput synthesis and testing of hundreds or thousands of related synthetic compounds, called a chemical library. In designing the synthesis of a prospective therapeutic compound or a chemical library, one often looks to natural chemical motifs which are known to have broad biological activity.

Pyrazole has a long history of application in pharmaceutical and agrochemical industry, and posses a widespread occurrence as sub-structures in a large variety of compounds, which exhibit important biological activities and pharmacological properties. Elguero, J. *In Comprehensive Heterocyclic Chemistry II*; Katritzky, A. R.; Rees, C. W.; Scriven, E. F. V.; Pergamon-Elsevier Science: Oxiford, 1996; Vol. 6, pp. 1-75; (b) Sutharchanadevi, M.; Murugan, R. *In Comprehensive Heterocyclic Chemistry II*; Katritzky, A. R.; Rees, C. W.; Scriven, E. F. V.; Pergamon-Elsevier Science: Oxiford, 1996; Vol. 6, pp. 221-260.

Infection with the Hepatitis C virus (HCV) represents a serious world-wide health crisis. In more than 70% of infected individuals, the virus evades clearance by the immune system leading to a persistent HCV infection. The long term effects of persistent HCV infection range from an apparently healthy carrier state to chronic hepatitis, liver fibrosis, cirrhosis, and eventually hepatocellular carcinoma. HCV is a leading cause of chronic liver disease. The best therapy currently available for treatment of HCV infection uses a combination of pegylated α-interferon and ribavirin. However, many of the patients treated with this therapy fail to show a sufficient antiviral response. Additionally, interferon treatment also induces severe side-effects (i.e. retinopathy, thyroiditis, acute pancreatitis, depression) that diminish the quality of life of treated patients. Thus, it is vital that more effective treatments be identified.

SUMMARY OF THE INVENTION

The present invention provides pyrazole derivatives of the formula I:

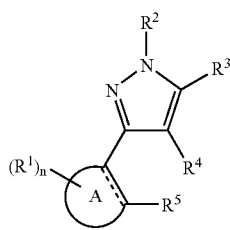

(I)

wherein:
ring A is selected from a 5- or 6-membered aromatic rings which may optionally contain 0 to 3 ring heteroatoms;
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2$$R^{11}$, —SR$^{11}$, —C(O)$R^{11}$, —C(O)OR$^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SOR$^{11}$, —SO$_3$R$^{11}$, —SO$_2$N($R^{12}$)($R^{13}$), -alkyl-O—R$^{11}$, cycloalkyl, cycloalkenyl, halo, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;
$R^2$ is selected from H, alkyl, cycloalkyl, cycloalkenyl, alkenyl, alkynyl, aralkyl, aryl, heteroaryl, —C(O)$R^{21}$, —C(O)OR$^{21}$, -alkyl-O-alkyl, -alkyl-O-aryl;
$R^{21}$ is selected from H, alkyl, alkyl-O-alkyl, alkyl-O-aryl, alkenyl, alkynyl, cycloalkyl, cycloalkenyl, aralkyl, aryl and heteroaryl;
$R^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)$R^{31}$, —C(O)OR$^{31}$, —C(O)N($R^{32}$)($R^{33}$);
$R^{31}$ is selected from H, alkyl, alkyl-O-alkyl, alkyl-O-aryl, alkenyl, alkynyl, cycloalkyl, cycloalkenyl, aralkyl, aryl and heteroaryl;
$R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, NO$_2$, CO$_2$R$^{34}$, C(O)R$^{34}$—O—R$^{34}$, —N(R$^{34}$)(R$^{35}$), —N(R$^{34}$)C(O)R$^{34}$—N(R$^{34}$)SO$_2$R$^{34}$, —SR$^{34}$, —C(O)N(R$^{35}$)(R$^{36}$), —OC(O)R$^{34}$, —OC(O)N(R$^{35}$)(R$^{36}$), SO$_2$, —SOR$^{34}$, —SO$_3$R$^{34}$, —SO$_2$N(R$^{35}$)(R$^{36}$), halo, cycloalkyl, cycloalkenyl, aryl and heteroaryl;
each $R^{34}$ is independently selected from H, alkyl, cycloalkyl, cycloalkeneyl, alkenyl, alkynyl, aralkyl, aryl and heteroaryl;
each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;
$R^4$ is selected from H, alkyl, -alkyl-O-alkyl, cycloalkyl, aralkyl, aryl, heteroaryl,

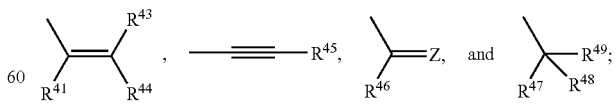

wherein
Z is selected from O, N—OR$^{461}$;
$R^{461}$ is selected from H, alkyl, alkenyl, aralkyl, cycloalkyl, cycloalkenyl, -alkyl-O-alkyl, alkyl-O-aryl and —(CH$_2$)$_a$—R$^{42}$;

$R^{41}$, $R^{43}$, $R^{44}$, $R^{46}$, $R^{47}$, $R^{48}$ and $R^{49}$ are independently selected from H, alkyl, alkenyl, alkynyl, aralkyl, cycloalkyl, cycloalkenyl, -alkyl-O-alkyl, -alkyl-O-aryl, and —(CH$_2$)$_a$—R$^{42}$;

$R^{45}$ is selected from H, alkyl, -alkyl-O-alkyl, -alkyl-O-aryl, aryl, aralkyl, cycloalkyl, cycloalkenyl, and —(CH$_2$)$_a$—R$^{42}$;

$R^{42}$ is selected from —N(R$^{421}$)C(O)R$^{421}$, —N(R$^{421}$)SO$_2$R$^{421}$, —OR$^{421}$, —SR$^{421}$, —C(O)R$^{421}$, —C(O)OR$^{421}$, —C(O)N(R$^{422}$)(R$^{423}$), —OC(O)R$^{421}$, —C(O)N(R$^{422}$)(R$^{423}$), CN, CF$_3$, NO$_2$, SO$_2$, —SOR$^{421}$, —SO$_3$R$^{421}$, —SO$_2$N(R$^{422}$)(R$^{423}$), -alkyl-O-alkyl, -alkyl-O-aryl, halo, cycloalkyl, cycloalkenyl, aryl and heteroaryl;

or $R^{42}$ is selected from a group having the formula

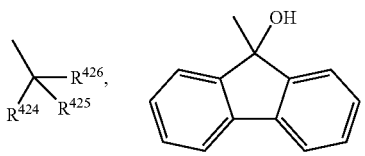

each $R^{421}$ is independently selected from H, alkyl, cycloalkyl, alkenyl, alkynyl, aralkyl, aryl and heteroaryl;

each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;

each $R^{424}$ is independently selected from H, OH, alkyl, cycloalkyl, alkenyl, alkynyl, aralkyl, aryl and heteroaryl;

each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to which they are attached form a 5- to 7-membered ring which may optionally contain a further heteroatom;

a is 1 to 6;

$R^5$ is selected from H, OR$^{51}$, —SR$^{51}$, alkyl, cycloalkyl, cycloalkenyl, alkenyl, alkynyl, CN, CF$_3$, NO$_2$, SO$_2$, —SOR$^{51}$, —SO$_3$R$^{51}$, —SO$_2$N(R$^{52}$)(R$^{53}$), -alkyl-O-alkyl, halo, aralkyl, aryl, heteroaryl, —C(O)R$^{51}$, —C(O)OR$^{51}$, —C(O)N(R$^{52}$)(R$^{53}$), —OC(O)R$^{51}$, —OC(O)N(R$^{52}$)(R$^{53}$), —O(CH$_2$)$_e$C(O)OR$^{51}$, —O(CH$_2$)$_e$C(O)N(R$^{52}$)(R$^{53}$), —N(R$^{52}$)(R$^{53}$), —N(R$^{51}$)C(O)R$^{51}$, and —N(R$^{51}$)SO$_2$R$^{51}$;

each $R^{51}$ is independently selected from H, alkyl, cycloalkyl, cycloalkenyl, alkenyl, alkynyl, aralkyl, aryl and heteroaryl;

$R^{52}$ and $R^{53}$ are independently selected from H, alkyl, cycloalkyl, cycloalkenyl, alkenyl, alkynyl, aralkyl, aryl and heteroaryl;

or $R^{52}$ and $R^{53}$ may be taken together with the nitrogen to which they are attached form a 5- to 7-membered ring which may optionally contain a further heteroatom;

e is 1 to 6;

alternatively, —O—R$^{51}$ is combined with R$^{41}$, R$^{46}$, or R$^{47}$ to give a 6-membered ring that is fused to ring A and to the pyrazole ring;

or $R^5$ is selected from a group having the formula:

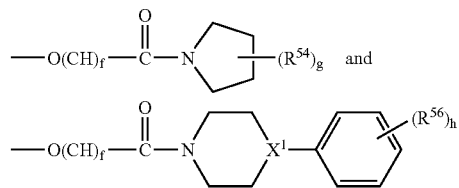

wherein each $R^{54}$ and $R^{56}$ is independently selected from —OR$^{57}$, halo, alkyl, cycloalkyl, cycloalkenyl, alkenyl, alkynyl, NO$_2$, CN, —C(O)R$^{57}$, —C(O)OR$^{57}$, —C(O)N(R$^{58}$)(R$^{59}$), —OC(O)R$^{57}$, —OC(O)N(R$^{58}$)(R$^{59}$), O(CH$_2$)$_i$C(O)OR$^{57}$, —O(CH$_2$)$_i$C(O)N(R$^{58}$)(R$^{59}$), —N(R$^{58}$)(R$^{59}$), —N(R$^{57}$)C(O)R$^{57}$, —N(R$^{57}$)SO$_2$R$^{57}$, aralkyl, aryl and heteroaryl;

each $R^{57}$ is independently selected from H, alkyl, cycloalkyl, cycloalkenyl, alkenyl, alkynyl, aralkyl, aryl and heteroaryl;

$R^{58}$ and $R^{59}$ are independently selected from H, alkyl, cycloalkyl, cycloalkenyl, alkenyl, alkynyl, aralkyl, aryl and heteroaryl; or $R^{52}$ and $R^{53}$ may be taken together with the nitrogen to which they are attached form a 5- to 7-membered ring which may optionally contain a further heteroatom;

i is 1 to 6;

$X^1$ is selected from N and CH;

f is 1 to 6;

g is 0 to 4; and h if 0 to 5;

or a pharmaceutically acceptable salt or hydrate thereof.

In a preferred embodiment, the invention provides a compound having the formula V:

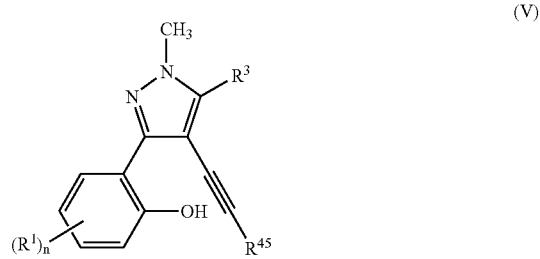

wherein:

each $R^1$ is independently selected from alkyl, alkenyl, alkynyl, aralkyl, —O—R$^{11}$, —N(R$^{12}$)(R$^{13}$), —N(R$^{11}$)C(O)R$^{11}$, —N(R$^{11}$)SO$_2$R$^{11}$, —SR$^{11}$, —C(O)R$^{11}$, —C(O)OR$^{11}$, —C(O)N(R$^{12}$)(R$^{13}$), —OC(O)R$^{11}$, —OC(O)N(R$^{12}$)(R$^{13}$), CN, CF$_3$, NO$_2$, SO$_2$, —SOR$^{11}$, —SO$_3$R$^{11}$, —SO$_2$N(R$^{12}$)(R$^{13}$), -alkyl-O—R$^{11}$, cycloalkyl, cycloalkenyl, halo, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

$R^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)$R^{31}$, —C(O)O$R^{31}$, —C(O)N($R^{32}$)($R^{33}$);

$R^{31}$ is selected from H, alkyl, alkyl-O-alkyl, alkyl-O-aryl, alkenyl, alkynyl, cycloalkyl, cycloalkenyl, aralkyl, aryl and heteroaryl;

$R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, NO$_2$, CO$_2$$R^{34}$, C(O)$R^{34}$, —O—$R^{34}$, —N($R^{34}$)($R^{35}$), —N($R^{34}$)C(O)$R^{34}$—N($R^{34}$)SO$_2$$R^{34}$—S$R^{34}$, —C(O)N($R^{35}$)($R^{36}$), —OC(O)$R^{34}$, —OC(O)N($R^{35}$)($R^{36}$), SO$_2$, —SO$R^{34}$, —SO$_3$$R^{34}$, —SO$_2$N($R^{35}$)($R^{36}$), halo, cycloalkyl, cycloalkenyl, aryl and heteroaryl;

each $R^{34}$ is independently selected from H, alkyl, cycloalkyl, cycloalkeneyl, alkenyl, alkynyl, aralkyl, aryl and heteroaryl; each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;

$R^{45}$ is selected from H, alkyl, -alkyl-O-alkyl, -alkyl-O-aryl, aryl, aralkyl, cycloalkyl, cycloalkenyl, and —(CH$_2$)$_a$—$R^{42}$;

$R^{42}$ is selected from —N($R^{421}$)C(O)$R^{421}$, —N($R^{421}$)SO$_2$$R^{421}$, —O$R^{421}$, —S$R^{421}$, —C(O)$R^{421}$, —C(O)O$R^{421}$, —C(O)N($R^{422}$)($R^{423}$), —OC(O)$R^{421}$, —OC(O)N($R^{422}$)($R^{423}$), CN, CF$_3$, NO$_2$, SO$_2$, —SO$R^{421}$, —SO$_3$$R^{421}$, —SO$_2$N($R^{422}$)($R^{423}$), -alkyl-O-alkyl, -alkyl-O-aryl, halo, cycloalkyl, cycloalkenyl, aryl and heteroaryl;

or $R^{42}$ is selected from a group having the formula

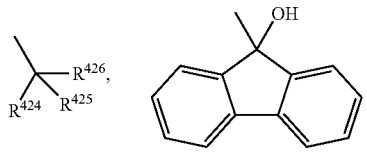

each $R^{421}$ is independently selected from H, alkyl, cycloalkyl, alkenyl, alkynyl, aralkyl, aryl and heteroaryl;

each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;

each $R^{424}$ is independently selected from H, OH, alkyl, cycloalkyl, alkenyl, alkynyl, aralkyl, aryl and heteroaryl;

each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to which they are attached form a 5- to 7-membered ring which may optionally contain a further heteroatom;

a is 1 to 6;

or a pharmaceutically acceptable salt or hydrate thereof.

The invention also provides a synthetic process for the preparation of compounds of the invention. The process uses mild reaction conditions, which provides a high substituent tolerance. Thus, the process is applicable to the preparation of a wide variety of pyrazole derivatives with diverse substitution patterns. Additionally, the process is appropriate for use with combinatorial synthesis techniques. Thus, the process provides a method for producing a library of pyrazole derivatives for biological screening.

The invention also provides compositions and methods for the treatment of HCV by administering a compound of the present invention in a therapeutically effective amount.

DETAILED DESCRIPTION OF THE INVENTION

The term "halo" or "halogen" as used herein includes fluorine, chlorine, bromine and iodine.

The term "alkyl" as used herein contemplates both straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl, and the like. Additionally, the alkyl group may be optionally substituted with one or more substituents selected from halo, CN, NO$_2$, CO$_2$R, C(O)R, —O—R, —N(R')(R"), —N(R)C(O)R, —N(R)SO$_2$R, —SR, —C(O)N(R')(R"), —OC(O)R, —OC(O)N(R')(R"), SO$_2$, —SOR, —SO$_3$R, —SO$_2$N(R')(R"), halo, cycloalkyl, cycloalkenyl, aryl and heteroaryl.

The term "alkenyl" as used herein contemplates both straight and branched chain alkene radicals containing from two to 8 carbon atoms. Additionally, the alkenyl group may be optionally substituted with one or more substituents selected from halo, CN, NO$_2$, CO$_2$R, C(O)R, —O—R, —N(R')(R"), —N(R)C(O)R, —N(R)SO$_2$R, —SR, —C(O)N(R')(R"), —OC(O)R, —OC(O)N(R')(R"), SO$_2$, —SOR, —SO$_3$R, —SO$_2$N(R')(R"), halo, cycloalkyl, cycloalkenyl, aryl and heteroaryl.

The term "alkynyl" as used herein contemplates both straight and branched carbon chain containing from two to 8 carbon atoms and having at least one carbon-carbon triple bond. The term alkynyl includes, for example ethynyl, 1-propynyl, 2-propynyl, 1-butynyl, 3-methyl-1-butynyl, and the like. Additionally, the alkynyl group may be optionally substituted with one or more substituents selected from halo, CN, NO$_2$, CO$_2$R, C(O)R, —O—R, —N(R')(R"), —N(R)C(O)R, —N(R)SO$_2$R, —SR, —C(O)N(R')(R"), —OC(O)R, —OC(O)N(R')(R"), SO$_2$, —SOR, —SO$_3$R, —SO$_2$N(R')(R"), halo, cycloalkyl, cycloalkenyl, aryl and heteroaryl.

The term "cycloalkyl" as used herein contemplates cyclic alkyl radicals containing form 3 to 7 carbon atoms and includes cyclopropyl, cyclopentyl, cyclohexyl, and the like. Additionally, the cycloalkyl group may be optionally substituted with one or more substituents selected from halo, CN, NO$_2$, CO$_2$R, C(O)R, —O—R, —N(R')(R"), —N(R)C(O)R, —N(R)SO$_2$R, —SR, —C(O)N(R')(R"), —OC(O)R, —OC(O)N(R')(R"), SO$_2$, —SOR, —SO$_3$R, —SO$_2$N(R')(R"), halo, alkyl, cycloalkenyl, aryl and heteroaryl.

The term "cycloalkenyl" as used herein contemplates cyclic alkenyl radicals containing form 5 to 7 carbon atoms in which has a double bond between two of the ring carbons and includes cyclopentenyl, cyclohexenyl, and the like. Additionally, the cycloalkenyl group may be optionally substituted with one or more substituents selected from halo, CN, NO$_2$, CO$_2$R, C(O)R, —O—R, —N(R')(R"), —N(R)C(O)R, —N(R)SO$_2$R, —SR, —C(O)N(R')(R"), —OC(O)R, —OC(O)N(R')(R"), SO$_2$, —SOR, —SO$_3$R, —SO$_2$N(R')(R"), halo, alkyl, cycloalkenyl, aryl and heteroaryl.

The term "aralkyl" as used herein contemplates a lower alkyl group which has as a substituent an aromatic group. Additionally, the aralkyl group may be optionally substituted with one or more substituents selected from halo, CN, NO$_2$, CO$_2$R, C(O)R, —O—R, —N(R')(R"), —N(R)C(O)R, —N(R)SO$_2$R, —SR, —C(O)N(R')(R"), —OC(O)R, —OC(O)N(R')(R"), SO$_2$, —SOR, —SO$_3$R, —SO$_2$N(R')(R"), halo, cycloalkyl, cycloalkenyl, aryl and heteroaryl.

The term "heterocyclic group" or "heterocyclic ring" as used herein contemplates aromatic and non-aromatic cyclic radicals having at least one heteroatom as a ring member. Preferred heterocyclic groups are those containing 5 or 6 ring atoms which includes at least one hetero atom, and includes cyclic amines such as morpholino, piperidino, pyrrolidino, and the like, and cyclic ethers, such as tetrahydrofuran, tetrahydropyran, and the like. Aromatic heterocyclic groups, also termed "heteroaryl" groups contemplates single-ring hetero-aromatic groups that may include from one to three heteroatoms, for example, pyrrole, furan, thiophene, imidazole, oxazole, thiazole, triazole, pyrazole, pyridine, pyrazine, pyridazine, pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, tetrahydroisoquinoline, quinoxaline, quinaxoline, benzimidazole, benzofuran, purine, imidazopyridine, benzotriazole, and the like. Additionally, the heterocyclic group may be optionally substituted with one or more substituents selected from halo, alkyl, CN, NO$_2$, CO$_2$R, C(O)R, —O—R, —N(R')(R"), —N(R)C(O)R, —N(R)SO$_2$R, —SR, —C(O)N(R')(R"), —OC(O)R, —OC(O)N(R')(R"), SO$_2$, —SOR, —SO$_3$R, —SO$_2$N(R')(R"), halo, cycloalkyl, cycloalkenyl, aryl and heteroaryl.

The terms "aryl", "aromatic group", or "aromatic ring" as used herein contemplates single-ring aromatic groups (for example, phenyl, pyridyl, pyrazole, etc.) and polycyclic ring systems (naphthyl, quinoline, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. Additionally, the aryl group may be optionally substituted with one or more substituents selected from halo, alkyl, CN, NO$_2$, CO$_2$R, C(O)R, —O—R, —N(R')(R"), —N(R)C(O)R, —N(R)SO$_2$R, —SR, —C(O)N(R')(R"), —OC(O)R, —OC(O)N(R')(R"), SO$_2$, —SOR, —SO$_3$R, —SO$_2$N(R')(R"), halo, cycloalkyl, cycloalkenyl, aryl and heteroaryl.

Each R is independently selected from H, alkyl, cycloalkyl, cycloalkenyl, alkenyl, alkynyl, aralkyl, aryl and heteroaryl. Each R' and R" are independently selected from H, alkyl, cycloalkyl, cycloalkenyl, alkenyl, alkynyl, aralkyl, aryl and heteroaryl; or R' and R" may be taken together with the nitrogen to which they are attached form a 5- to 7-membered ring which may optionally contain a further heteroatom.

The term "heteroatom", particularly as a ring heteroatom, refers to N, O, and S.

All value ranges, for example those given for n and m, are inclusive over the entire range. Thus, a range of 0 to 4 would include the values 0, 1, 2, 3 and 4.

The present invention provides pyrazole derivatives of the formula I:

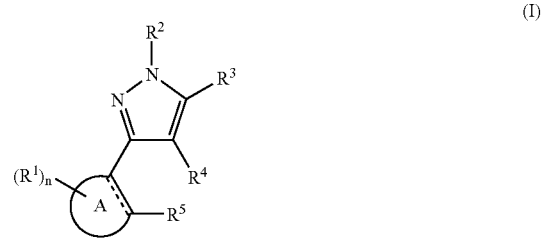

wherein:
ring A is selected from a 5- or 6-membered aromatic rings which may optionally contain 0 to 3 ring heteroatoms;
each R$^1$ is independently selected from alkyl, alkenyl, alkynyl, aralkyl, —O—R$^{11}$, —N(R$^{12}$)(R$^{13}$), —N(R$^{11}$)C(O)R$^{11}$, —N(R$^{11}$)SO$_2$R$^{11}$, —SR$^{11}$, —C(O)R$^{11}$, —C(O)OR$^{11}$, —C(O)N(R$^{12}$)(R$^{13}$), —OC(O)R$^{11}$, —OC(O)N(R$^{12}$)(R$^{13}$), CN, CF$_3$, NO$_2$, SO$_2$, —SOR$^{11}$, —SO$_3$R$^{11}$, —SO$_2$N(R$^{12}$)(R$^{13}$), -alkyl-O—R$^{11}$, cycloalkyl, cycloalkenyl, halo, aryl and heteroaryl;
additionally or alternatively two R$^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from R$^1$;
each R$^{11}$ is independently selected from H, alkyl, alkyl-O-alkyl, alkyl-O-aryl, alkenyl, alkynyl, cycloalkyl, cycloalkenyl, aralkyl, aryl and heteroaryl;
each R$^{12}$ and R$^{13}$ are independently selected from H, alkyl, cycloalkyl, cycloalkenyl, alkyl-O-alkyl, alkyl-O-aryl, alkenyl, alkynyl, aralkyl, aryl and heteroaryl; or R$^{12}$ and R$^{13}$ may be taken together with the nitrogen to which they are attached form a 5- to 7-membered ring which may optionally contain a further heteroatom,
n is 0 to 4;
R$^2$ is selected from H, alkyl, cycloalkyl, cycloalkenyl, alkenyl, alkynyl, aralkyl, aryl, heteroaryl, —C(O)R$^{21}$, —C(O)OR$^{21}$, -alkyl-O-alkyl, -alkyl-O-aryl;
R$^{21}$ is selected from H, alkyl, alkyl-O-alkyl, alkyl-O-aryl, alkenyl, alkynyl, cycloalkyl, cycloalkenyl, aralkyl, aryl and heteroaryl;
R$^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)R$^{31}$, —C(O)OR$^{31}$, —C(O)N(R$^{32}$)(R$^{33}$);
R$^{31}$ is selected from H, alkyl, alkyl-O-alkyl, alkyl-O-aryl, alkenyl, alkynyl, cycloalkyl, cycloalkenyl, aralkyl, aryl and heteroaryl;
R$^{32}$ and R$^{33}$ are independently selected from H, alkyl, cycloalkyl, cycloalkenyl, alkyl-O-alkyl, alkyl-O-aryl, alkenyl, alkynyl, aralkyl, aryl and heteroaryl; or R$^{32}$ and R$^{33}$ may be taken together with the nitrogen to which they are attached form a 5- to 7-membered ring which may optionally contain a further heteroatom and which may be optionally substituted with one or more CN, NO$_2$, CO$_2$R$^{34}$, C(O)R, —O—R$^{34}$, —N(R$^{34}$)(R$^{35}$), —N(R$^{34}$)C(O)R$^{34}$, N(R$^{34}$)SO$_2$R$^{34}$, —SR$^{34}$, —C(O)N(R$^{35}$)(R$^{36}$), —OC(O)R$^{34}$, —OC(O)N(R$^{35}$)(R$^{36}$), SO$_2$, —SOR$^{34}$, —SO$_3$R$^{34}$, —SO$_2$N(R$^{35}$)(R$^{36}$), halo, cycloalkyl, cycloalkenyl, aryl and heteroaryl;

each R$^{34}$ is independently selected from H, alkyl, cycloalkyl, cycloalkeneyl, alkenyl, alkynyl, aralkyl, aryl and heteroaryl;

each R$^{35}$ and R$^{36}$ are independently selected from H, alkyl, cycloalkyl, alkenyl, alkynyl, aralkyl, aryl and heteroaryl; or R$^{35}$ and R$^{36}$ may be taken together with the nitrogen to which they are attached form a 5- to 7-membered ring which may optionally contain a further heteroatom;

R$^4$ is selected from H, alkyl, -alkyl-O-alkyl, cycloalkyl, aralkyl, aryl, heteroaryl,

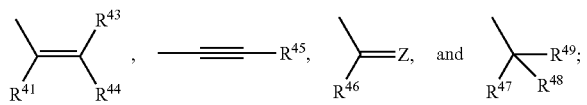

wherein
Z is selected from O, N—OR$^{461}$;

R$^{461}$ is selected from H, alkyl, alkenyl, aralkyl, cycloalkyl, cycloalkenyl, -alkyl-O-alkyl, alkyl-O-aryl and —(CH$_2$)$_q$—R$^{42}$;

R$^{41}$, R$^{43}$, R$^{44}$, R$^{46}$, R$^{47}$, R$^{48}$ and R$^{49}$ are independently selected from H, alkyl, alkenyl, alkynyl, aralkyl, cycloalkyl, cycloalkenyl, -alkyl-O-alkyl, -alkyl-O-aryl, and —(CH$_2$)$_a$—R$^{42}$;

R$^{45}$ is selected from H, alkyl, -alkyl-O-alkyl, -alkyl-O-aryl, aryl, aralkyl, cycloalkyl, cycloalkenyl, and —(CH$_2$)$_a$—R$^{42}$;

R$^{42}$ is selected from —N(R$^{42}$)C(O)R$^{421}$, —N(R$^{421}$)SO$_2$R$^{421}$, OR$^{421}$, —SR$^{421}$, —C(O)R$^{421}$, —C(O)OR$^{421}$, —C(O)N(R$^{422}$)(R$^{423}$), —OC(O)R$^{421}$, —OC(O)N(R$^{422}$)(R$^{423}$), CN, CF$_3$, NO$_2$, SO$_2$, —SOR$^{421}$, —SO$_3$R$^{421}$, —SO$_2$N(R$^{422}$)(R$^{423}$), -alkyl-O-alkyl, -alkyl-O-aryl, halo, cycloalkyl, cycloalkenyl, aryl and heteroaryl;

or R$^{42}$ is selected from a group having the formula

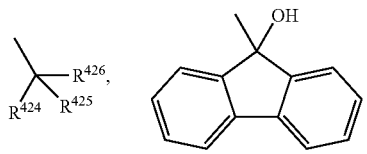

each R$^{421}$ is independently selected from H, alkyl, cycloalkyl, alkenyl, alkynyl, aralkyl, aryl and heteroaryl;

each R$^{422}$ and R$^{423}$ are independently selected from H, alkyl, cycloalkyl, alkenyl, alkynyl, aralkyl, aryl and heteroaryl; or R$^{422}$ and R$^{423}$ may be taken together with the nitrogen to which they are attached form a 5- to 7-membered ring which may optionally contain a further heteroatom;

each R$^{424}$ is independently selected from H, OH, alkyl, cycloalkyl, alkenyl, alkynyl, aralkyl, aryl and heteroaryl;

each R$^{425}$ and R$^{426}$ are independently selected from H, alkyl, cycloalkyl, alkenyl, alkynyl, aralkyl, aryl and heteroaryl; or R$^{425}$ and R$^{426}$ may be taken together with the carbon to which they are attached form a 5- to 7-membered ring which may optionally contain a further heteroatom;

a is 1 to 6;

R$^5$ is selected from H, OR$^{51}$, —SR$^{51}$, alkyl, cycloalkyl, cycloalkenyl, alkenyl, alkynyl, CN, CF$_3$, NO$_2$, SO$_2$, —SOR$^{51}$, —SO$_3$R$^{51}$, —SO$_2$N(R$^{52}$)(R$^{53}$), -alkyl-O-alkyl, halo, aralkyl, aryl, heteroaryl, —C(O)R$^{51}$, —C(O)OR$^{51}$, —C(O)N(R$^{52}$)(R$^{53}$), —OC(O)R$^{51}$, —OC(O)N(R$^{52}$)(R$^{53}$), —O(CH$_2$)$_e$C(O)OR$^{11}$, —O(CH$_2$)$_e$C(O)N(R$^{52}$)(R$^{53}$), —N(R$^{52}$)(R$^{53}$), —N(R$^{51}$)C(O)R$^{51}$, and —N(R$^{51}$)SO$_2$R$^{51}$;

each R$^{51}$ is independently selected from H, alkyl, cycloalkyl, cycloalkenyl, alkenyl, alkynyl, aralkyl, aryl and heteroaryl;

R$^{52}$ and R$^{53}$ are independently selected from H, alkyl, cycloalkyl, cycloalkenyl, alkenyl, alkynyl, aralkyl, aryl and heteroaryl; or R$^{52}$ and R$^{53}$ may be taken together with the nitrogen to which they are attached form a 5- to 7-membered ring which may optionally contain a further heteroatom;

e is 1 to 6;

alternatively, —O—R$^{51}$ is combined with R$^{41}$, R$^{46}$, or R$^{47}$ to give a 6-membered ring that is fused to ring A and to the pyrazole ring;

or R$^5$ is selected from a group having the formula:

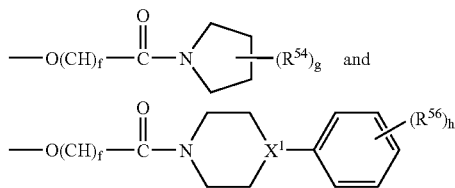

wherein
each R$^{54}$ and R$^{56}$ is independently selected from —OR$^{57}$, halo, alkyl, cycloalkyl, cycloalkenyl, alkenyl, alkynyl, NO$_2$, CN, —C(O)R$^{57}$, —C(O)OR$^{57}$, —C(O)N(R$^{58}$)(R$^{59}$), —OC(O)R$^{57}$, —OC(O)N(R$^{58}$)(R$^{59}$), O(CH$_2$)$_i$C(O)OR$^{57}$, —O(CH$_2$)$_i$C(O)N(R$^{58}$)(R$^{59}$)—N(R$^{58}$)(R$^{59}$), —N(R$^{57}$)C(O)R$^{57}$, —N(R$^{57}$)SO$_2$R$^{57}$, aralkyl, aryl and heteroaryl;

each R$^{57}$ is independently selected from H, alkyl, cycloalkyl, cycloalkenyl, alkenyl, alkynyl, aralkyl, aryl and heteroaryl;

R$^{58}$ and R$^{59}$ are independently selected from H, alkyl, cycloalkyl, cycloalkenyl, alkenyl, alkynyl, aralkyl, aryl and heteroaryl; or R$^{52}$ and R$^{53}$ may be taken together with the nitrogen to which they are attached form a 5- to 7-membered ring which may optionally contain a further heteroatom;

i is 1 to 6;

X$^1$ is selected from N and CH;

f is 1 to 6;

g is 0 to 4; and h if 0 to 5;

or a pharmaceutically acceptable salt or hydrate thereof.

The dashed line in Ring A represents an optional double bond, as would be understood by the ordinarily skilled worker in the art.

The substances according to the invention may also be present as salts. In the context of the invention, preference is given to pharmaceutically acceptable salts. Pharmaceutically acceptable salts refers to an acid addition salt or a basic addition salt of a compound of the invention in which the resulting counter ion is understood in the art to be generally acceptable for pharmaceutical uses. Pharmaceutically acceptable salts can be salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, maleic acid, fumaric acid, malic acid, citric acid, tartaric acid, lactic acid, benzoic acid, or methanesulfonic acid, ethanesulfonic acid, phenylsulfonic acid, toluenesulfonic acid or naphthalenedisulfonic acid. Pharmaceutically acceptable salts can also be metal or ammonium salts of the compounds according to the invention. Particular preference is given to, for example, sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine. (see, Berge et al. *J. Pharm. Sci.* 1977, 66, 1-19.)

When one or more chiral centers are present in the compounds of the present invention, the individual isomers and mixtures thereof (e.g., racemates, etc.) are intended to be encompassed by the formulae depicted herein. In certain embodiments, compounds of the invention may exist in several tautomeric forms. Accordingly, the chemical structures depicted herein encompass all possible tautomeric forms of the illustrated compounds. Compounds of the invention may exist in various hydrated forms.

It is understood that when n is a value greater than 1, each $R^1$ group may be selected independently. Thus, when more than one $R^1$ group is present, the $R^1$ groups may be selected from any of the stated groups so as to be the same or different. This also holds true for any other group or substituent which may be selected independently from among various groups or values.

In preferred embodiments, $R^5$ is selected from $OR^{51}$, —OC(O)$R^{51}$, —OC(O)N($R^{52}$)($R^{53}$), O(CH$_2$)$_e$C(O)OR$^{51}$, —O(CH$_2$)$_e$C(O)N($R^{52}$)($R^{53}$), —N($R^{52}$)($R^{53}$), —N($R^{51}$)C(O)$R^{51}$, and —N($R^{51}$)SO$_2$R$^{51}$.

In one embodiment of the invention, $R^5$ is selected to be a group of the formula O—$R^6$ to give a compound of the formula II

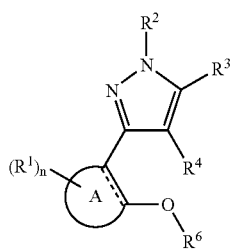

(II)

wherein:
ring A is selected from a 5- or 6-membered aromatic rings which may optionally contain 0 to 3 ring heteroatoms;
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2$R$^{11}$, —SR$^{11}$, —C(O)R$^{11}$, —C(O)OR$^{11}$, —C(O)N($R^{12}$)($R^{13}$), —OC(O)R$^{11}$, —OC(O)N($R^{12}$)($R^{13}$), CN, CF$_3$, NO$_2$, SO$_2$, —SOR$^{11}$, —SO$_3$R$^{11}$, —SO$_2$N($R^{12}$)($R^{13}$), -alkyl-O—$R^{11}$, cycloalkyl, cycloalkenyl, halo, aryl and heteroaryl;
additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;
each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;
each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom,
n is 0 to 4;
$R^2$ is selected from H, alkyl, cycloalkyl, cycloalkenyl, alkenyl, alkynyl, aralkyl, aryl, heteroaryl, —C(O)$R^{21}$, —C(O)OR$^{21}$, -alkyl-O-alkyl, -alkyl-O-aryl;
$R^{21}$ is selected from H, alkyl, alkyl-O-alkyl, alkyl-O-aryl, alkenyl, alkynyl, cycloalkyl, cycloalkenyl, aralkyl, aryl and heteroaryl;
$R^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)$R^{31}$, —C(O)OR$^{31}$, —C(O)N($R^{32}$)($R^{33}$);
$R^{31}$ is selected from H, alkyl, alkyl-O-alkyl, alkyl-O-aryl, alkenyl, alkynyl, cycloalkyl, cycloalkenyl, aralkyl, aryl and heteroaryl;
$R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, NO$_2$, CO$_2$R$^{34}$, C(O)R$^{34}$, —O—R$^{34}$, —N(R$^{34}$)(R$^{35}$), —N(R$^{34}$)C(O)R$^{34}$, N(R$^{34}$)SO$_2$R$^{34}$, —SR$^{34}$, —C(O)N(R$^{35}$)(R$^{36}$), —OC(O)R$^{34}$, —OC(O)N(R$^{35}$)(R$^{36}$), SO$_2$, —SOR$^{34}$, —SO$_3$R$^{34}$, —SO$_2$N(R$^{35}$)(R$^{36}$), halo, cycloalkyl, cycloalkenyl, aryl and heteroaryl;
each $R^{34}$ is independently selected from H, alkyl, cycloalkyl, cycloalkeneyl, alkenyl, alkynyl, aralkyl, aryl and heteroaryl;
each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;
$R^4$ is selected from H, alkyl, -alkyl-O-alkyl, cycloalkyl, aralkyl, aryl, heteroaryl,

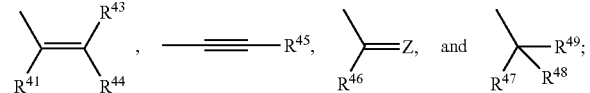

wherein
Z is selected from O, N—OR$^{461}$;
$R^{461}$ is selected from H, alkyl, alkenyl, aralkyl, cycloalkyl, -alkyl-O-alkyl, alkyl-O-aryl and —(CH$_2$)$_q$—R$^{42}$;
$R^{41}$, $R^{43}$, $R^{44}$, $R^{46}$, $R^{47}$, $R^{48}$ and $R^{49}$ are independently selected from H, alkyl, alkenyl, alkynyl, aralkyl, cycloalkyl, cycloalkenyl, -alkyl-O-alkyl, -alkyl-O-aryl, and —(CH$_2$)$_q$—R$^{42}$;

$R^{45}$ is selected from H, alkyl, -alkyl-O-alkyl, -alkyl-O-aryl, aryl, aralkyl, cycloalkyl, cycloalkenyl, and —$(CH_2)_a$—$R^{42}$;

$R^{42}$ is selected from —$N(R^{421})C(O)R^{421}$, —$N(R^{421})SO_2R^{421}$, $OR^{421}$, $SR^{421}$, —$C(O)R^{421}$, —$(O)OR^{421}$, —$C(O)N(R^{422})(R^{423})$—$OC(O)R^{421}$, —$OC(O)N(R^{422})(R^{423})$, CN, $CF_3$, $NO_2$, $SO_2$, —$SOR^{421}$, —$SO_3R^{421}$, —$SO_2N(R^{422})(R^{423})$, -alkyl-O-alkyl, -alkyl-O-aryl, halo, cycloalkyl, cycloalkenyl, aryl and heteroaryl;

or $R^{42}$ is selected from a group having the formula

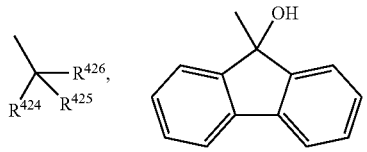

each $R^{421}$ is independently selected from H, alkyl, cycloalkyl, alkenyl, alkynyl, aralkyl, aryl and heteroaryl;

each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;

each $R^{424}$ is independently selected from H, OH, alkyl, cycloalkyl, alkenyl, alkynyl, aralkyl, aryl and heteroaryl;

each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to which they are attached form a 5- to 7-membered ring which may optionally contain a further heteroatom;

a is 1 to 6;

$R^6$ is selected from H, alkyl, cycloalkyl, cycloalkenyl, alkenyl, alkynyl, aralkyl, aryl, heteroaryl, —$C(O)R^{51}$, —$C(O)N(R^{52})(R^{53})$, $(CH_2)_eC(O)OR^{51}$, and —$(CH_2)_eC(O)N(R^{52})(R^{53})$, each $R^{51}$ is independently selected from H, alkyl, cycloalkyl, cycloalkenyl, alkenyl, alkynyl, aralkyl, aryl and heteroaryl;

$R^{52}$ and $R^{53}$ are independently selected from H, alkyl, cycloalkyl, cycloalkenyl, alkenyl, alkynyl, aralkyl, aryl and heteroaryl;

or $R^{52}$ and $R^{53}$ may be taken together with the nitrogen to which they are attached form a 5- to 7-membered ring which may optionally contain a further heteroatom;

e is 1 to 6;

alternatively, $R^6$ is combined with $R^{41}$, $R^{46}$, or $R^{47}$ to give a 6-membered ring that is fused to ring A and to the pyrazole ring;

or $R^6$ is selected from a group having the formula:

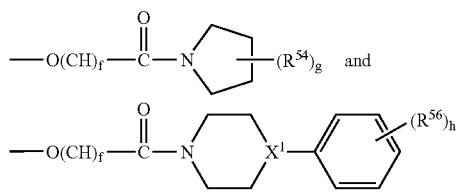

wherein each $R^{54}$ and $R^{56}$ is independently selected from —$OR^{57}$, halo, alkyl, cycloalkyl, cycloalkenyl, alkenyl, alkynyl, $NO_2$, CN, —$C(O)R^{57}$, —$C(O)OR^{57}$, —$C(O)N(R^{58})(R^{59})$, —$OC(O)R^{57}$, —$OC(O)N(R^{58})(R^{59})$, $O(CH_2)_cC(O)OR^{57}$, —$O(CH_2)_cC(O)N(R^{58})(R^{59})$, —$N(R^{58})(R^{59})$, —$N(R^{57})C(O)R^{57}$, —$N(R^{57})SO_2R^{57}$, aralkyl, aryl and heteroaryl;

each $R^{57}$ is independently selected from H, alkyl, cycloalkyl, cycloalkenyl, alkenyl, alkynyl, aralkyl, aryl and heteroaryl;

$R^{58}$ and $R^{59}$ are independently selected from H, alkyl, cycloalkyl, cycloalkenyl, alkenyl, alkynyl, aralkyl, aryl and heteroaryl; or $R^{52}$ and $R^{53}$ may be taken together with the nitrogen to which they are attached form a 5- to 7-membered ring which may optionally contain a further heteroatom;

i is 1 to 6;

$X^1$ is selected from N and CH;

f is 1 to 6;

g is 0 to 4; and h if 0 to 5;

or a pharmaceutically acceptable salt or hydrate thereof.

In a preferred embodiment of the invention, the ring A of the compound according to formula II is selected to be a phenyl or substituted phenyl to give a compound of the formula III:

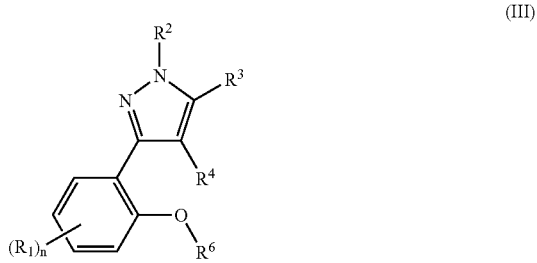

(III)

wherein:

each $R^1$ is independently selected from alkyl, alkenyl, alkynyl, aralkyl, —O—$R^{11}$, —$N(R^{12})(R^{13})$, —$N(R^{11})C(O)R^{11}$, —$N(R^{11})SO_2R^{11}$, —$SR^{11}$, —$C(O)R^{11}$, —$C(O)OR^{11}$, —$C(O)N(R^{12})(R^{13})$, —$OC(O)R^{11}$, —$OC(O)N(R^{12})(R^{13})$, CN, $CF_3$, $NO_2$, $SO_2$, —$SOR^{11}$, —$SO_3R^{11}$, —$SO_2N(R^{12})(R^{13})$, -alkyl-O—$R^{11}$, cycloalkyl, cycloalkenyl, halo, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

$R^2$ is selected from H, alkyl, cycloalkyl, cycloalkenyl, alkenyl, alkynyl, aralkyl, aryl, heteroaryl, —C(O)R, —C(O)OR$^{21}$, -alkyl-O-alkyl, -alkyl-O-aryl;

$R^{21}$ is selected from H, alkyl, alkyl-O-alkyl, alkyl-O-aryl, alkenyl, alkynyl, cycloalkyl, cycloalkenyl, aralkyl, aryl and heteroaryl;

$R^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)$R^{31}$, —C(O)O$R^{31}$, —C(O)N($R^{32}$)($R^{33}$);

$R^{31}$ is selected from H, alkyl, alkyl-O-alkyl, alkyl-O-aryl, alkenyl, alkynyl, cycloalkyl, cycloalkenyl, aralkyl, aryl and heteroaryl;

$R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, $NO_2$, $CO_2R^{34}$, C(O)$R^{34}$, —O—$R^{34}$, —N($R^{34}$)($R^{35}$), —N($R^{34}$)C(O)$R^{34}$, N($R^{34}$)$SO_2R^{34}$, —S$R^{34}$, —C(O)N($R^{35}$)($R^{36}$), —OC(O)$R^{34}$, —OC(O)N($R^{35}$)($R^{36}$), $SO_2$, —SO$R^{34}$, —$SO_3R^{34}$, —$SO_2$N($R^{35}$)($R^{36}$), halo, cycloalkyl, cycloalkenyl, aryl and heteroaryl;

each $R^{34}$ is independently selected from H, alkyl, cycloalkyl, cycloalkeneyl, alkenyl, alkynyl, aralkyl, aryl and heteroaryl;

each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;

$R^4$ is selected from H, alkyl, -alkyl-O-alkyl, cycloalkyl, aralkyl, aryl, heteroaryl,

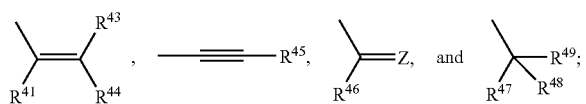

wherein

Z is selected from O, N—O$R^{461}$;

$R^{461}$ is selected from H, alkyl, alkenyl, aralkyl, cycloalkyl, cycloalkenyl, -alkyl-O-alkyl, alkyl-O-aryl and —(CH$_2$)$_a$—$R^{42}$ $R^{41}$, $R^{43}$, $R^{44}$, $R^{46}$, $R^{47}$, $R^{48}$ and $R^{49}$ are independently selected from H, alkyl, alkenyl, alkynyl, aralkyl, cycloalkyl, cycloalkenyl, -alkyl-O-alkyl, -alkyl-O-aryl, and —(CH$_2$)$_a$—$R^{42}$;

$R^{45}$ is selected from H, alkyl, -alkyl-O-alkyl, -alkyl-O-aryl, aryl, aralkyl, cycloalkyl, cycloalkenyl, and —(CH$_2$)$_a$—$R^{42}$;

$R^{42}$ is selected from —N($R^{421}$)C(O)$R^{42}$, —N($R^{42}$)$SO_2R^{421}$, O$R^{421}$, —S$R^{421}$, —C(O)$R^{421}$, —C(O)O$R^{421}$, —C(O)N($R^{422}$)($R^{423}$), —OC(O)$R^{421}$, —OC(O)N($R^{422}$)($R^{423}$), CN, CF$_3$, NO$_2$, SO$_2$, —SO$R^{421}$, —SO$R^{421}$, —SO$_2$N($R^{422}$)($R^{423}$), -alkyl-O-alkyl, -alkyl-O-aryl, halo, cycloalkyl, cycloalkenyl, aryl and heteroaryl;

or $R^{42}$ is selected from a group having the formula

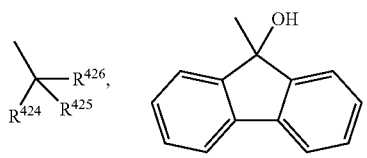

each $R^{421}$ is independently selected from H, alkyl, cycloalkyl, alkenyl, alkynyl, aralkyl, aryl and heteroaryl;

each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;

each $R^{424}$ is independently selected from H, OH, alkyl, cycloalkyl, alkenyl, alkynyl, aralkyl, aryl and heteroaryl;

each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to which they are attached form a 5- to 7-membered ring which may optionally contain a further heteroatom;

a is 1 to 6;

$R^6$ is selected from H, alkyl, cycloalkyl, cycloalkenyl, alkenyl, alkynyl, aralkyl, aryl, heteroaryl, —C(O)$R^{51}$, —C(O)N($R^{52}$)($R^{53}$), (CH$_2$)$_e$C(O)O$R^{51}$, and —(CH$_2$)$_e$C(O)N($R^{52}$)($R^{53}$), each $R^{51}$ is independently selected from H, alkyl, cycloalkyl, cycloalkenyl, alkenyl, alkynyl, aralkyl, aryl and heteroaryl;

$R^{52}$ and $R^{53}$ are independently selected from H, alkyl, cycloalkyl, cycloalkenyl, alkenyl, alkynyl, aralkyl, aryl and heteroaryl;

or $R^{52}$ and $R^{53}$ may be taken together with the nitrogen to which they are attached form a 5- to 7-membered ring which may optionally contain a further heteroatom;

e is 1 to 6;

alternatively, $R^6$ is combined with $R^{41}$, $R^{46}$, or $R^{47}$ to give a 6-membered ring that is fused to ring A and to the pyrazole ring;

or $R^6$ is selected from a group having the formula:

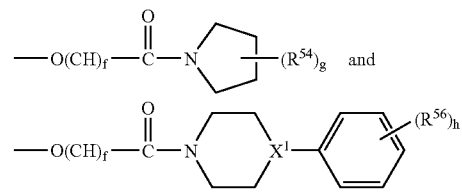

wherein each $R^{54}$ and $R^{56}$ is independently selected from —O$R^{57}$, halo, alkyl, cycloalkyl, cycloalkenyl, alkenyl, alkynyl, NO$_2$, CN, —C(O)$R^{57}$, —C(O)O$R^{57}$, —C(O)N($R^{58}$)($R^{59}$), —OC(O)$R^{57}$, —OC(O)N($R^{58}$)($R^{59}$), O(CH$_2$)$_i$C(O)O$R^{57}$, —O(CH$_2$)$_i$C(O)N($R^{58}$)($R^{59}$), —N($R^{58}$)($R^{59}$), —N($R^{57}$)C(O)$R^{57}$, —N($R^{57}$)SO$_2R^{57}$, aralkyl, aryl and heteroaryl;

each $R^{57}$ is independently selected from H, alkyl, cycloalkyl, cycloalkenyl, alkenyl, alkynyl, aralkyl, aryl and heteroaryl;

$R^{58}$ and $R^{59}$ are independently selected from H, alkyl, cycloalkyl, cycloalkenyl, alkenyl, alkynyl, aralkyl, aryl and heteroaryl; or $R^{52}$ and $R^{53}$ may be taken together with the nitrogen to which they are attached form a 5- to 7-membered ring which may optionally contain a further heteroatom;

i is 1 to 6;

$X^1$ is selected from N and CH;

f is 1 to 6;

g is 0 to 4; and h if 0 to 5;

or a pharmaceutically acceptable salt or hydrate thereof.

In a further embodiment of the invention, $R^4$ of a compound according to formula III is selected to be a group of the formula

and the ring A is selected to be a phenyl or substituted phenyl to give a compound of the formula IV:

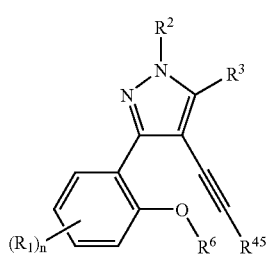

(IV)

wherein:
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3R^{11}$, —SO$_2$N($R^{12}$)($R^{13}$), -alkyl-O—$R^{11}$, cycloalkyl, cycloalkenyl, halo, aryl and heteroaryl;
  additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;
    each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;
    each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom,
n is 0 to 4;
$R^2$ is selected from H, alkyl, cycloalkyl, cycloalkenyl, alkenyl, alkynyl, aralkyl, aryl, heteroaryl, —C(O)$R^{21}$, —C(O)O$R^{21}$, -alkyl-O-alkyl, -alkyl-O-aryl;
  $R^{21}$ is selected from H, alkyl, alkyl-O-alkyl, alkyl-O-aryl, alkenyl, alkynyl, cycloalkyl, cycloalkenyl, aralkyl, aryl and heteroaryl;
$R^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)$R^{31}$, —C(O)O$R^{31}$, —C(O)N($R^{32}$)($R^{33}$);
  $R^{31}$ is selected from H, alkyl, alkyl-O-alkyl, alkyl-O-aryl, alkenyl, alkynyl, cycloalkyl, cycloalkenyl, aralkyl, aryl and heteroaryl;
  $R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, NO$_2$, CO$_2R^{34}$, C(O)$R^{34}$—O—$R^{34}$—N($R^{34}$)($R^{35}$), —N($R^{34}$)C(O)$R^{34}$, —N($R^{34}$)SO$_2R^{34}$, —S$R^{34}$, —C(O)N($R^{35}$)($R^{36}$), —OC(O)$R^{34}$, —OC(O)N($R^{35}$)($R^{36}$), SO$_2$, —SO$R^{34}$, —SO$_3R^{34}$, —SO$_2$N($R^{35}$)($R^{36}$), halo, cycloalkyl, cycloalkenyl, aryl and heteroaryl;
    each $R^{34}$ is independently selected from H, alkyl, cycloalkyl, cycloalkeneyl, alkenyl, alkynyl, aralkyl, aryl and heteroaryl;
    each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;
$R^{45}$ is selected from H, alkyl, -alkyl-O-alkyl, -alkyl-O-aryl, aryl, aralkyl, cycloalkyl, cycloalkenyl, and —(CH$_2$)$_a$—$R^{42}$;
$R^{42}$ is selected from —N($R^{421}$)C(O)$R^{421}$, —N($R^{421}$)SO$_2R^{421}$, O$R^{421}$, —S$R^{421}$, C(O)$R^{421}$, —C(O)O$R^{421}$, —C(O)N($R^{422}$)($R^{423}$), —OC(O)$R^{421}$, —OC(O)N($R^{422}$)($R^{423}$), CN, CF$_3$, NO$_2$, SO$_2$, —SO$R^{421}$, —SO$_3R^{421}$, —SO$_2$N($R^{422}$)($R^{423}$), -alkyl-O-alkyl, -alkyl-O-aryl, halo, cycloalkyl, cycloalkenyl, aryl and heteroaryl;
or $R^{42}$ is selected from a group having the formula

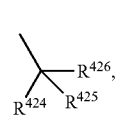 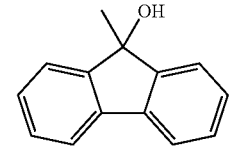

each $R^{421}$ is independently selected from H, alkyl, cycloalkyl, alkenyl, alkynyl, aralkyl, aryl and heteroaryl;
  each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;
  each $R^{424}$ is independently selected from H, OH, alkyl, cycloalkyl, alkenyl, alkynyl, aralkyl, aryl and heteroaryl;
  each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to which they are attached form a 5- to 7-membered ring which may optionally contain a further heteroatom;
  a is 1 to 6;
$R^6$ is selected from H, alkyl, cycloalkyl, alkenyl, alkynyl, aralkyl, aryl, heteroaryl, —C(O)$R^{51}$, —C(O)N($R^{52}$)($R^{53}$), (CH$_2$)$_e$C(O)O$R^{51}$, and —(CH$_2$)$_e$C(O)N($R^{52}$)($R^{53}$),
  each $R^{51}$ is independently selected from H, alkyl, cycloalkyl, cycloalkenyl, alkenyl, alkynyl, aralkyl, aryl and heteroaryl;
  $R^{52}$ and $R^{53}$ are independently selected from H, alkyl, cycloalkyl, cycloalkenyl, alkenyl, alkynyl, aralkyl, aryl and heteroaryl;
  or $R^{52}$ and $R^{53}$ may be taken together with the nitrogen to which they are attached form a 5- to 7-membered ring which may optionally contain a further heteroatom;
  e is 1 to 6;

or $R^6$ is selected from a group having the formula:

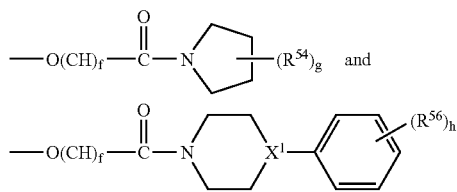

wherein
 each $R^{54}$ and $R^{56}$ is independently selected from OH, halo, alkyl, cycloalkyl, alkenyl, alkynyl, $NO_2$, CN, —$C(O)R^{57}$, —$C(O)OR^{57}$, —$C(O)N(R^{58})(R^{59})$, —$OC(O)R^{57}$, —$OC(O)N(R^{58})(R^{59})$, $O(CH_2)_iC(O)$ $OR^{57}$, —$O(CH_2)_iC(O)N(R^{58})(R^{59})$, —$N(R^{58})(R^{59})$, —$N(R^{57})C(O)R^{57}$, —$N(R^{57})SO_2R^{57}$, aralkyl, aryl and heteroaryl;
 each $R^{57}$ is independently selected from H, alkyl, cycloalkyl, alkenyl, alkynyl, aralkyl, aryl and heteroaryl;
 $R^{58}$ and $R^{59}$ are independently selected from H, alkyl, cycloalkyl, alkenyl, alkynyl, aralkyl, aryl and heteroaryl; or $R^{52}$ and $R^{53}$ may be taken together with the nitrogen to which they are attached form a 5- to 7-membered ring which may optionally contain a further heteroatom;
 i is 1 to 6;
 $X^1$ is selected from N and CH;
 f is 1 to 6;
 g is 0 to 4; and
 h if 0 to 5;
or a pharmaceutically acceptable salt or hydrate thereof.

TABLE 1

Table 1 provides representative embodiments for compounds of the formula IV.

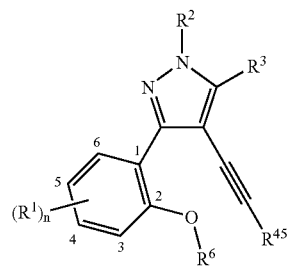

| No. | $R^1$ | $R^2$ | $R^3$ | $R^6$ | $R^{45}$ | MW |
|---|---|---|---|---|---|---|
| 1 | — | $CH_3$ | H | H | $CH_3$ | 212.25 |
| 21432 | — | $CH_3$ | H | H | 4-methylphenyl | 288.34 |
| 21433 | — | $CH_3$ | H | H | 4-methoxyphenyl | 304.34 |
| 21434 | — | $CH_3$ | H | H | 4-chlorophenyl | 308.76 |
| 21435 | — | $CH_3$ | H | H | cyclohexenyl | 278.35 |
| 21436 | — | $CH_3$ | H | H | —$(CH_2)_3CN$ | 265.31 |
| 21437 | — | $CH_3$ | H | H | 2-fluorophenyl | 292.31 |
| 21438 | — | $CH_3$ | H | H | —$C(CH_3)_3$ | 254.33 |
| 21439 | — | $CH_3$ | H | H | —$(CH_2)_3Cl$ | 274.75 |
| 21440 | — | $CH_3$ | H | H | —$(CH_2)_3CH_3$ | 254.33 |
| 21441 | — | $CH_3$ | H | H | —$CH_2OCH_3$ | 242.27 |

TABLE 1-continued

Table 1 provides representative embodiments for compounds of the formula IV.

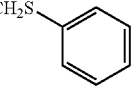

| No. | R¹ | R² | R³ | R⁶ | R⁴⁵ | MW |
|---|---|---|---|---|---|---|
| 21442 | — | CH₃ | H | H | —C(CH₃)₂OH | 256.30 |
| 21443 | — | CH₃ | H | H | —CH₂S-Ph | 320.41 |
| 21444 | — | —CH₂-Ph | H | H | 4-CH₃-C₆H₄ | 364.44 |
| 21445 | — | —CH₂-Ph | H | H | 4-OCH₃-C₆H₄ | 380.44 |
| 21446 | — | —CH₂-Ph | H | H | —CH₂S-Ph | 396.51 |
| 21447 | 5-CH₃ | CH₃ | H | H | 4-CH₃-C₆H₄ | 302.37 |
| 21448 | 5-CH₃ | CH₃ | H | H | 4-OCH₃-C₆H₄ | 318.37 |
| 23306 | 5-CH₃ | CH₃ | H | H | 4-Cl-C₆H₄ | 322.79 |
| 23307 | 5-CH₃ | CH₃ | H | H | cyclohexenyl | 292.37 |
| 23308 | 5-CH₃ | CH₃ | H | H | —(CH₂)₃CN | 279.34 |
| 23309 | 5-CH₃ | CH₃ | H | H | 2-F-C₆H₄ | 306.33 |
| 23310 | 5-CH₃ | CH₃ | H | H | —C(CH₃)₃ | 268.35 |
| 23311 | 5-CH₃ | CH₃ | H | H | —(CH₂)₃Cl | 288.77 |
| 23312 | 5-CH₃ | CH₃ | H | H | —(CH₂)₃CH₃ | 268.35 |
| 23313 | 5-CH₃ | CH₃ | H | H | —CH₂OCH₃ | 256.30 |

TABLE 1-continued

Table 1 provides representative embodiments for compounds of the formula IV.

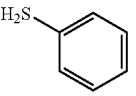

| No. | R¹ | R² | R³ | R⁶ | R⁴⁵ | MW |
|---|---|---|---|---|---|---|
| 23314 | 5-CH₃ | CH₃ | H | H | —C(CH₃)₂OH | 270.33 |
| 23315 | 5-CH₃ | CH₃ | H | H | —CH₂S—Ph | 334.43 |
| 23316 | 5-Cl | CH₃ | H | H | 4-methylphenyl | 322.79 |
| 23317 | 5-Cl | CH₃ | H | H | 4-methoxyphenyl | 338.79 |
| 23318 | 5-Cl | CH₃ | H | H | 4-chlorophenyl | 343.21 |
| 23319 | 5-Cl | CH₃ | H | H | cyclohexenyl | 312.79 |
| 23320 | 5-Cl | CH₃ | H | H | —(CH₂)₃CN | 299.75 |
| 23321 | 5-Cl | CH₃ | H | H | 2-fluorophenyl | 326.75 |
| 23322 | 5-Cl | CH₃ | H | H | —C(CH₃)₃ | 288.77 |
| 23323 | 5-Cl | CH₃ | H | H | —(CH₂)₃Cl | 309.19 |
| 23324 | 5-Cl | CH₃ | H | H | —(CH₂)₃CH₃ | 288.77 |
| 23325 | 5-Cl | CH₃ | H | H | —CH₂OCH₃ | 276.62 |
| 23326 | 5-Cl | CH₃ | H | H | —C(CH₃)₂OH | 290.74 |
| 23327 | 5-Cl | CH₃ | H | H | —CH₂S—Ph | 354.85 |
| 23328 | 5-Cl | —CH₂Ph | H | H | 4-methylphenyl | 398.88 |

TABLE 1-continued

Table 1 provides representative embodiments for compounds of the formula IV.

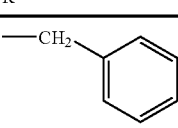

| No. | R¹ | R² | R³ | R⁶ | R⁴⁵ | MW |
|---|---|---|---|---|---|---|
| 23329 | 5-Cl | —CH₂—C₆H₅ | H | H | 4-methoxyphenyl | 414.88 |
| 23330 | 5-Cl | —CH₂—C₆H₅ | H | H | 4-chlorophenyl | 419.30 |
| 23331 | 5-Cl | —CH₂—C₆H₅ | H | H | cyclohexenyl | 388.89 |
| 23332 | 5-Cl | —CH₂—C₆H₅ | H | H | —(CH₂)₃CN | 375.85 |
| 23333 | 5-Cl | —CH₂—C₆H₅ | H | H | 2-fluorophenyl | 402.85 |
| 23334 | 5-Cl | —CH₂—C₆H₅ | H | H | —C(CH₃)₃ | 364.87 |
| 23335 | 5-Cl | —CH₂—C₆H₅ | H | H | —(CH₂)₃Cl | 385.29 |
| 23336 | 5-Cl | —CH₂—C₆H₅ | H | H | —(CH₂)₃CH₃ | 364.87 |
| 23337 | 5-Cl | —CH₂—C₆H₅ | H | H | —CH₂OCH₃ | 352.81 |
| 23338 | 5-Cl | —CH₂—C₆H₅ | H | H | —C(CH₃)₂OH | 366.84 |
| 23339 | 5-Cl | —CH₂—C₆H₅ | H | H | —CH₂S—C₆H₅ | 430.95 |

TABLE 1-continued

Table 1 provides representative embodiments for compounds of the formula IV.

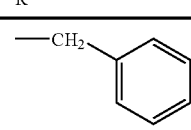

| No. | R¹ | R² | R³ | R⁶ | R⁴⁵ | MW |
|---|---|---|---|---|---|---|
| 23340 | — | —CH₂—C₆H₅ | H | H | —(CH₂)₃CH₃ | 330.42 |
| 23341 | 5-Br | CH₃ | H | H | 4-methylphenyl | 367.24 |
| 23342 | 5-Br | CH₃ | H | H | 4-methoxyphenyl | 383.24 |
| 23343 | 5-Br | CH₃ | H | H | 4-chlorophenyl | 387.66 |
| 23344 | 5-Br | CH₃ | H | H | cyclohexenyl | 357.24 |
| 23345 | 5-Br | CH₃ | H | H | —(CH₂)₃CN | 344.21 |
| 23346 | 5-Br | CH₃ | H | H | 2-fluorophenyl | 371.20 |
| 23347 | 5-Br | CH₃ | H | H | CH₃OCCHCOCH₃ (with CH₂) $\parallel$ O O | 421.24 |
| 23348 | 5-Br | CH₃ | H | H | phenyl | 353.21 |
| 23350 | 5-Br | CH₃ | H | H | —(CH₂)₃Cl | 353.64 |
| 23351 | 5-Br | CH₃ | H | H | —(CH₂)₃CH₃ | 333.22 |
| 23352 | 5-Br | CH₃ | H | H | —CH₂OCH₃ | 321.17 |
| 23353 | 5-Br | CH₃ | H | H | —C(CH₃)₂OH | 335.20 |
| 23354 | 5-Br | CH₃ | H | H | —CH₂S—C₆H₅ | 399.30 |

TABLE 1-continued

Table 1 provides representative embodiments for compounds of the formula IV.

| No. | R¹ | R² | R³ | R⁶ | R⁴⁵ | MW |
|---|---|---|---|---|---|---|
| 23355 | 5-Br | CH₃ | H | H | 1-hydroxy-1-methyl-1-phenylmethyl (HO, CH₃ on C attached to phenyl) | 397.27 |
| 23356 | 5-Br | CH₃ | H | H | 1-hydroxycyclohexyl | 375.26 |
| 23357 | 5-Br | CH₂CH₂OH | H | H | 4-methylphenyl | 397.27 |
| 23358 | 5-Br | CH₂CH₂OH | H | H | 4-methoxyphenyl | 413.26 |
| 23359 | 5-Br | CH₂CH₂OH | H | H | 4-chlorophenyl | 417.68 |
| 23360 | 5-Br | CH₂CH₂OH | H | H | cyclohex-1-enyl | 387.27 |
| 23361 | 5-Br | CH₂CH₂OH | H | H | —(CH₂)₃CN | 374.23 |
| 23362 | 5-Br | CH₂CH₂OH | H | H | 2-fluorophenyl | 401.23 |
| 23363 | 5-Br | CH₂CH₂OH | H | H | CH₃OCOCH(CH₂—)COCH₃ | 451.27 |
| 23364 | 5-Br | CH₂CH₂OH | H | H | phenyl | 383.24 |
| 23366 | 5-Br | CH₂CH₂OH | H | H | —(CH₂)₃Cl | 383.67 |
| 23367 | 5-Br | CH₂CH₂OH | H | H | —(CH₂)₃CH₃ | 363.25 |
| 23368 | 5-Br | CH₂CH₂OH | H | H | —C(CH₃)₂OH | 365.22 |

TABLE 1-continued

Table 1 provides representative embodiments for compounds of the formula IV.

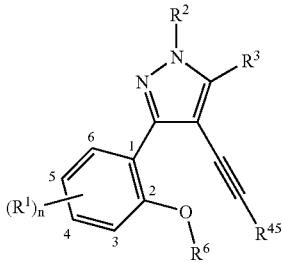

| No. | R¹ | R² | R³ | R⁶ | R⁴⁵ | MW |
|---|---|---|---|---|---|---|
| 23369 | 5-Br | CH₂CH₂OH | H | H | —CH₂S—C₆H₅ | 429.33 |
| 23370 | 5-Br | CH₂CH₂OH | H | H | C(OH)(CH₃)₂-C₆H₅ | 427.29 |
| 23371 | 5-Br | CH₂CH₂OH | H | H | 1-hydroxycyclohexyl | 405.29 |
| 23373 | 4-CH₃ 5-Cl | CH₃ | H | H | 4-methylphenyl | 336.81 |
| 23374 | 4-CH₃ 5-Cl | CH₃ | H | H | 4-methoxyphenyl | 352.81 |
| 23375 | 4-CH₃ 5-Cl | CH₃ | H | H | 4-chlorophenyl | 357.23 |
| 23376 | 4-CH₃ 5-Cl | CH₃ | H | H | cyclohexenyl | 326.82 |
| 23377 | 4-CH₃ 5-Cl | CH₃ | H | H | 2-fluorophenyl | 340.78 |
| 23378 | 4-CH₃ 5-Cl | CH₃ | H | H | CH₃OCOCH(CH₂—)COCH₃ | 390.82 |
| 23379 | 4-CH₃ 5-Cl | CH₃ | H | H | phenyl | 322.79 |

TABLE 1-continued

Table 1 provides representative embodiments for compounds of the formula IV.

| No. | R¹ | R² | R³ | R⁶ | R⁴⁵ | MW |
|---|---|---|---|---|---|---|
| 23380 | 4-CH₃ 5-Cl | CH₃ | H | H | —(CH₂)₃Cl | 323.22 |
| 23381 | 4-CH₃ 5-Cl | CH₃ | H | H | —(CH₂)₃CH₃ | 302.80 |
| 23382 | 4-CH₃ 5-Cl | CH₃ | H | H | —CH₂OCH₃ | 290.74 |
| 23383 | 4-CH₃ 5-Cl | CH₃ | H | H | —C(CH₃)₂OH | 304.77 |
| 23384 | 4-CH₃ 5-Cl | CH₃ | H | H | 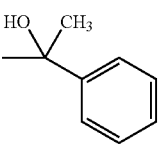 | 368.88 |
| 23385 | 4-CH₃ 5-Cl | CH₃ | H | H | 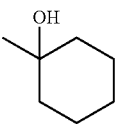 | 366.84 |
| 23386 | 4-CH₃ 5-Cl | CH₃ | H | H | 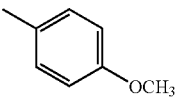 | 344.84 |
| 23387 | 4-CH₃ 5-Cl | CH₂CH₂OH | H | H | 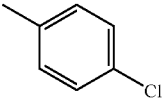 | 382.84 |
| 23388 | 4-CH₃ 5-Cl | CH₂CH₂OH | H | H | 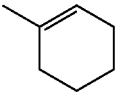 | 387.26 |
| 23389 | 4-CH₃ 5-Cl | CH₂CH₂OH | H | H | 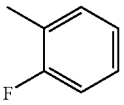 | 356.85 |
| 23390 | 4-CH₃ 5-Cl | CH₂CH₂OH | H | H | —(CH₂)₃CN | 343.81 |
| 23391 | 4-CH₃ 5-Cl | CH₂CH₂OH | H | H | 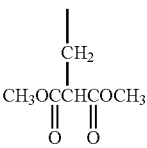 | 370.80 |
| 23392 | 4-CH₃ 5-Cl | CH₂CH₂OH | H | H | CH₃OCCHCOCH₃ (with CH₂ branch, both C=O) | 420.84 |

TABLE 1-continued

Table 1 provides representative embodiments for compounds of the formula IV.

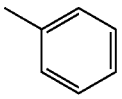

| No. | R¹ | R² | R³ | R⁶ | R⁴⁵ | MW |
|---|---|---|---|---|---|---|
| 23393 | 4-CH₃<br>5-Cl | CH₂CH₂OH | H | H |  | 352.81 |
| 23395 | 4-CH₃<br>5-Cl | CH₂CH₂OH | H | H | —(CH₂)₃Cl | 353.24 |
| 23396 | 4-CH₃<br>5-Cl | CH₂CH₂OH | H | H | —(CH₂)₃CH₃ | 332.82 |
| 23397 | 4-CH₃<br>5-Cl | CH₂CH₂OH | H | H | —CH₂OCH₃ | 320.77 |
| 23398 | 4-CH₃<br>5-Cl | CH₂CH₂OH | H | H | —C(CH₃)₂OH | 334.80 |
| 23399 | 4-CH₃<br>5-Cl | CH₂CH₂OH | H | H | 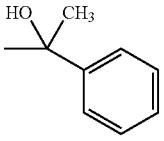 | 398.91 |
| 23400 | 4-CH₃<br>5-Cl | CH₂CH₂OH | H | H | 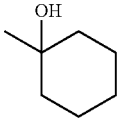 | 396.87 |
| 23401 | 4-CH₃<br>5-Cl | CH₂CH₂OH | H | H | 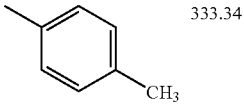 | 374.86 |
| 23402 | 5-NO₂ | CH₃ | H | H | 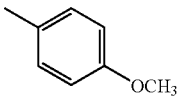 | 333.34 |
| 23403 | 5-NO₂ | CH₃ | H | H | 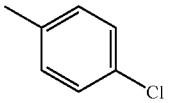 | 349.34 |
| 23404 | 5-NO₂ | CH₃ | H | H | 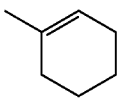 | 353.76 |
| 23405 | 5-NO₂ | CH₃ | H | H |  | 323.35 |
| 23406 | 5-NO₂ | CH₃ | H | H | —(CH₂)₃CN | 310.31 |

TABLE 1-continued

Table 1 provides representative embodiments for compounds of the formula IV.

| No. | R¹ | R² | R³ | R⁶ | R⁴⁵ | MW |
|---|---|---|---|---|---|---|
| 23407 | 5-NO$_2$ | CH$_3$ | H | H | 2-fluorophenyl | 337.30 |
| 23408 | 5-NO$_2$ | CH$_3$ | H | H | CH$_3$OCOCH(CH$_2$—)COCH$_3$ | 387.34 |
| 23409 | 5-NO$_2$ | CH$_3$ | H | H | phenyl | 319.31 |
| 23411 | 5-NO$_2$ | CH$_3$ | H | H | —(CH$_2$)$_3$Cl | 319.74 |
| 23412 | 5-NO$_2$ | CH$_3$ | H | H | —(CH$_2$)$_3$CH$_3$ | 299.32 |
| 23413 | 5-NO$_2$ | CH$_3$ | H | H | —CH$_2$OCH$_3$ | 287.27 |
| 23414 | 5-NO$_2$ | CH$_3$ | H | H | —C(CH$_3$)$_2$OH | 301.30 |
| 23415 | 5-NO$_2$ | CH$_3$ | H | H | —CH$_2$S-phenyl | 365.41 |
| 23416 | 5-NO$_2$ | CH$_3$ | H | H | —C(CH$_3$)(OH)-phenyl | 341.36 |
| 23417 | 5-NO$_2$ | CH$_2$CH$_2$OH | H | H | 4-methylphenyl | 363.37 |
| 23418 | 5-NO$_2$ | CH$_2$CH$_2$OH | H | H | 4-methoxyphenyl | 379.37 |
| 23419 | 5-NO$_2$ | CH$_2$CH$_2$OH | H | H | 4-chlorophenyl | 383.79 |
| 23420 | 5-NO$_2$ | CH$_2$CH$_2$OH | H | H | cyclohexenyl | 353.37 |
| 23421 | 5-NO$_2$ | CH$_2$CH$_2$OH | H | H | —(CH$_2$)$_3$CN | 340.33 |

TABLE 1-continued

Table 1 provides representative embodiments for compounds of the formula IV.

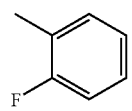

| No. | R¹ | R² | R³ | R⁶ | R⁴⁵ | MW |
|---|---|---|---|---|---|---|
| 23422 | 5-NO$_2$ | CH$_2$CH$_2$OH | H | H | 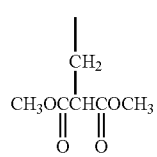 | 367.33 |
| 23423 | 5-NO$_2$ | CH$_2$CH$_2$OH | H | H | 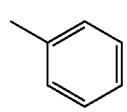 | 417.37 |
| 23424 | 5-NO$_2$ | CH$_2$CH$_2$OH | H | H | 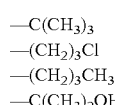 | 349.34 |
| 23425 | 5-NO$_2$ | CH$_2$CH$_2$OH | H | H | —C(CH$_3$)$_3$ | 329.35 |
| 23427 | 5-NO$_2$ | CH$_2$CH$_2$OH | H | H | —(CH$_2$)$_3$Cl | 349.77 |
| 23428 | 5-NO$_2$ | CH$_2$CH$_2$OH | H | H | —(CH$_2$)$_3$CH$_3$ | 329.35 |
| 23429 | 5-NO$_2$ | CH$_2$CH$_2$OH | H | H | —C(CH$_3$)$_2$OH | 331.32 |
| 23430 | 5-NO$_2$ | CH$_2$CH$_2$OH | H | H | 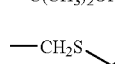 | 395.43 |
| 23431 | 5-NO$_2$ | CH$_2$CH$_2$OH | H | H |  | 371.39 |
| 23432 | — | CH$_2$CH$_2$OH | H | H | 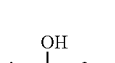 | 318.37 |
| 23433 | — | CH$_2$CH$_2$OH | H | H | 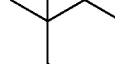 | 334.37 |
| 23434 | — | CH$_2$CH$_2$OH | H | H | 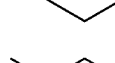 | 338.79 |
| 23435 | — | CH$_2$CH$_2$OH | H | H | 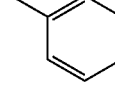 | 308.37 |

TABLE 1-continued
Table 1 provides representative embodiments for compounds of the formula IV.
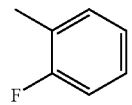
| No. | R¹ | R² | R³ | R⁶ | R⁴⁵ | MW |
|---|---|---|---|---|---|---|
| 23437 | — | CH₂CH₂OH | H | H | 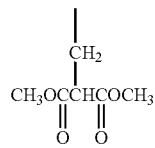 | 322.33 |
| 23438 | — | CH₂CH₂OH | H | H | 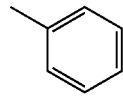 | 372.37 |
| 23439 | — | CH₂CH₂OH | H | H |  | 304.34 |
| 23440 | — | CH₂CH₂OH | H | H | —C(CH₃)₃ | 284.35 |
| 23441 | — | CH₂CH₂OH | H | H | —(CH₂)₃Cl | 304.77 |
| 23442 | — | CH₂CH₂OH | H | H | —(CH₂)₃CH₃ | 284.35 |
| 23443 | — | CH₂CH₂OH | H | H | —OCH₃ | 258.27 |
| 23444 | — | CH₂CH₂OH | H | H | —C(CH₃)₂OH | 286.33 |
| 23445 | — | CH₂CH₂OH | H | H | 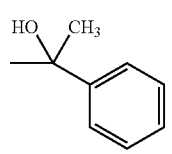 | 250.43 |
| 23446 | — | CH₂CH₂OH | H | H | 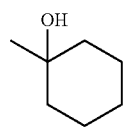 | 348.40 |
| 23447 | — | CH₂CH₂OH | H | H | 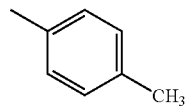 | 326.39 |
| 23448 | 5-CH₃ | CH₂CH₂OH | H | H | 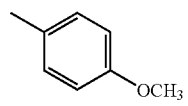 | 332.40 |
| 23449 | 5-CH₃ | CH₂CH₂OH | H | H | 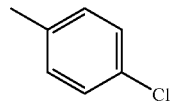 | 348.40 |
| 23450 | 5-CH₃ | CH₂CH₂OH | H | H |  | 352.81 |

TABLE 1-continued

Table 1 provides representative embodiments for compounds of the formula IV.

| No. | R¹ | R² | R³ | R⁶ | R⁴⁵ | MW |
|---|---|---|---|---|---|---|
| 23451 | 5-CH₃ | CH₂CH₂OH | H | H | 1-methylcyclohex-1-enyl | 322.40 |
| 23452 | 5-CH₃ | CH₂CH₂OH | H | H | —(CH₂)₃CN | 309.36 |
| 23453 | 5-CH₃ | CH₂CH₂OH | H | H | 2-fluoro-methylphenyl | 336.36 |
| 23454 | 5-CH₃ | CH₂CH₂OH | H | H | CH₃OCCHCOCH₃ (with CH₂ branch, dimethyl malonate-CH₂—) | 386.40 |
| 23455 | 5-CH₃ | CH₂CH₂OH | H | H | methylphenyl | 318.37 |
| 23456 | 5-CH₃ | CH₂CH₂OH | H | H | —C(CH₃)₃ | 298.38 |
| 23457 | 5-CH₃ | CH₂CH₂OH | H | H | —(CH₂)₃Cl | 318.80 |
| 23458 | 5-CH₃ | CH₂CH₂OH | H | H | —(CH₂)₃CH₃ | 298.38 |
| 23459 | 5-CH₃ | CH₂CH₂OH | H | H | —OCH₃ | 272.30 |
| 23460 | 5-CH₃ | CH₂CH₂OH | H | H | —C(CH₃)₂OH | 300.35 |
| 23461 | 5-CH₃ | CH₂CH₂OH | H | H | —CH₂S-phenyl | 364.46 |
| 23462 | 5-CH₃ | CH₂CH₂OH | H | H | 2-hydroxy-2-phenylpropan-2-yl (HO,CH₃-C-phenyl) | 362.42 |
| 23463 | 5-CH₃ | CH₂CH₂OH | H | H | 1-hydroxy-1-methylcyclohexyl | 340.42 |
| 23464 | 5-Cl | CH₂CH₂OH | H | H | 4-methylphenyl | 352.81 |
| 23465 | 5-Cl | CH₂CH₂OH | H | H | 4-methoxyphenyl | 373.23 |

TABLE 1-continued

Table 1 provides representative embodiments for compounds of the formula IV.

| No. | R¹ | R² | R³ | R⁶ | R⁴⁵ | MW |
|---|---|---|---|---|---|---|
| 23466 | 5-Cl | CH₂CH₂OH | H | H | 1-methylcyclohex-1-enyl | 342.82 |
| 23467 | 5-Cl | CH₂CH₂OH | H | H | —(CH₂)₃CN | 329.78 |
| 23468 | 5-Cl | CH₂CH₂OH | H | H | 2-fluoro-methylphenyl | 356.78 |
| 23469 | 5OCl | CH₂CH₂OH | H | H | CH₃OC(O)CH(CH₂·)C(O)OCH₃ | 406.82 |
| 23470 | 5-Cl | CH₂CH₂OH | H | H | methylphenyl | 338.79 |
| 23471 | 5-Cl | CH₂CH₂OH | H | H | —C(CH₃)₃ | 318.80 |
| 23472 | 5-Cl | CH₂CH₂OH | H | H | —(CH₂)₃Cl | 339.22 |
| 23473 | 5-Cl | CH₂CH₂OH | H | H | —(CH₂)₃CH₃ | 318.80 |
| 23474 | 5-Cl | CH₂CH₂OH | H | H | —OCH₃ | 292.72 |
| 23475 | 5-Cl | CH₂CH₂OH | H | H | —C(CH₃)₂OH | 320.77 |
| 23476 | 5-Cl | CH₂CH₂OH | H | H | —CH₂S-phenyl | 384.88 |
| 23477 | 5-Cl | CH₂CH₂OH | H | H | 2-(hydroxy)(methyl)phenyl | 382.84 |
| 23478 | 5-Cl | CH₂CH₂OH | H | H | 1-hydroxy-1-methylcyclohexyl | 360.83 |
| 23704 | — | CH₃ | H | H | —CH₂O-(2,6-dichlorophenyl) | 373.23 |

TABLE 1-continued

Table 1 provides representative embodiments for compounds of the formula IV.

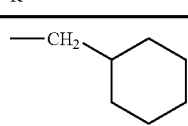

| No. | R¹ | R² | R³ | R⁶ | R⁴⁵ | MW |
|---|---|---|---|---|---|---|
| 23705 | — | CH₃ | H | H | —CH₂–cyclohexyl | 294.39 |
| 23706 | — | CH₃ | H | H | 2-pyridyl-methyl | 275.30 |
| 23707 | — | CH₃ | H | H | 3-pyridyl-methyl | 275.30 |
| 23708 | — | CH₃ | H | H | 4-aminophenyl-methyl | 289.33 |
| 23709 | — | CH₃ | H | H | 3-(CF₃)phenyl-methyl | 342.31 |
| 23710 | 5-CH₃ | CH₃ | H | H | —CH₂O-(2,6-dichlorophenyl) | 387.26 |
| 23711 | 5-CH₃ | CH₃ | H | H | —CH₂–cyclohexyl | 308.42 |
| 23712 | 5-CH₃ | CH₃ | H | H | 2-pyridyl-methyl | 289.33 |
| 23713 | 5-CH₃ | CH₃ | H | H | 3-pyridyl-methyl | 289.33 |
| 23714 | 5-CH₃ | CH₃ | H | H | 4-aminophenyl-methyl | 303.36 |

TABLE 1-continued
Table 1 provides representative embodiments for compounds of the formula IV.
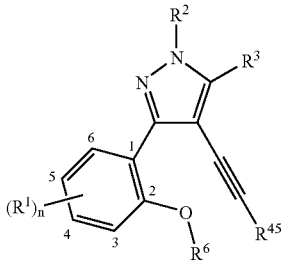
| No. | R¹ | R² | R³ | R⁶ | R⁴⁵ | MW |
|---|---|---|---|---|---|---|
| 23715 | 5-CH₃ | CH₃ | H | H | 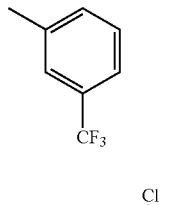 | 356.34 |
| 23716 | 5-Cl | CH₃ | H | H | 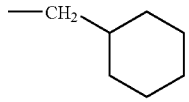 | 407.68 |
| 23717 | 5-Cl | CH₃ | H | H | 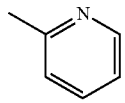 | 328.84 |
| 23718 | 5-Cl | CH₃ | H | H | 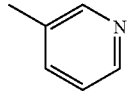 | 309.75 |
| 23719 | 5-Cl | CH₃ | H | H | 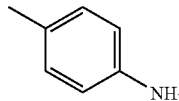 | 309.75 |
| 23720 | 5-Cl | CH₃ | H | H | 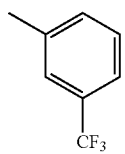 | 323.78 |
| 23721 | 5-Cl | CH₃ | H | H | 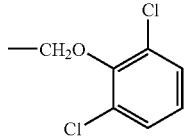 | 376.76 |
| 23722 | — | CH₂CH₂OH | H | H | 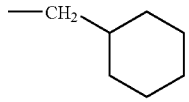 | 403.26 |
| 23723 | — | CH₂CH₂OH | H | H | 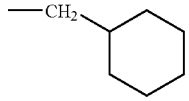 | 324.42 |

TABLE 1-continued

Table 1 provides representative embodiments for compounds of the formula IV.

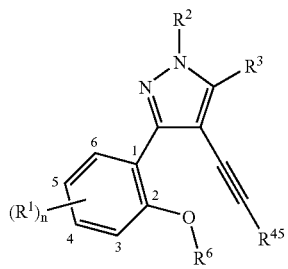

| No. | R¹ | R² | R³ | R⁶ | R⁴⁵ | MW |
|---|---|---|---|---|---|---|
| 23724 | — | CH₂CH₂OH | H | H | 3-pyridyl | 305.33 |
| 23725 | — | CH₂CH₂OH | H | H | 4-aminophenyl | 319.36 |
| 23726 | — | CH₂CH₂OH | H | H | 3-(trifluoromethyl)phenyl | 372.34 |
| 23727 | 5-CH₃ | CH₂CH₂OH | H | H | —CH₂O-(2,6-dichlorophenyl) | 417.29 |
| 23728 | 5-CH₃ | CH₂CH₂OH | H | H | —CH₂-cyclohexyl | 338.44 |
| 23729 | 5-CH₃ | CH₂CH₂OH | H | H | 3-pyridyl | 319.36 |
| 23730 | 5-CH₃ | CH₂CH₂OH | H | H | 3-(trifluoromethyl)phenyl | 386.37 |
| 23731 | 5-Cl | CH₂CH₂OH | H | H | —CH₂O-(2,6-dichlorophenyl) | 437.70 |
| 23732 | 5-Cl | CH₂CH₂OH | H | H | —CH₂-cyclohexyl | 358.86 |

TABLE 1-continued

Table 1 provides representative embodiments for compounds of the formula IV.

| No. | R¹ | R² | R³ | R⁶ | R⁴⁵ | MW |
|---|---|---|---|---|---|---|
| 23733 | 5-Cl | CH₂CH₂OH | H | H | 4-aminophenyl (4-NH₂-C₆H₄-) | 353.80 |
| 23734 | 5-Cl | CH₂CH₂OH | H | H | 3-(trifluoromethyl)phenyl | 406.79 |
| 24679 | — | CH₃ | H | H | 2-hydroxy-2-phenylpropyl (HOC(CH₃)(Ph)-) | 318.37 |
| 24680 | — | CH₃ | H | H | 1-hydroxy-1-methylcyclohexyl | 296.36 |
| 24681 | 5-CH₃ | CH₃ | H | H | 2-hydroxy-2-phenylpropyl | 332.40 |
| 24682 | 5-CH₃ | CH₃ | H | H | 1-hydroxy-1-methylcyclohexyl | 310.39 |
| 24683 | 5-Cl | CH₃ | H | H | 2-hydroxy-2-phenylpropyl | 352.81 |
| 24684 | 5-Cl | CH₃ | H | H | 1-hydroxy-1-methylcyclohexyl | 330.81 |
| 24685 | 4-CH₃, 5-Cl | CH₃ | H | H | —C(CH₃)₃ | 302.80 |
| 24686 | 4-CH₃, 5-Cl | CH₂CH₂OH | H | H | —C(CH₃)₃ | 332.82 |
| 24687 | 5-Br | CH₃ | H | H | —C(CH₃)₃ | 333.22 |
| 24688 | 5-Br | CH₂CH₂OH | H | H | —C(CH₃)₃ | 363.25 |

TABLE 1-continued
Table 1 provides representative embodiments for compounds of the formula IV.
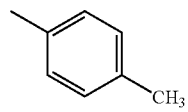
| No. | R¹ | R² | R³ | R⁶ | R⁴⁵ | MW |
|---|---|---|---|---|---|---|
| 24689 | 5-NO$_2$ | CH$_3$ | H | H | —C(CH$_3$)$_3$ | 299.32 |
| 24691 | 4-CH$_3$ 5-Cl | CH$_3$ | H | H | —(CH$_2$)$_3$CN | 313.78 |
| 24692 | 4-CH$_3$ 5-Cl | CH$_2$CH$_2$OH | H | H | 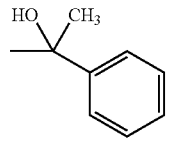 | 366.84 |
| 24695 | 5-NO$_2$ | CH$_3$ | H | H | 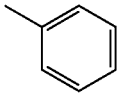 | 363.37 |
| 24697 | 5-NO$_2$ | CH$_2$CH$_2$OH | H | H | —CH$_2$OCH$_3$ | 317.30 |
| 25058 | — | CH$_3$ | 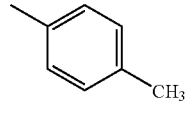 | H | 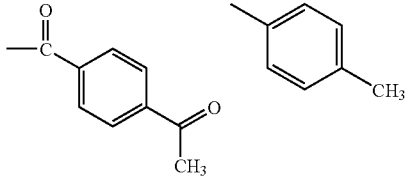 | 364.44 |
| 25059 | — | CH$_3$ | H | 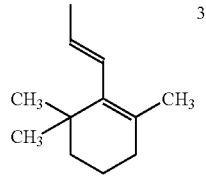 | 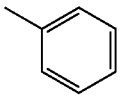 | 434.49 |
| 26558 | — | CH$_3$ | H | H | 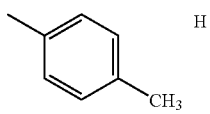 | 346.47 |
| 27058 | — | CH$_3$ | H | H | —(CH$_2$)$_3$C(=NH)NH$_2$ | 282.34 |
| 30716 | — | CH$_3$ |  | H | —(CH$_2$)$_3$CN | 341.41 |
| 33471 | 5-NO$_2$ |  | H | H | —C(CH$_3$)$_3$ | 375.42 |

TABLE 1-continued
Table 1 provides representative embodiments for compounds of the formula IV.
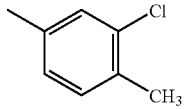
| No. | R¹ | R² | R³ | R⁶ | R⁴⁵ | MW |
|---|---|---|---|---|---|---|
| 33472 | 5-NO$_2$ | 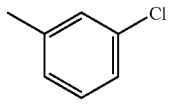 | H | H | —C(CH$_3$)$_3$ | 409.87 |
| 33474 | 5-NO$_2$ | 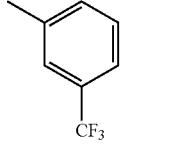 | H | H | —C(CH$_3$)$_3$ | 395.84 |
| 33475 | 5-NO$_2$ | 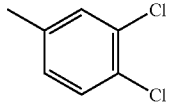 | H | H | —C(CH$_3$)$_3$ | 429.40 |
| 33476 | 5-NO$_2$ | 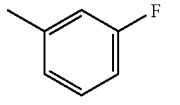 | H | H | —C(CH$_3$)$_3$ | 430.29 |
| 33478 | 5-NO$_2$ | 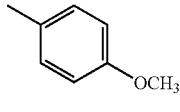 | H | H | —C(CH$_3$)$_3$ | 379.39 |
| 33481 | 5-NO$_2$ | 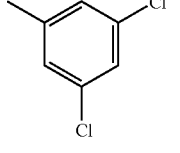 | H | H | —C(CH$_3$)$_3$ | 391.43 |
| 33482 | 5-NO$_2$ | 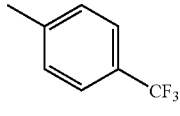 | H | H | —C(CH$_3$)$_3$ | 430.29 |
| 33486 | 5-NO$_2$ |  | H | H | —C(CH$_3$)$_3$ | 429.40 |
| 33487 | 5-NO$_2$ |  | H | H | —C(CH$_3$)$_3$ | 397.38 |
| 33508 | 5-NO$_2$ | CH$_3$ | H | —CH$_2$CO$_2$H | —C(CH$_3$)$_3$ | 357.36 |
| 33513 | 5-Br | CH$_3$ | H | —CH$_2$CO$_2$Et | —(CH$_2$)$_3$CN | 430.30 |

TABLE 1-continued

Table 1 provides representative embodiments for compounds of the formula IV.

| No. | R¹ | R² | R³ | R⁶ | R⁴⁵ | MW |
|---|---|---|---|---|---|---|
| 33514 | 5-Br | CH₃ | H | —CH₂-(3,4-diCl-phenyl) | —(CH₂)₃CN | 503.22 |
| 33515 | 5-NO₂ | CH₃ | H | —C(O)C≡CCH₃ | —C(CH₃)₃ | 365.38 |
| 33516 | 5-NO₂ | CH₃ | H | —CH₂-(4-C(CH₃)₃-phenyl) | —C(CH₃)₃ | 455.55 |
| 33517 | 5-NO₂ | CH₃ | H | —CH₂-(3,5-diCl-phenyl) | —C(CH₃)₃ | 458.34 |
| 33518 | 5-NO₂ | CH₃ | H | —CH₂-(3,5-diF-phenyl) | —C(CH₃)₃ | 425.43 |
| 33519 | 5-NO₂ | CH₃ | H | —CH₂-(3,4-diCl-phenyl) | —C(CH₃)₃ | 458.34 |
| 33520 | 5-NO₂ | CH₃ | H | —CH₂-(2,3-diF-phenyl) | —C(CH₃)₃ | 425.43 |
| 33521 | 5-NO₂ | CH₃ | H | —CH₂-(2-Cl-4-F-phenyl) | —C(CH₃)₃ | 441.88 |
| 33522 | 5-NO₂ | CH₃ | H | —CH₂-(2-Cl-phenyl) | —C(CH₃)₃ | 423.89 |

TABLE 1-continued

Table 1 provides representative embodiments for compounds of the formula IV.

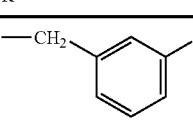

| No. | R¹ | R² | R³ | R⁶ | R⁴⁵ | MW |
|---|---|---|---|---|---|---|
| 33523 | 5-NO$_2$ | CH$_3$ | H | —CH$_2$—(3-Cl-C$_6$H$_4$) | —C(CH$_3$)$_3$ | 423.89 |
| 33524 | 5-NO$_2$ | CH$_3$ | H | —CH$_2$—(2,3,5,6-tetrafluorophenyl) | —C(CH$_3$)$_3$ | 461.41 |
| 33525 | 5-NO$_2$ | CH$_3$ | H | —CH$_2$—(2-NO$_2$-C$_6$H$_4$) | —C(CH$_3$)$_3$ | 434.44 |
| 33526 | 5-NO$_2$ | CH$_3$ | H | —CH$_2$—(3-NO$_2$-C$_6$H$_4$) | —C(CH$_3$)$_3$ | 434.44 |
| 33527 | 5-NO$_2$ | CH$_3$ | H | —CH$_2$—(2-CN-C$_6$H$_4$) | —C(CH$_3$)$_3$ | 414.46 |
| 33528 | 5-NO$_2$ | CH$_3$ | H | —CH$_2$—(3-CN-C$_6$H$_4$) | —C(CH$_3$)$_3$ | 414.46 |
| 33529 | 5-NO$_2$ | CH$_3$ | H | —CH$_2$—(4-CN-C$_6$H$_4$) | —C(CH$_3$)$_3$ | 414.46 |
| 33530 | 5-NO$_2$ | CH$_3$ | H | —CH$_2$—(2-CF$_3$-C$_6$H$_4$) | —C(CH$_3$)$_3$ | 457.44 |
| 33531 | 5-NO$_2$ | CH$_3$ | H | —CH$_2$—(2-CH$_3$-C$_6$H$_4$) | —C(CH$_3$)$_3$ | 403.47 |
| 33532 | 5-NO$_2$ | CH$_3$ | H | —CH$_2$—(3-CH$_3$-C$_6$H$_4$) | —C(CH$_3$)$_3$ | 403.47 |

TABLE 1-continued

Table 1 provides representative embodiments for compounds of the formula IV.

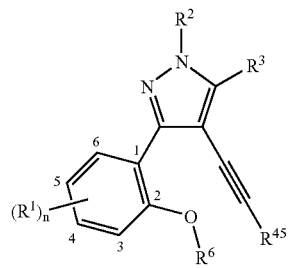

| No. | $R^1$ | $R^2$ | $R^3$ | $R^6$ | $R^{45}$ | MW |
|---|---|---|---|---|---|---|
| 33533 | 5-NO$_2$ | CH$_3$ | H | —CH$_2$—C$_6$H$_4$—CH$_3$ (4-CH$_3$) | —C(CH$_3$)$_3$ | 403.47 |
| 33534 | 5-NO$_2$ | CH$_3$ | H | —CH$_2$—C$_6$H$_3$(CH$_3$)$_2$ (3,5-(CH$_3$)$_2$) | —C(CH$_3$)$_3$ | 417.50 |
| 33535 | 5-NO$_2$ | CH$_3$ | H | —CH$_2$—C$_6$H$_5$ | —C(CH$_3$)$_3$ | 389.45 |
| 33536 | 5-NO$_2$ | CH$_3$ | H | —CH$_2$—C$_6$H$_4$—F (2-F) | —C(CH$_3$)$_3$ | 407.44 |
| 33537 | 5-NO$_2$ | CH$_3$ | H | —CH$_2$—C$_6$H$_4$—F (4-F) | —C(CH$_3$)$_3$ | 407.44 |
| 33538 | 5-NO$_2$ | CH$_3$ | H | —CH$_2$—C$_6$H$_3$F$_2$ (2,4-F$_2$) | —C(CH$_3$)$_3$ | 425.43 |
| 33539 | 5-NO$_2$ | CH$_3$ | H | —CH$_2$—C$_6$F$_5$ | —C(CH$_3$)$_3$ | 479.40 |
| 33540 | 5-NO$_2$ | CH$_3$ | H | —CH$_2$—C$_6$HF$_4$ | —C(CH$_3$)$_3$ | 461.41 |

TABLE 1-continued
Table 1 provides representative embodiments for compounds of the formula IV.
| No. | R¹ | R² | R³ | R⁶ | R⁴⁵ | MW |
|---|---|---|---|---|---|---|
| 33541 | 5-NO$_2$ | CH$_3$ | H |  | —C(CH$_3$)$_3$ | 447.48 |
| 33542 | 5-NO$_2$ | CH$_3$ | H |  | —C(CH$_3$)$_3$ | 457.44 |
| 33543 | 5-NO$_2$ | CH$_3$ | H | 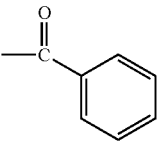 | —C(CH$_3$)$_3$ | 473.44 |
| 33638 | 5-NO$_2$ | CH$_3$ | H | —CH$_2$CO$_2$Et | —C(CH$_3$)$_3$ | 385.41 |
| 33674 | 5-NO$_2$ | CH$_3$ | H | 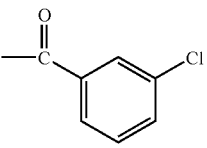 | —C(CH$_3$)$_3$ | 403.43 |
| 33675 | 5-NO$_2$ | CH$_3$ | H | 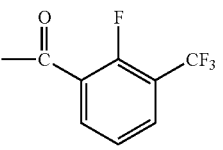 | —C(CH$_3$)$_3$ | 437.88 |
| 33676 | 5-NO$_2$ | CH$_3$ | H | 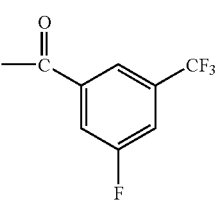 | —C(CH$_3$)$_3$ | 489.42 |
| 33677 | 5-NO$_2$ | CH$_3$ | H |  | —C(CH$_3$)$_3$ | 489.42 |

TABLE 1-continued
Table 1 provides representative embodiments for compounds of the formula IV.
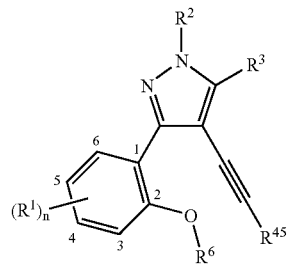
| No. | R¹ | R² | R³ | R⁶ | R⁴⁵ | MW |
|---|---|---|---|---|---|---|
| 33678 | 5-NO$_2$ | CH$_3$ | H | ![](3-F,4-CF$_3$ benzoyl) | —C(CH$_3$)$_3$ | 489.42 |
| 33679 | 5-NO$_2$ | CH$_3$ | H | ![](2-F,4-CF$_3$ benzoyl) | —C(CH$_3$)$_3$ | 489.42 |
| 33680 | 5-NO$_2$ | CH$_3$ | H | ![](3-CF$_3$ benzoyl) | —C(CH$_3$)$_3$ | 471.43 |
| 33681 | 5-NO$_2$ | CH$_3$ | H | ![](2-CF$_3$,6-F benzoyl) | —C(CH$_3$)$_3$ | 489.42 |
| 33682 | 5-NO$_2$ | CH$_3$ | H | $_6$CH$_3$ benzoyl) | —C(CH$_3$)$_3$ | 517.62 |
| 33683 | 5-NO$_2$ | CH$_3$ | H | ![](2,5-bis-CF$_3$ benzoyl) | —C(CH$_3$)$_3$ | 639.43 |
| 33684 | 5-NO$_2$ | CH$_3$ | H | ![](2-F,5-CF$_3$ benzoyl) | —C(CH$_3$)$_3$ | 489.42 |

TABLE 1-continued

Table 1 provides representative embodiments for compounds of the formula IV.

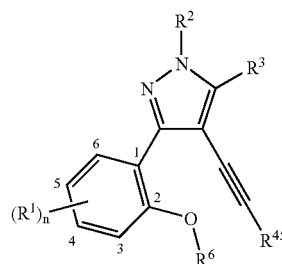

| No. | $R^1$ | $R^2$ | $R^3$ | $R^6$ | $R^{45}$ | MW |
|---|---|---|---|---|---|---|
| 33685 | 5-$NO_2$ | $CH_3$ | H | ![3-cyanobenzoyl] | —C(CH$_3$)$_3$ | 428.44 |
| 33686 | 5-$NO_2$ | $CH_3$ | H | ![3,5-bis(trifluoromethyl)benzoyl] | —C(CH$_3$)$_3$ | 539.43 |
| 33687 | 5-$NO_2$ | $CH_3$ | H | ![2-(trifluoromethyl)benzoyl] | —C(CH$_3$)$_3$ | 471.43 |
| 34141 | 5-Br | $CH_3$ | H | H | —C(CH$_3$)$_3$ | 361.24 |
| 34142 | 5-$NH_2$ | $CH_3$ | H | H | —C(CH$_3$)$_3$ | 269.35 |
| 34144 | 5-Br | $CH_3$ | —CH=N—NH—C(O)—C$_6$H$_5$ | H | —C(CH$_3$)$_3$ | 480.36 |
| 34145 | 5-$OCH_3$ | $CH_3$ | H | H | —C(CH$_3$)$_3$ | 284.36 |
| 34146 | 5-Br | $CH_3$ | —C(O)N(CH$_3$)$_2$ | H | —C(CH$_3$)$_3$ | 404.31 |
| 34147 | 5-Br | $CH_3$ | H | —C(O)CH$_3$ | —C(CH$_3$)$_3$ | 375.26 |
| 34148 | 5- —C≡CHCO$_2$CH$_3$ | $CH_3$ | H | H | —C(CH$_3$)$_3$ | 338.41 |
| 34177 | 5- —NHSO$_2$CH$_3$ | $CH_3$ | H | H | —C(CH$_3$)$_3$ | 347.43 |
| 34178 | 5- —NH—SO$_2$—(4-methylphenyl) | $CH_3$ | H | H | —C(CH$_3$)$_3$ | 423.53 |
| 34179 | 5- —NH—SO$_2$—(2-oxo-2H-chromen-4-yl) | $CH_3$ | H | H | —C(CH$_3$)$_3$ | 477.53 |

TABLE 1-continued

Table 1 provides representative embodiments for compounds of the formula IV.

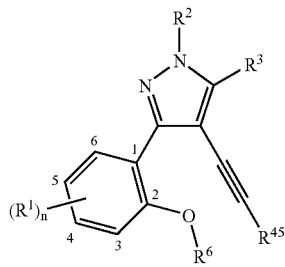

| No. | R¹ | R² | R³ | R⁶ | R⁴⁵ | MW |
|---|---|---|---|---|---|---|
| 34180 | 5- —CH=CHCO₂H | CH₃ | H | H | —C(CH₃)₃ | 324.38 |
| 34227 | 5-NO₂ | CH₃ | H | H | 3-pyridyl | 320.31 |
| 34228 | 5-NO₂ | CH₃ | H | H | 4-aminophenyl | 334.33 |
| 34229 | 4-CH₃ 5-Cl | CH₃ | H | H | 3-pyridyl | 323.78 |
| 34230 | 4-CH₃ 5-Cl | CH₃ | H | H | 4-aminophenyl | 337.81 |
| 34231 | 4-CH₃ 5-Cl | —CH₂CH₂OH | H | H | 3-pyridyl | 353.81 |
| 34232 | 4-CH₃ 5-Cl | —CH₂CH₂OH | H | H | 4-aminophenyl | 367.83 |
| 34233 | 5-CH₃ | —CH₂CH₂OH | H | H | 4-aminophenyl | 333.39 |
| 34234 | 5-Cl | —CH₂CH₂OH | H | H | 3-pyridyl | 339.78 |
| 34235 | 5-Br | —CH₃ | H | H | 3-pyridyl | 354.20 |
| 34236 | 5-Br | —CH₃ | H | H | 4-aminophenyl | 368.23 |

TABLE 1-continued

Table 1 provides representative embodiments for compounds of the formula IV.

| No. | R[1] | R[2] | R[3] | R[6] | R[45] | MW |
|---|---|---|---|---|---|---|
| 34237 | 5-Br | —CH$_2$CH$_2$OH | H | H | 4-aminophenyl (p-methylaniline) | 398.26 |
| 34238 | 5-Br | —CH$_2$CH$_2$OH | H | H | 3-pyridyl (methylpyridine) | 384.23 |
| 34295 | 5-—C≡C(CH$_2$)$_3$CN | —CH$_3$ | H | H | —C(CH$_3$)$_3$ | 345.44 |
| 34297 | 5-Br | —CH$_3$ | 2-fluoro-4,5-dimethylphenyl | H | —C(CH$_3$)$_3$ | 441.34 |
| 34298 | 5-Br | —CH$_3$ | —(CH$_2$)$_3$CN | H | —C(CH$_3$)$_3$ | 424.34 |
| 34300 | 5-Br | —CH$_3$ | I | H | —C(CH$_3$)$_3$ | 459.12 |
| 34302 | —NH-C(O)-(3-CF$_3$-phenyl) | —CH$_3$ | H | H | —C(CH$_3$)$_3$ | 441.45 |
| 34303 | —NH-C(O)-(2,5-bis-CF$_3$-phenyl) | —CH$_3$ | H | H | —C(CH$_3$)$_3$ | 509.45 |
| 34304 | —NH-C(O)-(3,5-bis-CF$_3$-phenyl) | —CH$_3$ | H | H | —C(CH$_3$)$_3$ | 509.45 |
| 34305 | —NH-C(O)-(2-F-3-CF$_3$-phenyl) | —CH$_3$ | H | H | —C(CH$_3$)$_3$ | 459.44 |

TABLE 1-continued
Table 1 provides representative embodiments for compounds of the formula IV.
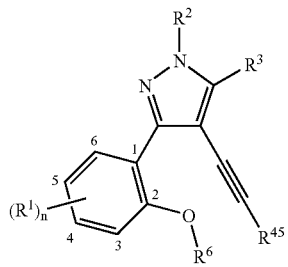
| No. | R¹ | R² | R³ | R⁶ | R⁴⁵ | MW |
|---|---|---|---|---|---|---|
| 34306 | 2-F, 4-CF₃ benzamide | —CH₃ | H | H | —C(CH₃)₃ | 459.44 |
| 34307 | 2-F, 5-CF₃ benzamide | —CH₃ | H | H | —C(CH₃)₃ | 459.44 |
| 34308 | 2-CF₃, 6-F benzamide | —CH₃ | H | H | —C(CH₃)₃ | 459.44 |
| 34309 | 3-F, 4-CF₃ benzamide | —CH₃ | H | H | —C(CH₃)₃ | 459.44 |
| 34310 | 3-F, 5-CF₃ benzamide | —CH₃ | H | H | —C(CH₃)₃ | 459.44 |
| 34311 | camphanoyl amide | —CH₃ | H | H | —C(CH₃)₃ | 449.54 |

TABLE 1-continued

Table 1 provides representative embodiments for compounds of the formula IV.

| No. | R¹ | R² | R³ | R⁶ | R⁴⁵ | MW |
|---|---|---|---|---|---|---|
| 34392 | —C≡C—(2-chlorophenyl) | —CH₃ | H | H | —C(CH₃)₃ | 388.90 |
| 34393 | —C≡C—(4-methoxyphenyl) | —CH₃ | H | H | —C(CH₃)₃ | 384.48 |
| 34394 | —C≡C—(4-chlorophenyl) | —CH₃ | H | H | —C(CH₃)₃ | 388.90 |
| 34395 | —C≡CCH₂—phenyl | —CH₃ | H | H | —C(CH₃)₃ | 374.52 |
| 34396 | —C≡CC(CH₃)₂OH | —CH₃ | H | H | —C(CH₃)₃ | 336.43 |
| 34397 | —C≡CCH₂S—phenyl | —CH₃ | H | H | —C(CH₃)₃ | 400.54 |
| 34398 | —C≡C—(1-hydroxycyclohexyl) | —CH₃ | H | H | —C(CH₃)₃ | 376.50 |
| 34399 | —C≡C—cyclopropyl | —CH₃ | H | H | —C(CH₃)₃ | 318.42 |
| 34401 | —C≡CCH(OH)CH(CH₃)(CH₂)₂CH₃ | —CH₃ | H | H | —C(CH₃)₃ | 378.51 |

TABLE 1-continued

Table 1 provides representative embodiments for compounds of the formula IV.

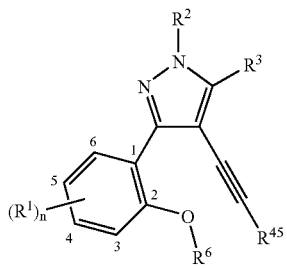

| No. | R¹ | R² | R³ | R⁶ | R⁴⁵ | MW |
|---|---|---|---|---|---|---|
| 34402 | —C≡CCH(OH)CH₂CHCH₃ with CH₃ branch | —CH₃ | H | H | —C(CH₃)₃ | 364.49 |
| 34403 | —C≡C-(1-hydroxycyclopentyl) | —CH₃ | H | H | —C(CH₃)₃ | 362.47 |
| 34404 | —C≡CC(OH)(CH(CH₃)₂)CH(CH₃)₂ | —CH₃ | H | H | —C(CH₃)₃ | 392.54 |
| 34405 | —C≡C-(2-chlorophenyl) | —CH₂CH₂OH | H | H | —C(CH₃)₃ | 418.92 |
| 34406 | —C≡C-(4-methoxyphenyl) | —CH₂CH₂OH | H | H | —C(CH₃)₃ | 414.50 |
| 34407 | —C≡C-(4-chlorophenyl) | —CH₂CH₂OH | H | H | —C(CH₃)₃ | 418.92 |
| 34408 | —C≡C-(cyclohex-1-enyl) | —CH₂CH₂OH | H | H | —C(CH₃)₃ | 388.51 |
| 34409 | —C≡CC(CH₃)₃ | —CH₂CH₂OH | H | H | —C(CH₃)₃ | 364.49 |

TABLE 1-continued

Table 1 provides representative embodiments for compounds of the formula IV.

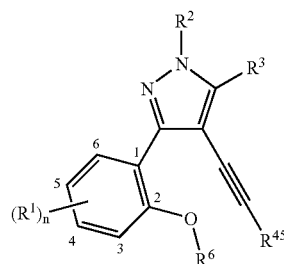

| No. | R¹ | R² | R³ | R⁶ | R⁴⁵ | MW |
|---|---|---|---|---|---|---|
| 34410 | —C≡CCH₂-cyclohexyl | —CH₂CH₂OH | H | H | —C(CH₃)₃ | 404.55 |
| 34411 | —C≡C-(3-pyridyl) | —CH₂CH₂OH | H | H | —C(CH₃)₃ | 385.46 |
| 34412 | —C≡C(CH₂)₃CN | —CH₂CH₂OH | H | H | —C(CH₃)₃ | 375.47 |
| 34413 | —C≡CCH₂OCH₃ | —CH₂CH₂OH | H | H | —C(CH₃)₃ | 352.43 |
| 34414 | —C≡CC(CH₃)₂OH | —CH₂CH₂OH | H | H | —C(CH₃)₃ | 366.46 |
| 34415 | —C≡C-(1-hydroxycyclohexyl) | —CH₂CH₂OH | H | H | —C(CH₃)₃ | 406.52 |
| 34416 | —C≡C-cyclopropyl | —CH₂CH₂OH | H | H | —C(CH₃)₃ | 348.44 |
| 34417 | —C≡C—C(OH)(phenyl)₂ | —CH₂CH₂OH | H | H | —C(CH₃)₃ | 490.60 |
| 34419 | —C≡CCH(OH)CH(CH₃)(CH₂)₂CH₃ | —CH₂CH₂OH | H | H | —C(CH₃)₃ | 408.54 |
| 34420 | —C≡CCH(OH)CH₂CH(CH₃)CH₃ | —CH₂CH₂OH | H | H | —C(CH₃)₃ | 394.51 |
| 34421 | —C≡C-(1-hydroxycyclopentyl) | —CH₂CH₂OH | H | H | —C(CH₃)₃ | 392.50 |
| 34422 | —C≡CC(OH)(CH(CH₃)₂)(CH(CH₃)₂) | —CH₂CH₂OH | H | H | —C(CH₃)₃ | 422.57 |

TABLE 1-continued

Table 1 provides representative embodiments for compounds of the formula IV.

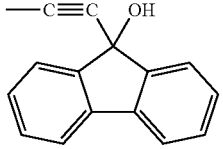

| No. | R¹ | R² | R³ | R⁶ | R⁴⁵ | MW |
|---|---|---|---|---|---|---|
| 34423 | —C≡C—C(OH)(fluorenyl)  | —CH₂CH₂OH | H | H | —C(CH₃)₃ | 488.58 |
| 34424 | 5-NO₂ | —CH₃ | H | H | cyclopropyl | 283.29 |
| 34425 | 5-NO₂ | —CH₂CH₂OH | H | H | cyclopropyl | 313.31 |
| 34426 | 4-CH₃ 5-Cl | —CH₃ | H | H | cyclopropyl | 286.76 |
| 34427 | 4-CH₃ 5-Cl | —CH₂CH₂OH | H | H | cyclopropyl | 316.78 |
| 34428 | 5-CH₃ | —CH₃ | H | H | cyclopropyl | 252.32 |
| 34429 | 5-CH₃ | —CH₂CH₂OH | H | H | cyclopropyl | 282.34 |
| 34430 | 5-Cl | —CH₃ | H | H | cyclopropyl | 272.73 |
| 34431 | 5-Cl | —CH₂CH₂OH | H | H | cyclopropyl | 302.76 |
| 34432 | 5-Br | —CH₃ | H | H | cyclopropyl | 317.18 |
| 34433 | 5-Br | —CH₂CH₂OH | H | H | cyclopropyl | 347.21 |
| 34434 | 4-CH₃ 5-F | —CH₃ | H | H | cyclopropyl | 270.31 |
| 34435 | 4-CH₃ 5-F | —CH₂CH₂OH | H | H | cyclopropyl | 300.33 |
| 34436 | 5-(2-F-3-CH₃-phenyl)  | —CH₃ | H | H | —C(CH₃)₃ | 362.45 |
| 34927 | 3-NO₂ 5-NO₂ | —CH₃ | H | H | —C(CH₃)₃ | 344.33 |
| 34928 | 3-NO₂ 5-Br | —CH₃ | H | H | —C(CH₃)₃ | 378.22 |

TABLE 1-continued
Table 1 provides representative embodiments for compounds of the formula IV.
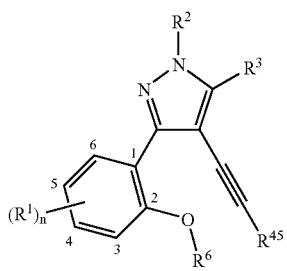
| No. | R¹ | R² | R³ | R⁶ | R⁴⁵ | MW |
|---|---|---|---|---|---|---|
| 35030 | 5- | —CH₃ | H | H | —C(CH₃)₃ | 365.47 |
| 35031 | 5- | —CH₃ | H | H | —C(CH₃)₃ | 348.42 |
| 35036 | 5- | —CH₃ | H | H | —C(CH₃)₃ | 346.43 |
| 35528 | 5- | —CH₃ | H | H | —C(CH₃)₃ | 374.44 |
| 35529 | 5- | —CH₃ | H | H | —C(CH₃)₃ | 345.44 |
| 35530 | 5- | —CH₃ | H | H | —C(CH₃)₃ | 355.44 |
| 35531 | 5- | —CH₃ | H | H | —C(CH₃)₃ | 344.46 |
| 35532 | 5- | —CH₃ | H | H | —C(CH₃)₃ | 386.51 |

TABLE 1-continued
Table 1 provides representative embodiments for compounds of the formula IV.
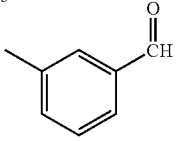
| No. | R¹ | R² | R³ | R⁶ | R⁴⁵ | MW |
|---|---|---|---|---|---|---|
| 35533 | 5- 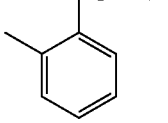 | —CH₃ | H | H | —C(CH₃)₃ | 358.44 |
| 35534 | 5- 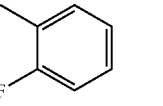 | —CH₃ | H | H | —C(CH₃)₃ | 465.61 |
| 35535 | 5- 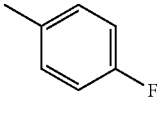 | —CH₃ | H | H | —C(CH₃)₃ | 348.42 |
| 35536 | 5- 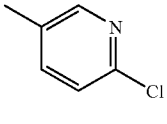 | —CH₃ | H | H | —C(CH₃)₃ | 348.42 |
| 35537 | 5- 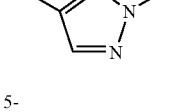 | —CH₃ | H | H | —C(CH₃)₃ | 365.86 |
| 35538 | 5- 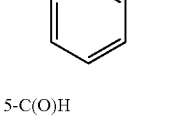 | —CH₃ | H | H | —C(CH₃)₃ | 334.42 |
| 35539 | 5- 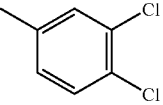 | —CH₃ | H | H | —C(CH₃)₃ | 330.43 |
| 35540 | 5-C(O)H | —CH₃ | H | H | —C(CH₃)₃ | 282.34 |
| 35541 | 5-  | —CH₃ | H | H | —C(CH₃)₃ | 399.32 |

TABLE 1-continued
Table 1 provides representative embodiments for compounds of the formula IV.
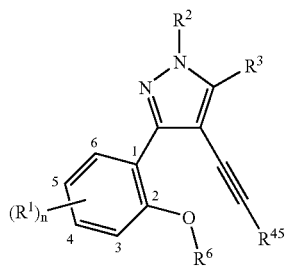
| No. | R¹ | R² | R³ | R⁶ | R⁴⁵ | MW |
|---|---|---|---|---|---|---|
| 35542 | 5- (4-hydroxyphenyl) | —CH₃ | H | H | —C(CH₃)₃ | 346.43 |
| 35543 | 5- (3-chlorophenyl) | —CH₃ | H | H | —C(CH₃)₃ | 364.87 |
| 35544 | 5- (4-methoxyphenyl) | —CH₃ | H | H | —C(CH₃)₃ | 360.45 |
| 35545 | 5- (naphthalen-1-yl) | —CH₃ | H | H | —C(CH₃)₃ | 380.49 |
| 35546 | 5- (naphthalen-2-yl) | —CH₃ | H | H | —C(CH₃)₃ | 380.49 |
| 35547 | 5- (thianthrenyl) | —CH₃ | H | H | —C(CH₃)₃ | 468.63 |

TABLE 1-continued

Table 1 provides representative embodiments for compounds of the formula IV.

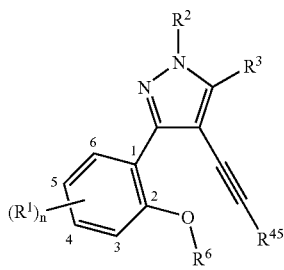

| No. | R¹ | R² | R³ | R⁶ | R⁴⁵ | MW |
|---|---|---|---|---|---|---|
| 35548 | 5- (4-methyldibenzofuran) | —CH₃ | H | H | —C(CH₃)₃ | 420.51 |
| 35549 | 5- (2-methoxy-methylphenyl) | —CH₃ | H | H | —C(CH₃)₃ | 360.45 |
| 35550 | 5- (2-methoxy-4-fluoro-methylphenyl) | —CH₃ | H | H | —C(CH₃)₃ | 378.45 |
| 35551 | 5- (3-methylpyridin) | —CH₃ | H | H | —C(CH₃)₃ | 331.42 |
| 35552 | 5- (4-chloro-2,5-difluoro-methylphenyl) | —CH₃ | H | H | —C(CH₃)₃ | 400.85 |
| 35553 | 5- (2,3-difluoro-methylphenyl) | —CH₃ | H | H | —C(CH₃)₃ | 366.41 |
| 35554 | 5- (2,3-difluoro-methylpyridin) | —CH₃ | H | H | —C(CH₃)₃ | 400.31 |

TABLE 1-continued

Table 1 provides representative embodiments for compounds of the formula IV.

| No. | R¹ | R² | R³ | R⁶ | R⁴⁵ | MW |
|---|---|---|---|---|---|---|
| 35555 | 5- (4-methyl-1H-pyrazol-3-yl) | —CH$_3$ | H | H | —C(CH$_3$)$_3$ | 320.39 |
| 35556 | 5- (N-(3,4-dichlorophenyl)carboxamide) | —CH$_3$ | H | H | —C(CH$_3$)$_3$ | 442.34 |
| 35557 | 5- (morpholin-4-ylcarbonyl) | —CH$_3$ | H | H | —C(CH$_3$)$_3$ | 367.45 |
| 35558 | 5- (N-(2-chlorophenyl)carboxamide) | —CH$_3$ | H | H | —C(CH$_3$)$_3$ | 407.90 |
| 35559 | 5- (N-(3-chlorophenyl)carboxamide) | —CH$_3$ | H | H | —C(CH$_3$)$_3$ | 407.90 |
| 35560 | 5- (N-cyclohexylcarboxamide) | —CH$_3$ | H | H | —C(CH$_3$)$_3$ | 379.50 |
| 35569 | 5-CO$_2$H | —CH$_3$ | H | H | —C(CH$_3$)$_3$ | 298.34 |

In a preferred embodiment of the invention, $R^2$ of the compound according to the formula IV is selected to be methyl and $R^6$ is selected to be H to give a compound having the formula V:

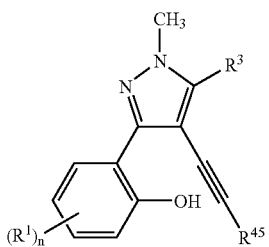

(V)

wherein:
each $R^1$ is independently selected from alkyl, alkenyl, alkynyl, aralkyl, —O—$R^{11}$, —N($R^{12}$)($R^{13}$), —N($R^{11}$)C(O) $R^{11}$, —N($R^{11}$)SO$_2$$R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3$$R^{11}$, —SO$_2$N($R^{12}$) ($R^{13}$), -alkyl-O—$R^{11}$, cycloalkyl, cycloalkenyl, halo, aryl and heteroaryl;
additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;
each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom,
n is 0 to 4;
$R^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)$R^{31}$, —C(O)O$R^{31}$, —C(O)N($R^{32}$)($R^{33}$);
$R^{31}$ is selected from H, alkyl, alkyl-O-alkyl, alkyl-O-aryl, alkenyl, alkynyl, cycloalkyl, cycloalkenyl, aralkyl, aryl and heteroaryl;
$R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, NO$_2$, CO$_2$$R^{34}$, C(O)$R^{34}$, —O—$R^{34}$, —N($R^{34}$)($R^{35}$), —N($R^{34}$)C(O)$R^{34}$, —N($R^{34}$)SO$_2$$R^{34}$, —S$R^{34}$, —C(O) N($R^{35}$)($R^{36}$), —OC(O)$R^{34}$, —OC(O)N($R^{35}$)($R^{36}$), SO$_2$, —SO$R^{34}$, —SO$_3$$R^{34}$, —SO$_2$N($R^{35}$)($R^{36}$), halo, cycloalkyl, cycloalkenyl, aryl and heteroaryl;
each $R^{34}$ is independently selected from H, alkyl, cycloalkyl, cycloalkeneyl, alkenyl, alkynyl, aralkyl, aryl and heteroaryl;
each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;
$R^{45}$ is selected from H, alkyl, -alkyl-O-alkyl, -alkyl-O-aryl, aryl, aralkyl, cycloalkyl, cycloalkenyl, and —(CH$_2$)$_a$—$R^{42}$;
$R^{42}$ is selected from —N($R^{421}$)C(O)$R^{421}$, —N($R^{42}$)SO$_2$$R^{421}$, —O$R^{421}$, —S$R^{421}$, —C(O)$R^{421}$, —C(O)O$R^{421}$, —C(O) N$^{422}$)($R^{423}$), —OC(O)$R^{421}$, —OC(O)N($R^{422}$)($R^{423}$), CN, CF$_3$, NO$_2$, SO$_2$, —SO$R^{421}$, —SO$_3$$R^{421}$, —SO$_2$N($R^{422}$) ($R^{423}$), -alkyl-O-alkyl, -alkyl-O-aryl, halo, cycloalkyl, cycloalkenyl, aryl and heteroaryl;
or $R^{42}$ is selected from a group having the formula

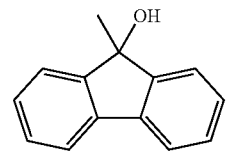

each $R^{421}$ is independently selected from H, alkyl, cycloalkyl, alkenyl, alkynyl, aralkyl, aryl and heteroaryl;
each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;
each $R^{424}$ is independently selected from H, OH, alkyl, cycloalkyl, alkenyl, alkynyl, aralkyl, aryl and heteroaryl;
each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to which they are attached form a 5- to 7-membered ring which may optionally contain a further heteroatom;
a is 1 to 6;
or a pharmaceutically acceptable salt or hydrate thereof.
In another embodiment of the invention, $R^4$ of a compound according to the formula II is selected to be a group of the formula

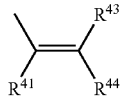

and $R^6$ is combined with $R^{41}$ to give a compound having the formula VI:

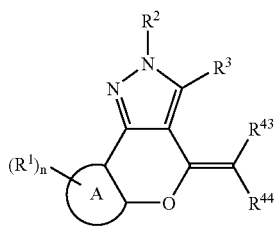

(VI)

wherein ring A is selected from a 5- or 6-membered aromatic rings which may optionally contain 0 to 3 ring heteroatoms;

each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2$$R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3$$R^{11}$, —SO$_2$N($R^{12}$)($R^{13}$), -alkyl-O—$R^{11}$, cycloalkyl, cycloalkenyl, halo, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

$R^2$ is selected from H, alkyl, cycloalkyl, cycloalkenyl, alkenyl, alkynyl, aralkyl, aryl, heteroaryl, —C(O)$R^{21}$, —C(O)O$R^{21}$, -alkyl-O-alkyl, -alkyl-O-aryl;

$R^{21}$ is selected from H, alkyl, alkyl-O-alkyl, alkyl-O-aryl, alkenyl, alkynyl, cycloalkyl, cycloalkenyl, aralkyl, aryl and heteroaryl;

$R^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)$R^{31}$, —C(O)O$R^{31}$, —C(O)N($R^{32}$)($R^{33}$);

$R^{31}$ is selected from H, alkyl, alkyl-O-alkyl, alkyl-O-aryl, alkenyl, alkynyl, cycloalkyl, cycloalkenyl, aralkyl, aryl and heteroaryl;

$R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, NO$_2$, CO$_2$$R^{34}$, C(O)$R^{34}$, —O—$R^{34}$, —N($R^{34}$)($R^{35}$), —N($R^{34}$)C(O)$R^{34}$, —N($R^{34}$)SO$_2$$R^{34}$, —S$R^{34}$, —C(O)N($R^{35}$)($R^{36}$), —OC(O)$R^{34}$, —OC(O)N($R^{35}$)($R^{36}$), SO$_2$, —SO$R^{34}$, —SO$_3$$R^{34}$, —SO$_2$N($R^{35}$)($R^{36}$), halo, cycloalkyl, cycloalkenyl, aryl and heteroaryl;

each $R^{34}$ is independently selected from H, alkyl, cycloalkyl, cycloalkeneyl, alkenyl, alkynyl, aralkyl, aryl and heteroaryl;

each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;

$R^{43}$, and $R^{44}$ are independently selected from H, alkyl, alkenyl, aralkyl, cycloalkyl, cycloalkenyl, -alkyl-O-alkyl and —(CH$_2$)$_a$—$R^{42}$;

$R^{42}$ is selected from —N($R^{421}$)C(O)$R^{421}$, —N($R^{421}$)SO$_2$$R^{421}$, —S$R^{421}$, —C(O)$R^{421}$, —C(O)O$R^{421}$, —C(O)N($R^{422}$)($R^{423}$), —OC(O)$R^{421}$, —OC(O)N($R^{422}$)($R^{23}$), CN, CF$_3$, NO$_2$, SO$_2$, —SO$R^{421}$, —SO$_3$$R^{421}$, —SO$_2$N($R^{422}$)($R^{423}$), -alkyl-O-alkyl, halo, aryl and heteroaryl;

or $R^{42}$ is selected from a group having the formula

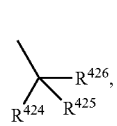 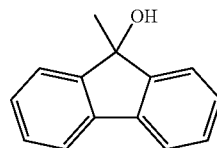

each $R^{421}$ is independently selected from H, alkyl, cycloalkyl, alkenyl, alkynyl, aralkyl, aryl and heteroaryl;

each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;

each $R^{424}$ is independently selected from H, OH, alkyl, cycloalkyl, alkenyl, alkynyl, aralkyl, aryl and heteroaryl;

each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to which they are attached form a 5- to 7-membered ring which may optionally contain a further heteroatom; and a is 1 to 6;

or a pharmaceutically acceptable salt or hydrate thereof.

In a preferred embodiment of the invention, the ring A of the compound according to formula VI is selected to be a phenyl or substituted phenyl to give a compound of the formula VI$_a$:

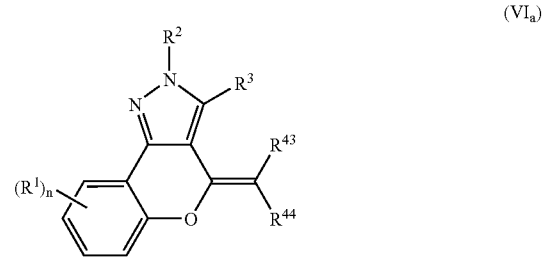

wherein each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2$$R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3$$R^{11}$, —SO$_2$N($R^{12}$)($R^{13}$), -alkyl-O—$R^{11}$, cycloalkyl, cycloalkenyl, halo, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

$R^2$ is selected from H, alkyl, cycloalkyl, cycloalkenyl, alkenyl, alkynyl, aralkyl, aryl, heteroaryl, —C(O)$R^{21}$, —C(O)O$R^{21}$, -alkyl-O-alkyl, -alkyl-O-aryl;

$R^{21}$ is selected from H, alkyl, alkyl-O-alkyl, alkyl-O-aryl, alkenyl, alkynyl, cycloalkyl, cycloalkenyl, aralkyl, aryl and heteroaryl;

$R^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)$R^{31}$, —C(O)O$R^{31}$, —C(O)N($R^{32}$)($R^{33}$);

$R^{31}$ is selected from H, alkyl, alkyl-O-alkyl, alkyl-O-aryl, alkenyl, alkynyl, cycloalkyl, cycloalkenyl, aralkyl, aryl and heteroaryl;

$R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, NO$_2$, CO$_2$$R^{34}$, C(O)$R^{34}$, —O—$R^{34}$, —N($R^{34}$)($R^{35}$), —N($R^{34}$)C(O)$R^{34}$, —N($R^{34}$)SO$_2$$R^{34}$, —S$R^{34}$, —C(O)N($R^{35}$)($R^{36}$), —OC(O)$R^{34}$, —OC(O)N($R^{35}$)($R^{36}$), SO$_2$, —SO$R^{34}$, —SO$_3$$R^{34}$, —SO$_2$N($R^{35}$)($R^{36}$), halo, cycloalkyl, cycloalkenyl, aryl and heteroaryl;

each $R^{34}$ is independently selected from H, alkyl, cycloalkyl, cycloalkeneyl, alkenyl, alkynyl, aralkyl, aryl and heteroaryl;

each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;

$R^{43}$, and $R^{44}$ are independently selected from H, alkyl, alkenyl, aralkyl, cycloalkyl, cycloalkenyl, -alkyl-O-alkyl and —(CH$_2$)$_a$—$R^{42}$;

$R^{42}$ is selected from —N($R^{421}$)C(O)$R^{421}$, —N($R^{421}$)SO$_2$$R^{421}$, —S$R^{421}$, —C(O)$R^{421}$, —C(O)O$R^{421}$, —C(O)N($R^{422}$)($R^{423}$), —OC(O)$R^{421}$, —OC(O)N($R^{422}$)($R^{23}$), CN, CF$_3$, NO$_2$, SO$_2$, —SO$R^{421}$, —SO$_3$$R^{421}$, —SO$_2$N($R^{422}$)($R^{423}$), -alkyl-O-alkyl, halo, aryl and heteroaryl;

or $R^{42}$ is selected from a group having the formula

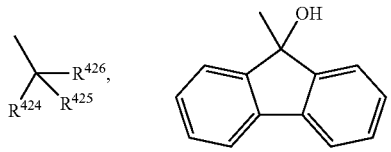

each $R^{421}$ is independently selected from H, alkyl, cycloalkyl, alkenyl, alkynyl, aralkyl, aryl and heteroaryl;

each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;

each $R^{424}$ is independently selected from H, OH, alkyl, cycloalkyl, alkenyl, alkynyl, aralkyl, aryl and heteroaryl; each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to which they are attached form a 5- to 7-membered ring which may optionally contain a further heteroatom; and a is 1 to 6;

or a pharmaceutically acceptable salt or hydrate thereof.

Table 2 provides representative embodiments for compounds of the formula VI.

TABLE 2

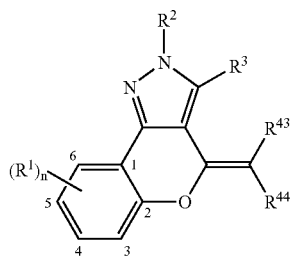

(VI)

| No. | $R^1$ | $R^2$ | $R^3$ | $R^{43}$ | $R^{44}$ | MW |
|---|---|---|---|---|---|---|
| 24698 | H | CH$_3$ | H | 4-methylphenyl | C(CH$_3$)(OH)(phenyl) | 408.49 |
| 24699 | H | CH$_3$ | H | 4-(CF$_3$)phenyl | C(CH$_3$)(OH)(phenyl) | 462.47 |

TABLE 2-continued
(VI)
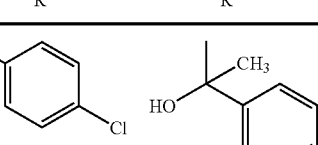
| No. | R¹ | R² | R³ | R⁴³ | R⁴⁴ | MW |
|---|---|---|---|---|---|---|
| 24700 | H | CH₃ | H | 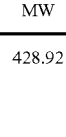 | 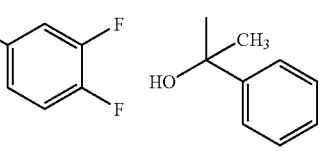 | 428.92 |
| 24701 | H | CH₃ | H |  | 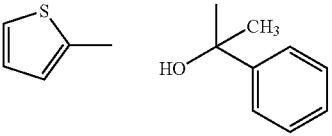 | 430.45 |
| 24702 | H | CH₃ | H |  | 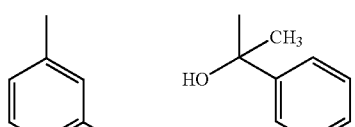 | 400.49 |
| 24703 | H | CH₃ | H |  | 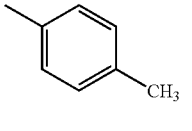 | 424.49 |
| 24704 | H | CH₃ | H |  | 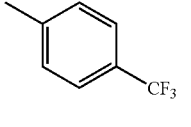 | 386.49 |
| 24705 | H | CH₃ | H | 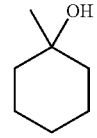 | 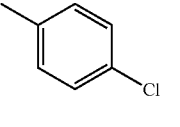 | 440.46 |
| 24706 | H | CH₃ | H | 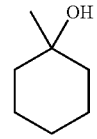 | 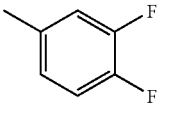 | 406.91 |
| 24707 | H | CH₃ | H | 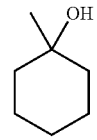 | | 408.45 |

TABLE 2-continued (VI)

| No. | R¹ | R² | R³ | R⁴³ | R⁴⁴ | MW |
|---|---|---|---|---|---|---|
| 24709 | H | CH₃ | H | 3-methoxyphenyl | 1-hydroxycyclohexyl | 409.49 |
| 24710 | 5-CH₃ | CH₃ | H | 4-methylphenyl | 2-hydroxy-2-phenylpropyl (1-hydroxy-1-methyl-1-phenylmethyl) | 422.52 |
| 24711 | 5-CH₃ | CH₃ | H | 4-chlorophenyl | 1-hydroxy-1-methyl-1-phenylmethyl | 442.94 |
| 24712 | 5-CH₃ | CH₃ | H | 3,4-difluorophenyl | 1-hydroxy-1-methyl-1-phenylmethyl | 444.48 |
| 24713 | 5-CH₃ | CH₃ | H | 2-thienyl | 1-hydroxy-1-methyl-1-phenylmethyl | 414.52 |
| 24714 | 5-CH₃ | CH₃ | H | 3-methoxy-5-methylphenyl | 1-hydroxy-1-methyl-1-phenylmethyl | 438.52 |
| 24722 | 5-Cl | CH₃ | H | 4-methylphenyl | 1-hydroxy-1-methyl-1-phenylmethyl | 442.94 |
| 24724 | 5-Cl | CH₃ | H | 4-trifluoromethylphenyl | 1-hydroxy-1-methyl-1-phenylmethyl | 496.92 |

TABLE 2-continued
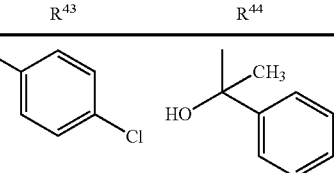
(VI)
| No. | R¹ | R² | R³ | R⁴³ | R⁴⁴ | MW |
|---|---|---|---|---|---|---|
| 24725 | 5-Cl | CH₃ | H | 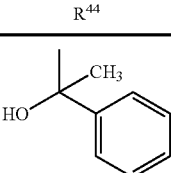 | 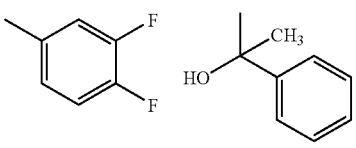 | 463.36 |
| 24726 | 5-Cl | CH₃ | H | 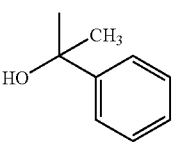 | 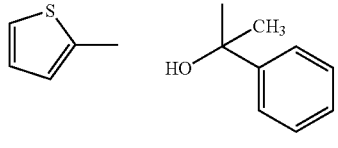 | 464.90 |
| 24727 | 5-Cl | CH₃ | H | 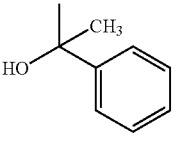 | 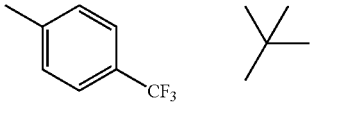 | 434.94 |
| 24730 | 5-Cl, 4-CH₃ | CH₃ | H |  |  | 446.90 |
| 24734 | 5-Cl, 4-CH₃ | CH₃ | H |  |  | 384.92 |
| 24735 | 5-Cl, 4-CH₃ | CH₃ | H |  | 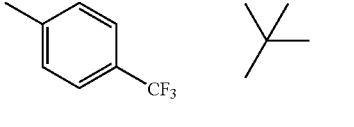 | 408.93 |
| 24737 | 5-Cl, 4-CH₃ | HOCH₂CH₂ | H |  | 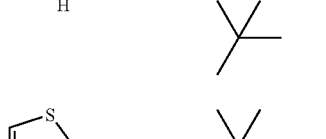 | 476.92 |
| 24738 | 5-Cl, 4-CH₃ | HOCH₂CH₂ | H | H | 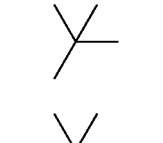 | 332.83 |
| 24741 | 5-Cl, 4-CH₃ | HOCH₂CH₂ | H | 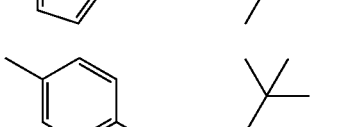 | 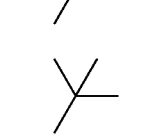 | 414.95 |
| 24744 | Br | CH₃ | H | 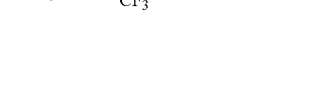 |  | 477.32 |

TABLE 2-continued
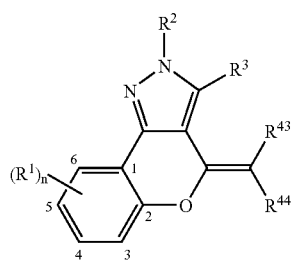
(VI)
| No. | R¹ | R² | R³ | R⁴³ | R⁴⁴ | MW |
|---|---|---|---|---|---|---|
| 24745 | Br | CH₃ | H | 4-Cl-C₆H₄ | t-Bu | 443.77 |
| 24746 | Br | CH₃ | H | 3,4-diF-C₆H₃ | t-Bu | 445.30 |
| 24747 | Br | CH₃ | H | 2-thienyl | t-Bu | 415.35 |
| 24748 | Br | CH₃ | H | 3-OMe-C₆H₄ | t-Bu | 439.35 |
| 24749 | NO₂ | CH₃ | H | 4-Cl-C₆H₄ | t-Bu | 409.87 |
| 24750 | NO₂ | CH₃ | H | 2-thienyl | t-Bu | 381.45 |
| 24751 | 5-Cl, 4-CH₃ | CH₃ | H | 4-CH₃-C₆H₄ | (CH₂)₃CN | 403.91 |
| 24995 | 5-Cl, 4-CH₃ | HOCH₂CH₂ | H | 4-CH₃-C₆H₄ | 4-CH₃-C₆H₄ | 456.97 |
| 25047 | H | CH₃ | H | 4-(C(O)CH₃)-C₆H₄ | 4-CH₃-C₆H₄ | 406.48 |
| 25041 | H | CH₃ | H | 3-OMe-C₆H₄ | 4-CH₃-C₆H₄ | 394.47 |

TABLE 2-continued (VI)

| No. | R$^1$ | R$^2$ | R$^3$ | R$^{43}$ | R$^{44}$ | MW |
|---|---|---|---|---|---|---|
| 25044 | H | CH$_3$ | H | 4-CF$_3$-C$_6$H$_4$- | 4-CH$_3$-C$_6$H$_4$- | 432.44 |
| 25043 | H | CH$_3$ | H | 3-Cl-C$_6$H$_4$- | 4-CH$_3$-C$_6$H$_4$- | 398.89 |
| 25042 | H | CH$_3$ | H | 3,4-F$_2$-C$_6$H$_3$- | 4-CH$_3$-C$_6$H$_4$- | 400.42 |
| 25028 | H | CH$_3$ | H | 4-(C(=O))-C$_6$H$_4$- | 3-OMe-C$_6$H$_4$- | 422.48 |
| 25029 | H | CH$_3$ | H | 4-(C(=O))-C$_6$H$_4$- | 4-Cl-C$_6$H$_4$- | 426.90 |
| 25030 | H | CH$_3$ | H | 4-(C(=O))-C$_6$H$_4$- | -(CH$_2$)$_3$CN | 383.45 |
| 25031 | 5-CH$_3$ | CH$_3$ | H | 4-(C(=O))-C$_6$H$_4$- | 4-CH$_3$-C$_6$H$_4$- | 420.51 |
| 25032 | 5-Cl | CH$_3$ | H | 4-(C(=O))-C$_6$H$_4$- | 4-CH$_3$-C$_6$H$_4$- | 440.92 |
| 25033 | 5-NO$_2$ | CH$_3$ | H | 4-(C(=O))-C$_6$H$_4$- | 4-CH$_3$-C$_6$H$_4$- | 451.48 |

In another embodiment of the invention, $R^4$ of a compound according to formula II is selected to be a group of the formula

and $R^6$ is combined with $R^{41}$ to give a compound having the formula VII:

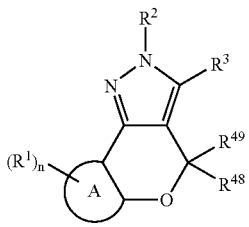

(VII)

wherein ring A is selected from a 5- or 6-membered aromatic rings which may optionally contain 0 to 3 ring heteroatoms;

each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2$$R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3$$R^{11}$, —SO$_2$N($R^{12}$)($R^{13}$), -alkyl-O—$R^{11}$, cycloalkyl, cycloalkenyl, halo, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

$R^2$ is selected from H, alkyl, cycloalkyl, cycloalkenyl, alkenyl, alkynyl, aralkyl, aryl, heteroaryl, —C(O)$R^{21}$, —C(O)O$R^{21}$, -alkyl-O-alkyl, -alkyl-O-aryl;

$R^{21}$ is selected from H, alkyl, alkyl-O-alkyl, alkyl-O-aryl, alkenyl, alkynyl, cycloalkyl, cycloalkenyl, aralkyl, aryl and heteroaryl;

$R^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)$R^{31}$, —C(O)O$R^{31}$, —C(O)N($R^{32}$)($R^{33}$);

$R^{31}$ is selected from H, alkyl, alkyl-O-alkyl, alkyl-O-aryl, alkenyl, alkynyl, cycloalkyl, cycloalkenyl, aralkyl, aryl and heteroaryl;

$R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, NO$_2$, CO$_2$$R^{34}$, C(O)$R^{34}$, $R^{34}$—N($R^{34}$)($R^{35}$), —N($R^{34}$)C(O)$R^{34}$, —N($R^{34}$)SO$_2$$R^{34}$—S$R^{34}$, —C(O)N($R^{35}$)($R^{36}$), —OC(O)$R^{34}$, —OC(O)N($R^{35}$)($R^{36}$), SO$_2$, —SO$R^{34}$, —SO$_3$$R^{34}$, —SO$_2$N($R^{35}$)($R^{36}$), halo, cycloalkyl, cycloalkenyl, aryl and heteroaryl;

each $R^{34}$ is independently selected from H, alkyl, cycloalkyl, cycloalkeneyl, alkenyl, alkynyl, aralkyl, aryl and heteroaryl;

each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;

$R^{48}$ and $R^{49}$ are independently selected from H, alkyl, alkenyl, aralkyl, cycloalkyl, cycloalkenyl, -alkyl-O-alkyl and —(CH$_2$)$_a$—$R^{42}$;

$R^{42}$ is selected from —N($R^{421}$)C(O)$R^{421}$, —N($R^{421}$)SO$_2$$R^{421}$, —S$R^{421}$, —C(O)$R^{421}$, —C(O)O$R^{421}$, —C(O)N($R^{422}$)($R^{423}$), —OC(O)$R^{421}$, —OC(O)N($R^{422}$)($R^{423}$), CN, CF$_3$, NO$_2$, SO$_2$, —SO$R^{421}$, —SO$_3$$R^{421}$, —SO$_2$N($R^{422}$)($R^{423}$), -alkyl-O-alkyl, halo, aryl and heteroaryl;

or $R^{42}$ is selected from a group having the formula

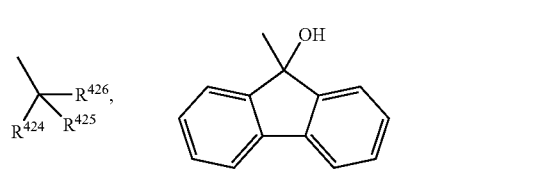

each $R^{421}$ is independently selected from H, alkyl, cycloalkyl, alkenyl, alkynyl, aralkyl, aryl and heteroaryl;

each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;

each $R^{424}$ is independently selected from H, OH, alkyl, cycloalkyl, alkenyl, alkynyl, aralkyl, aryl and heteroaryl;

each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to which they are attached form a 5- to 7-membered ring which may optionally contain a further heteroatom; and a is 1 to 6;

or a pharmaceutically acceptable salt or hydrate thereof.

In a preferred embodiment of the invention, the ring A of the compound according to formula VII is selected to be a phenyl or substituted phenyl to give a compound of the formula VII$_a$:

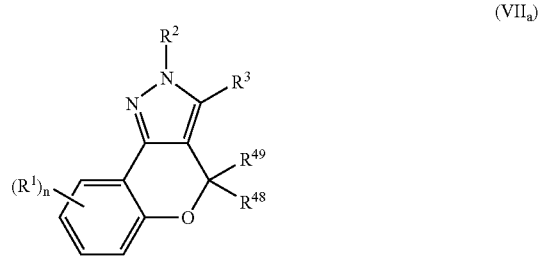

(VII$_a$)

wherein
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3R^{11}$, —SO$_2$N($R^{12}$)($R^{13}$), -alkyl-O—$R^{11}$, cycloalkyl, cycloalkenyl, halo, aryl and heteroaryl;
additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;
each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom,
n is 0 to 4;
$R^2$ is selected from H, alkyl, cycloalkyl, cycloalkenyl, alkenyl, alkynyl, aralkyl, aryl, heteroaryl, —C(O)$R^{21}$, —C(O)O$R^{21}$, -alkyl-O-alkyl, -alkyl-O-aryl;
$R^{21}$ is selected from H, alkyl, alkyl-O-alkyl, alkyl-O-aryl, alkenyl, alkynyl, cycloalkyl, cycloalkenyl, aralkyl, aryl and heteroaryl;
$R^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)$R^{31}$, —C(O)O$R^{31}$, —C(O)N($R^{32}$)($R^{33}$);
$R^{31}$ is selected from H, alkyl, alkyl-O-alkyl, alkyl-O-aryl, alkenyl, alkynyl, cycloalkyl, cycloalkenyl, aralkyl, aryl and heteroaryl;
$R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, NO$_2$, CO$_2R^{34}$, C(O)$R^{34}$, —O—$R^{34}$, —N($R^{34}$)($R^{35}$), —N($R^{34}$)C(O)$R^{34}$, —N($R^{34}$)SO$_2R^{34}$, —S$R^{34}$, —C(O)N($R^{35}$)($R^{36}$), —OC(O)$R^{34}$, —OC(O)N($R^{35}$)($R^{36}$), SO$_2$, —SO$R^{34}$, —SO$_3R^{34}$, —SO$_2$N($R^{35}$)($R^{36}$), halo, cycloalkyl, cycloalkenyl, aryl and heteroaryl;

each $R^{34}$ is independently selected from H, alkyl, cycloalkyl, cycloalkeneyl, alkenyl, alkynyl, aralkyl, aryl and heteroaryl;
each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;
$R^{48}$ and $R^{49}$ are independently selected from H, alkyl, alkenyl, aralkyl, cycloalkyl, cycloalkenyl, -alkyl-O-alkyl and —(CH$_2$)$_a$—$R^{42}$;
$R^{42}$ is selected from —N($R^{421}$)C(O)$R^{421}$, —N(421)SO$_2R^{421}$, —S$R^{421}$, —C(O)$R^{421}$, —C(O)O$R^{421}$, —C(O)N($R^{422}$)($R^{423}$), —OC(O)$R^{421}$, —OC(O)N($R^{422}$)($R^{423}$), CN, CF$_3$, NO$_2$, SO$_2$, —SO$R^{421}$, —SO$_3R^{421}$, —SO$_2$N($R^{422}$)($R^{423}$), -alkyl-O-alkyl, halo, aryl and heteroaryl;
or $R^{42}$ is selected from a group having the formula

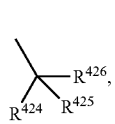 , 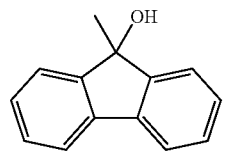

each $R^{421}$ is independently selected from H, alkyl, cycloalkyl, alkenyl, alkynyl, aralkyl, aryl and heteroaryl;
each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;
each $R^{424}$ is independently selected from H, OH, alkyl, cycloalkyl, alkenyl, alkynyl, aralkyl, aryl and heteroaryl;
each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to which they are attached form a 5- to 7-membered ring which may optionally contain a further heteroatom; and
a is 1 to 6;
or a pharmaceutically acceptable salt or hydrate thereof.
Table 3 provides representative embodiments for compounds of the formula VII$_a$.

TABLE 3

(VII$_a$)

| No. | $R^1$ | $R^2$ | $R^3$ | $R^{48}$ | $R^{49}$ | MW |
|---|---|---|---|---|---|---|
| 33473 | 5-NO$_2$ | (2-Cl,4-CH$_3$-phenyl) | Cl | H | —OH | —CH$_2$C(CH$_3$)$_3$ | 427.88 |

TABLE 3-continued
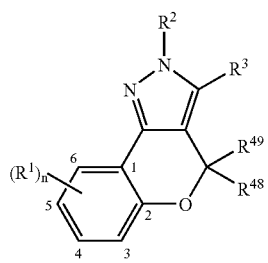
(VII_a)
| No. | R¹ | R² | R³ | R⁴⁸ | R⁴⁹ | MW |
|---|---|---|---|---|---|---|
| 33477 | 5-NO$_2$ | 3,4-dichlorophenyl | H | —OH | —CH$_2$C(CH$_3$)$_3$ | 448.30 |
| 33479 | 5-NO$_2$ | 2-fluorophenyl | H | —OH | —CH$_2$C(CH$_3$)$_3$ | 397.40 |
| 33480 | 5-NO$_2$ | 4-chloro-2-fluorophenyl | H | —OH | —CH$_2$C(CH$_3$)$_3$ | 431.84 |
| 33483 | 5-NO$_2$ | 3,5-dichlorophenyl | H | —OH | —CH$_2$C(CH$_3$)$_3$ | 448.30 |
| 33484 | 5-NO$_2$ | 4-fluorophenyl | H | —OH | —CH$_2$C(CH$_3$)$_3$ | 397.40 |
| 33485 | 5-NO$_2$ | 2,5-difluorophenyl | H | —OH | —CH$_2$C(CH$_3$)$_3$ | 415.39 |
| 33488 | 5-NO$_2$ | 2-methylphenyl | H | —OH | —CH$_2$C(CH$_3$)$_3$ | 393.44 |
| 33490 | 5-NO$_2$ | 2-chlorophenyl | H | —OH | —CH$_2$C(CH$_3$)$_3$ | 429.39 |

In another embodiment of the invention, $R^4$ of a compound according to the formula II is selected to be a group of the formula

and $R^6$ is combined with $R^{41}$ to give a compound having the formula VIII:

(VIII)

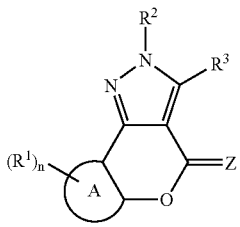

wherein ring A is selected from a 5- or 6-membered aromatic rings which may optionally contain 0 to 3 ring heteroatoms;

each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, —S$R^{11}$, —C(O)$R^{11}$, —C(O)O$R^{11}$, —C(O)N($R^{12}$)($R^{13}$), —OC(O)R, —OC(O)N($R^{12}$)($R^{13}$), CN, CF$_3$, NO$_2$, SO$_2$, —SOR, —SO$_3R^{11}$, —SO$_2$N($R^{12}$)($R^{13}$), -alkyl-O—$R^{11}$, cycloalkyl, cycloalkenyl, halo, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

$R^2$ is selected from H, alkyl, cycloalkyl, cycloalkenyl, alkenyl, alkynyl, aralkyl, aryl, heteroaryl, —C(O)$R^{21}$, —C(O)O$R^{21}$, -alkyl-O-alkyl, -alkyl-O-aryl;

$R^{21}$ is selected from H, alkyl, alkyl-O-alkyl, alkyl-O-aryl, alkenyl, alkynyl, cycloalkyl, cycloalkenyl, aralkyl, aryl and heteroaryl;

$R^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)$R^{31}$, —C(O)O$R^{31}$, —C(O)N($R^{32}$)($R^{33}$);

$R^{31}$ is selected from H, alkyl, alkyl-O-alkyl, alkyl-O-aryl, alkenyl, alkynyl, cycloalkyl, cycloalkenyl, aralkyl, aryl and heteroaryl;

$R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, NO$_2$, CO$_2R^{34}$, C(O)$R^{34}$, —O—$R^{34}$, —N($R^{34}$)($R^{35}$), —N($R^{34}$)C(O)$R^{34}$, —N($R^{34}$)SO$_2R^{34}$, —S$R^{34}$, —C(O)N($R^{35}$)($R^{36}$), —OC(O)$R^{34}$, OC(O)N($R^{35}$)($R^{36}$), SO$_2$, —SO$R^{34}$, —SO$_3R^{34}$, —SO$_2$N($R^{35}$)($R^{36}$), halo, cycloalkyl, cycloalkenyl, aryl and heteroaryl;

each $R^{34}$ is independently selected from H, alkyl, cycloalkyl, cycloalkeneyl, alkenyl, alkynyl, aralkyl, aryl and heteroaryl;

each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;

Z is selected from O, N—O$R^{461}$;

$R^{461}$ is selected from H, alkyl, alkenyl, aralkyl, cycloalkyl, cycloalkenyl, -alkyl-O-alkyl and —(CH$_2$)$_a$—$R^{42}$ $R^{42}$ is selected from —N($R^{421}$)C(O)$R^{421}$, —N($R^{421}$)SO$_2R^{421}$, —S$R^{421}$, —C(O)$R^{421}$, C(O)O$R^{421}$, —C(O)N($R^{422}$)($R^{423}$), —OC(O)$R^{421}$, —OC(O)N($R^{422}$)($R^{423}$), CN, CF$_3$, NO$_2$, SO$_2$, —SO$R^{421}$, —SO$_3R^{421}$, —SO$_2$N($R^{422}$)($R^{423}$), -alkyl-O-alkyl, halo, aryl and heteroaryl;

or $R^{42}$ is selected from a group having the formula

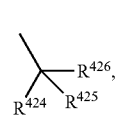 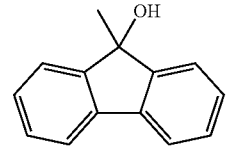

each $R^{421}$ is independently selected from H, alkyl, cycloalkyl, alkenyl, alkynyl, aralkyl, aryl and heteroaryl;

each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;

each $R^{424}$ is independently selected from H, OH, alkyl, cycloalkyl, alkenyl, alkynyl, aralkyl, aryl and heteroaryl;

each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to which they are attached form a 5- to 7-membered ring which may optionally contain a further heteroatom; and a is 1 to 6;

or a pharmaceutically acceptable salt or hydrate thereof.

In a preferred embodiment of the invention, the ring A of the compound according to formula VIII is selected to be a phenyl or substituted phenyl to give a compound of the formula VIII$_a$:

(VIII$_a$)

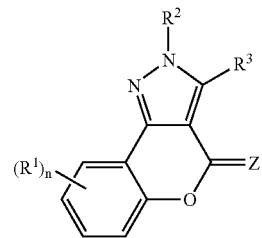

wherein
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3R^{11}$, —SO$_2$N($R^{12}$)($R^{13}$), -alkyl-O—$R^{11}$, cycloalkyl, cycloalkenyl, halo, aryl and heteroaryl;
additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;
each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom,
n is 0 to 4;
$R^2$ is selected from H, alkyl, cycloalkyl, cycloalkenyl, alkenyl, alkynyl, aralkyl, aryl, heteroaryl, —C(O)$R^{21}$, —C(O)O$R^{21}$, -alkyl-O-alkyl, -alkyl-O-aryl;
$R^{21}$ is selected from H, alkyl, alkyl-O-alkyl, alkyl-O-aryl, alkenyl, alkynyl, cycloalkyl, cycloalkenyl, aralkyl, aryl and heteroaryl;
$R^3$ is selected from H, alkyl, cycloalkyl, cyloalkenyl, alkenyl, alkynyl, -alkyl-O-alkyl, alkyl-O-aryl, aralkyl, aryl, heteroaryl, —C(O)$R^{31}$, —C(O)O$R^{31}$, —C(O)N($R^{32}$)($R^{33}$);
$R^{31}$ is selected from H, alkyl, alkyl-O-alkyl, alkyl-O-aryl, alkenyl, alkynyl, cycloalkyl, cycloalkenyl, aralkyl, aryl and heteroaryl;
$R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, NO$_2$, CO$_2R^{34}$, C(O)$R^{34}$—O—$R^{34}$—N($R^{34}$)($R^{35}$), —N($R^{34}$)C(O)$R^{34}$, —N($R^{34}$)SO$_2R^{34}$, —S$R^{34}$, —C(O)N($R^{35}$)($R^{36}$), —OC(O)$R^{34}$, —OC(O)N($R^{35}$)($R^{36}$), SO$_2$, —SO$R^{34}$, —SO$_3R^{34}$, —SO$_2$N($R^{35}$)($R^{36}$), halo, cycloalkyl, cycloalkenyl, aryl and heteroaryl;
each $R^{34}$ is independently selected from H, alkyl, cycloalkyl, cycloalkeneyl, alkenyl, alkynyl, aralkyl, aryl and heteroaryl;
each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;
Z is selected from O, N—O$R^{461}$;
$R^{461}$ is selected from H, alkyl, alkenyl, aralkyl, cycloalkyl, cycloalkenyl, -alkyl-O-alkyl and —(CH$_2$)$_a$—$R^{42}$
$R^{42}$ is selected from —N($R^{421}$)C(O)$R^{421}$, —N($R^{421}$)SO$_2R^{421}$, —S$R^{421}$, —C(O)$R^{421}$, —C(O)O$R^{421}$, —C(O)N($R^{422}$)($R^{423}$), —OC(O)$R^{421}$, —OC(O)N($R^{422}$)($R^{421}$), CN, CF$_3$, NO$_2$, SO$_2$, —SO$R^{421}$, —SO$_3R^{421}$, —SO$_2$N($R^{422}$)($R^{423}$), -alkyl-O-alkyl, halo, aryl and heteroaryl;

or $R^{42}$ is selected from a group having the formula

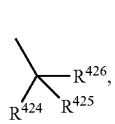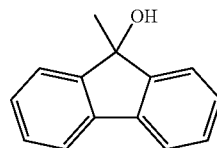

each $R^{421}$ is independently selected from H, alkyl, cycloalkyl, alkenyl, alkynyl, aralkyl, aryl and heteroaryl;
each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;
each $R^{424}$ is independently selected from H, OH, alkyl, cycloalkyl, alkenyl, alkynyl, aralkyl, aryl and heteroaryl;
each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to, which they are attached form a 5- to 7-membered ring which may optionally contain a further heteroatom; and
a is 1 to 6;
or a pharmaceutically acceptable salt or hydrate thereof.

In another embodiment of the invention, two compounds of the formula I are linked by a linking group, L, to form a dimeric compound. The two compounds of the formula I which are linked by L to form the dimeric compound may be linked through any position off of the formula I structure. Thus, two compounds of the formula I may be linked through a linking group at the position of $R^1$, $R^2$, $R^3$, $R^4$, or $R^5$.

In one embodiment, the dimeric compound is linked through $R^4$ of the compounds of formula I. In this embodiment, $R^4$ of a compound according to formula I is selected to be a group of the formula

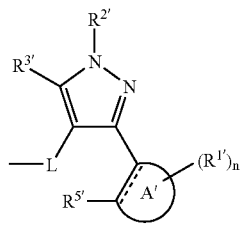

The resulting "dimeric" compound may be symmetric or unsymmetrical and is represented by the formula X:

(X)

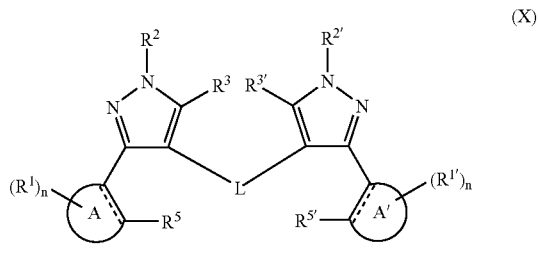

wherein:

ring A and ring A' are independently selected from 5- or 6-membered aromatic rings which may optionally contain 0 to 3 ring heteroatoms;

each $R^1$ and $R^{1'}$ are selected independently from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2$$R^{11}$, —SR$^{11}$, —C(O)R$^{11}$, —C(O)OR$^{11}$, —C(O)N($R^{12}$)($R^{13}$), —OC(O)R$^{11}$, —OC(O)N($R^{12}$)($R^{13}$), CN, CF$_3$, NO$_2$, SO$_2$, —SOR$^{11}$, —SO$_3$R$^{11}$, —SO$_2$N($R^{12}$)($R^{13}$), -alkyl-O-alkyl, halo, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, cycloalkyl, alkenyl, alkynyl, aralkyl, aryl and heteroaryl;

each $R^{12}$ and $R^{13}$ are independently selected from H, alkyl, cycloalkyl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

$R^2$ and $R^{2'}$ are selected independently from H, alkyl, cycloalkyl, cycloalkenyl, alkenyl, alkynyl, aralkyl, aryl, heteroaryl, —C(O)R$^{21}$, —C(O)OR$^{21}$, -alkyl-O-alkyl, -alkyl-O-aryl;

$R^{21}$ is selected from H, alkyl, alkyl-O-alkyl, alkyl-O-aryl, alkenyl, alkynyl, cycloalkyl, cycloalkenyl, aralkyl, aryl and heteroaryl;

$R^3$ and $R^{3'}$ are independently selected from H, alkyl, cycloalkyl, cyloalkenyl, alkenyl, alkynyl, -alkyl-O-alkyl, alkyl-O-aryl, aralkyl, aryl, heteroaryl, —C(O)R$^{31}$, —C(O)OR$^{31}$, —C(O)N($R^{32}$)($R^{33}$);

$R^{31}$ is selected from H, alkyl, alkyl-O-alkyl, alkyl-O-aryl, alkenyl, alkynyl, cycloalkyl, cycloalkenyl, aralkyl, aryl and heteroaryl;

$R^{32}$ and $R^{33}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{32}$ and $R^{33}$ may be taken together with the nitrogen to which they are attached form a 5- to 7-membered ring which may optionally contain a further heteroatom and which may be optionally substituted with one or more CN, NO$_2$, CO$_2$R$^{34}$, C(O)R$^{34}$, —O—R$^{34}$, —N($R^{34}$)($R^{35}$), —N($R^{34}$)C(O)R$^{34}$, —N($R^{34}$)SO$_2$R$^{34}$, —SR$^{34}$, —C(O)N($R^{35}$)($R^{36}$), —OC(O)R$^{34}$, —OC(O)N($R^{35}$)($R^{36}$), SO$_2$, —SOR$^{34}$, —SO$_3$R$^{34}$, —SO$_2$N($R^{35}$)($R^{36}$), halo, cycloalkyl, cycloalkenyl, aryl and heteroaryl;

each $R^{34}$ is independently selected from H, alkyl, cycloalkyl, cycloalkeneyl, alkenyl, alkynyl, aralkyl, aryl and heteroaryl;

each $R^{35}$ and $R^{36}$ are independently selected from H, alkyl, cycloalkyl, alkenyl, alkynyl, aralkyl, aryl and heteroaryl; or $R^{35}$ and $R^{36}$ may be taken together with the nitrogen to which they are attached form a 5- to 7-membered ring which may optionally contain a further heteroatom;

$R^5$ and $R^{5'}$ are independently selected from H, OR$^{51}$, —SR$^{51}$, alkyl, cycloalkyl, cycloalkenyl, alkenyl, alkynyl, CN, CF$_3$, NO$_2$, SO$_2$, —SOR$^{51}$, —SO$_3$R$^{51}$, —SO$_2$N($R^{52}$)($R^{53}$), -alkyl-O-alkyl, halo, aralkyl, aryl, heteroaryl, —C(O)R$^{51}$, —C(O)OR$^{51}$, —C(O)N($R^{52}$)($R^{53}$), —OC(O)R$^{51}$, —OC(O)N($R^{52}$)($R^{53}$), —O(CH$_2$)$_e$C(O)OR$^{51}$, —O(CH$_2$)$_e$C(O)N($R^{52}$)($R^{53}$), —N($R^{52}$)($R^{53}$), —N($R^{51}$)C(O)R$^{51}$, and —N($R^{51}$)SO$_2$R$^{51}$ each $R^{51}$ is independently selected from H, alkyl, cycloalkyl, cycloalkenyl, alkenyl, alkynyl, aralkyl, aryl and heteroaryl;

$R^{52}$ and $R^{53}$ are independently selected from H, alkyl, cycloalkyl, cycloalkenyl, alkenyl, alkynyl, aralkyl, aryl and heteroaryl;

or $R^{52}$ and $R^{53}$ may be taken together with the nitrogen to which they are attached form a 5- to 7-membered ring which may optionally contain a further heteroatom;

e is 1 to 6;

alternatively, —O—R$^{51}$ is combined with R$^{41}$, R$^{46}$, or R$^{47}$ to give a 6-membered ring that is fused to ring A and to the pyrazole ring;

or $R^5$ is selected from a group having the formula:

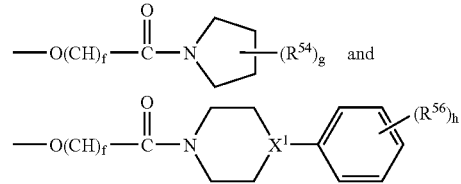

wherein each $R^{54}$ and $R^{56}$ is independently selected from —OR$^{57}$, halo, alkyl, cycloalkyl, cycloalkenyl, alkenyl, alkynyl, NO$_2$, CN, —C(O)R$^{57}$, —C(O)OR$^{57}$, —C(O)N($R^{58}$)($R^{59}$), —OC(O)R$^{57}$, —OC(O)N($R^{58}$)($R^{59}$), O(CH$_2$)$_i$C(O)OR$^{57}$, —O(CH$_2$)$_i$C(O)N($R^{58}$)($R^{59}$), —N($R^{58}$)($R^{59}$), —N($R^{57}$)C(O)R$^{57}$, —N($R^{57}$)SO$_2$R$^{57}$, aralkyl, aryl and heteroaryl;

each $R^{57}$ is independently selected from H, alkyl, cycloalkyl, cycloalkenyl, alkenyl, alkynyl, aralkyl, aryl and heteroaryl;

$R^{58}$ and $R^{59}$ are independently selected from H, alkyl, cycloalkyl, cycloalkenyl, alkenyl, alkynyl, aralkyl, aryl and heteroaryl; or $R^{52}$ and $R^{53}$ may be taken together with the nitrogen to which they are attached form a 5- to 7-membered ring which may optionally contain a further heteroatom;

i is 1 to 6;

$X^1$ is selected from N and CH;

f is 1 to 6;

g is 0 to 4; and h is 0 to 5;

L is a linking group selected from —(CH$_2$)$_x$—,

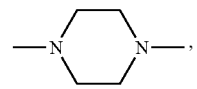

or a group of the formula

-A-B-A- wherein

A is selected from —N(R)—, —O—, —S—, —C(O)—, —OC(O)—, —N(R)C(O)—, —N(R)C(O)O—, —N(R)SO$_2$—, —(CH$_2$)$_y$—, and —C≡C—;

B is selected from —(CH$_2$)$_z$—,

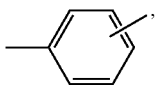

—(CH$_2$)$_v$-D-(CH$_2$)$_w$— wherein D is selected from O, S, —C═C—, —S—S—,

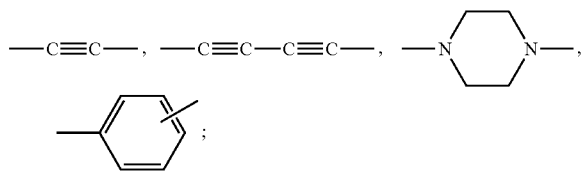

x is 3 to 25;
y is 1 to 10;
z is 1 to 10;
v is 1 to 8; and
w is 1 to 8;
or a pharmaceutically acceptable salt or hydrate thereof.

In another embodiment, the dimeric compound is linked through R$^5$ of the compounds of formula 1. In this embodiment, R$^5$ of a compound according to formula I is selected to be a group of the formula:

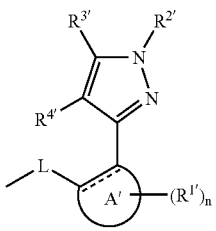

The resulting dimeric compound may be symmetric or unsymmetrical and is represented by the formula XI:

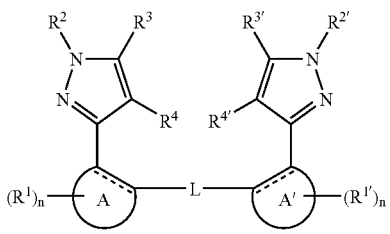

wherein
ring A and ring A' are independently selected from 5- or 6-membered aromatic rings which may optionally contain 0 to 3 ring heteroatoms;
each R$^1$ and R$^{1'}$ are selected independently from alkyl, alkenyl, alkynyl, aralkyl, —O—R$^{11}$, —N(R$^{12}$)(R$^{13}$), —N(R$^{11}$)C(O)R$^{11}$, —N(R$^{11}$)SO$_2$R$^{11}$, —SR$^{11}$, —C(O)R$^{11}$, —C(O)OR$^{11}$, —C(O)N(R$^{12}$)(R$^{13}$), —OC(O)R$^{11}$, —OC(O)N(R$^{12}$)(R$^{13}$), CN, CF$_3$, NO$_2$, SO$_2$, —SOR$^{11}$, —SO$_3$R$^{11}$, —SO$_2$N(R$^{12}$)(R$^{13}$), -alkyl-O-alkyl, halo, aryl and heteroaryl;
additionally or alternatively two R$^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from R$^1$;
each R$^{11}$ is independently selected from H, alkyl, cycloalkyl, alkenyl, alkynyl, aralkyl, aryl and heteroaryl;
each R$^{12}$ and R$^{13}$ are independently selected from H, alkyl, cycloalkyl, alkenyl, alkynyl, aralkyl, aryl and heteroaryl; or R$^{12}$ and R$^{13}$ may be taken together with the nitrogen to which they are attached form a 5- to 7-membered ring which may optionally contain a further heteroatom,
n is 0 to 4;
R$^2$ and R$^{2'}$ are selected independently from H, alkyl, cycloalkyl, cycloalkenyl, alkenyl, alkynyl, aralkyl, aryl, heteroaryl, —C(O)R$^{21}$, —C(O)OR$^{21}$, -alkyl-O-alkyl, -alkyl-O-aryl;
R$^{21}$ is selected from H, alkyl, alkyl-O-alkyl, alkyl-O-aryl, alkenyl, alkynyl, cycloalkyl, cycloalkenyl, aralkyl, aryl and heteroaryl;
R$^3$ and R$^{3'}$ are independently selected from H, alkyl, cycloalkyl, cyloalkenyl, alkenyl, alkynyl, -alkyl-O-alkyl, alkyl-O-aryl, aralkyl, aryl, heteroaryl, —C(O)R$^{31}$, —C(O)OR$^{31}$, —C(O)N(R$^{32}$)(R$^{33}$);
R$^{31}$ is selected from H, alkyl, alkyl-O-alkyl, alkyl-O-aryl, alkenyl, alkynyl, cycloalkyl, cycloalkenyl, aralkyl, aryl and heteroaryl;
R$^{32}$ and R$^{33}$ are independently selected from H, alkyl, cycloalkyl, cycloalkenyl, alkyl-O-alkyl, alkyl-O-aryl, alkenyl, alkynyl, aralkyl, aryl and heteroaryl; or R$^{32}$ and R$^{33}$ may be taken together with the nitrogen to which they are attached form a 5- to 7-membered ring which may optionally contain a further heteroatom and which may be optionally substituted with one or more CN, NO$_2$, CO$_2$R$^{34}$, C(O)R$^{34}$, —O—R$^{34}$, —N(R$^{34}$)(R$^{35}$), —N(R$^{34}$)C(O)R$^{34}$, —N(R$^{34}$)SO$_2$R$^{34}$, —SR$^{34}$, —C(O)N(R$^{35}$)(R$^{36}$), —OC(O)R$^{34}$, —OC(O)N(R$^{35}$)(R$^{36}$), SO$_2$, —SOR$^{34}$, —SO$_3$R$^{34}$, —SO$_2$N(R$^{35}$)(R$^{36}$), halo, cycloalkyl, cycloalkenyl, aryl and heteroaryl;
each R$^{34}$ is independently selected from H, alkyl, cycloalkyl, cycloalkeneyl, alkenyl, alkynyl, aralkyl, aryl and heteroaryl;
each R$^{35}$ and R$^{36}$ are independently selected from H, alkyl, cycloalkyl, alkenyl, alkynyl, aralkyl, aryl and heteroaryl; or R$^{35}$ and R$^{36}$ may be taken together with the nitrogen to which they are attached form a 5- to 7-membered ring which may optionally contain a further heteroatom;
R$^4$ and R$^{4'}$ are selected from H, alkyl, -alkyl-O-alkyl, cycloalkyl, aralkyl, aryl, heteroaryl,

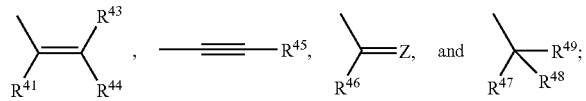

wherein
Z is selected from O, N—OR$^{461}$;
R$^{461}$ is selected from H, alkyl, alkenyl, aralkyl, cycloalkyl, cycloalkenyl, -alkyl-O-alkyl, alkyl-O-aryl and —(CH$_2$)$_q$—R$^{42}$
R$^{41}$, R$^{43}$, R$^{44}$, R$^{46}$, R$^{47}$, R$^{48}$ and R$^{49}$ are independently selected from H, alkyl, alkenyl, alkynyl, aralkyl, cycloalkyl, cycloalkenyl, -alkyl-O-alkyl, -alkyl-O-aryl, and —(CH$_2$)$_q$—R$^{42}$;

$R^{45}$ is selected from H, alkyl, -alkyl-O-alkyl, -alkyl-O-aryl, aryl, aralkyl, cycloalkyl, cycloalkenyl, and —$(CH_2)_a$—$R^{42}$;

$R^{42}$ is selected from —$N(R^{421})C(O)R^{421}$, —$N(2)SO_2R^{421}$, $OR^{421}$, —$SR^{421}$, —$C(O)R^{421}$, —$C(O)OR^{421}$, —$C(O)N(R^{422})(R^{423})$, —$OC(O)R^{421}$, —$OC(O)N(R^{422})(R^{423})$, CN, $CF_3$, $NO_2$, $SO_2$, —$SOR^{421}$, —$SO_3R^{421}$, —$SO_2N(R^{422})(R^{423})$, -alkyl-O-alkyl, -alkyl-O-aryl, halo, cycloalkyl, cycloalkenyl, aryl and heteroaryl;

or $R^{42}$ is selected from a group having the formula

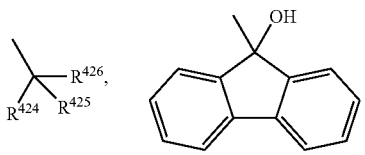

each $R^{421}$ is independently selected from H, alkyl, cycloalkyl, alkenyl, alkynyl, aralkyl, aryl and heteroaryl;

each $R^{422}$ and $R^{423}$ are independently selected from H, alkyl, cycloalkyl, alkenyl, alkynyl, aralkyl, aryl and heteroaryl; or $R^{422}$ and $R^{423}$ may be taken together with the nitrogen to which they are attached form a 5- to 7-membered ring which may optionally contain a further heteroatom;

each $R^{424}$ is independently selected from H, OH, alkyl, cycloalkyl, alkenyl, alkynyl, aralkyl, aryl and heteroaryl;

each $R^{425}$ and $R^{426}$ are independently selected from H, alkyl, cycloalkyl, alkenyl, alkynyl, aralkyl, aryl and heteroaryl; or $R^{425}$ and $R^{426}$ may be taken together with the carbon to which they are attached form a 5- to 7-membered ring which may optionally contain a further heteroatom;

a is 1 to 6;

L is a linking group selected from —$(CH_2)_x$—,

or a group of the formula

-A-B-A- wherein

A is selected from —N(R)—, —O—, —S—, —C(O)—, —OC(O)—, —N(R)C(O)—, —N(R)C(O)O—, —N(R)SO_2—, —$(CH_2)_y$—, and —C≡C—;

B is selected from —$(CH_2)_z$—,

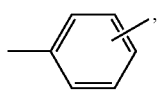

—$(CH_2)_v$-D-$(CH_2)_w$— wherein D is selected from O, S, —C=C—, —S—S—,

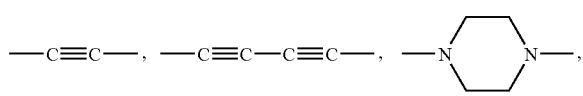

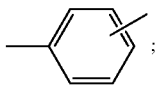

x is 3 to 25;
y is 1 to 10;
z is 1 to 10;
v is 1 to 8; and
w is 1 to 8;

or a pharmaceutically acceptable salt or hydrate thereof.

In another aspect of the invention, a synthetic process for the preparation of compounds of the formula I-V is provided. The inventive process uses mild reaction conditions, which provides a high substituent tolerance. The product is obtained in high yield and high purity. A process of the present invention is illustrated by Scheme I:

Scheme I step 1

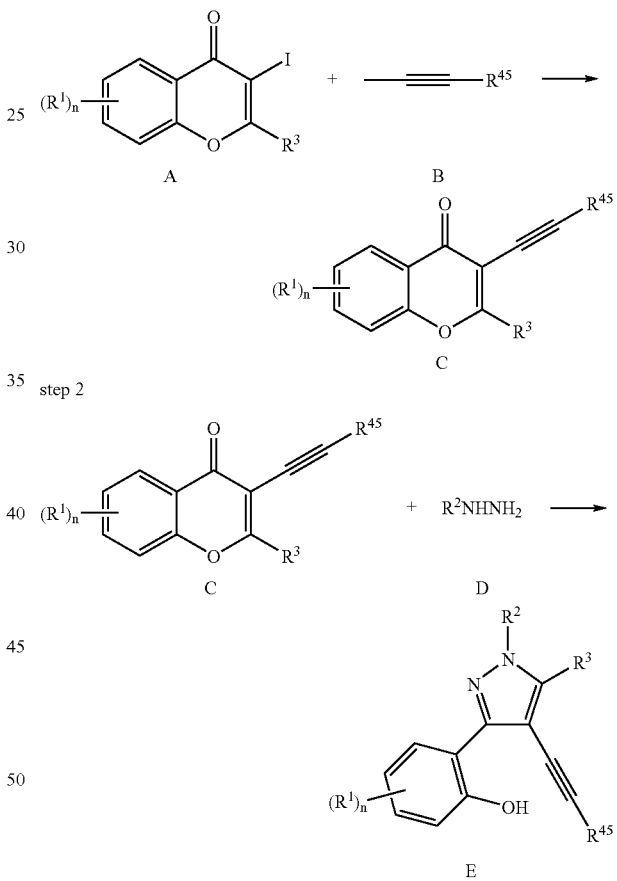

step 2

Step 1 of Scheme 1 preferably involves using a Sonogashira reaction in which a compound of the formula C is prepared by reacting a compound of the formula A with a terminal alkyne represented by the formula B in the presence of base and a transition metal catalyst, wherein $R^1$, $R^2$, $R^3$, $R^{15}$ and n are as described above for the compound of the formula I. A suitable base may be, for example, an organic base such as a primary, secondary or tertiary amine. Non-limiting examples include triethylamine, diisopropylamine, 1,8-diazabicyclo-[5.4.0]-undec-7-ene (DBU), 1,5-diazabicyclo-[4,3,0]-non-5-ene (DBN), or 1,4-diazabicyclo-[2.2.2]-octane (DABCO). Alternatively, an inorganic base may be used, such as an alkali metal or alkaline earth metal salt, such as a carbonate, bicarbonate or acetate salt.

The metal catalyst may be in the form of a salt or a complex with organic ligands. Particularly suitable metal catalysts are, for example, the Group VIII metals, preferably Pd(0) complexes or a Pd(II) salt. The ligands may be selected from, for example, phosphorus-containing ligands, such as triphenylphosphine (PPh$_3$) and 1,2-bis(diphenyl-phosphino)ethane (dppe). Preferred palladium catalysts include Pd(PPh$_3$)$_2$Cl$_2$, Pd(PPh$_3$)$_4$ and Pd(OAc)$_2$. The reaction is performed in the presence of a Cu(I) salt, such as a Cu(I) halide, Cu$_2$O, and CuCN, preferably CuI or CuCl. Suitable organic solvents include, but are not limited to, dioxane, tetrahydrofuran (THF) dimethylformamide (DMF), acetonitrile, dimethylsulfoxide, and other polar aprotic solvents or mixtures thereof. For further discussion of the Sonogashira reaction, see Sonogashira, K.; Tohda, Y,; Hagihara, N. *Tetrahedron Lett.* 1975, 4467-4470; Sonogashira, K. In *Comprehensive Organic Synthesis*, Trost, B. M.; Fleming, L., Eds., Pergamon Press: New York, 1991, Vol. 3, chapter 2.4; Liao, Y.; Fathi, R.; Reitman, M.; Zhang, Y.; Yang, Z. *Tetrahedron Lett.* 2001, 42, 1815-1818; Nicolaou, K. C.; Smith, A. L. *Acc. Chem. Res.* 1992, 25, 497-503; Porco, J. A., Jr.; Schoenen, F. J.; Stout, T. J.; Clardy, J.; Schreiber, S. L. *J. Am. Chem. Soc.* 1990, 112, 7410-7411; Hundertmark, T.; Littke, A. F.; Buchwald, S. L.; Fu, G. C. *Org. Lett.* 2000, 2, 1729-1731, and references therein; Takeuchi, R.; Tanabe, K.; Tanaka, S. *J. Org. Chem.* 2000, 65, 1558-1561; Arterburn, J. B.; Rao, K. V.; Perry, M. C. *Tetrahedron Lett.* 2000, 41, 839-842; Gan, Z.; Roy, R. *Tetrahedron Lett.* 2000, 41, 1155-1159; Godt, A.; Unsal, O.; Roos, M. *J. Org. Chem.* 2000, 65, 2837-2842; Wu, M. J.; Lin, C. F.; Chen, S. H. *Org. Lett.* 1999, 1, 767-768; Yoshimura, F.; Kawata, S.; Hirama, M. *Tetrahedron Lett.* 1999, 40, 8281-8286; Ma, S.; Shi, Z.; Yu, Z. *Tetrahedron Lett.* 1999, 40, 2393-2396; Tretyakov, E. V.; Knight, D. W.; Vasilevsky, S. F. *J. Chem. Soc., Perkin Trans.* 1, 1999, 3713-3720; Thorand, S.; Krause, N. *J. Org Chem.* 1998, 63, 8551-8553; and Sonogashira, K. in *Metal-Catalyzed Cross-Coupling Reactions*; Diederich, F., Stang, P. J., Wiley-VCH: New York, 1998; Chapter 5, each of which is incorporated by reference.

Step 2 of Scheme 1 involves a reaction in which a compound of the formula E is prepared by reacting a compound of the formula C with a hydrazine represented by the formula D. In a preferred embodiment, the hydrazine D is added directly to the pot containing the crude intermediate C.

In another aspect of the invention, a synthetic process for the preparation of compounds of the formula VI-VIII is provided. The inventive process uses mild reaction conditions, which provides a high substituent tolerance. The product is obtained in high yield and high purity. A process of the present invention is illustrated by Scheme II:

Scheme II

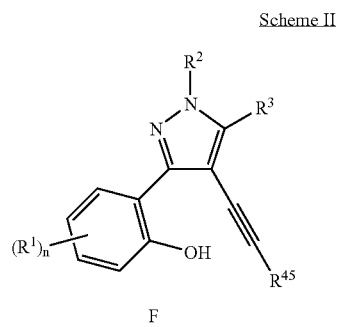

F

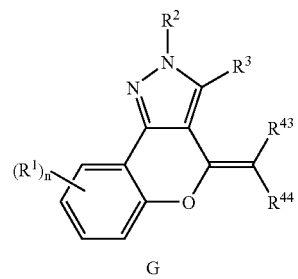

G

A solution of the pyrazole F in a polar aprotic solvent is added to a mixture of an appropriate Pd$^0$ catalyst (0.05 equiv.), Bpy (0.1 equiv.), base (4 equiv) and ArI (2 equiv.) in a polar aprotic solvent and then stirred for overnight at about 50-70° C. Appropriate Pd$^0$ catalysts include Pd(PPh$_3$)$_4$, Pd$_2$(dba)$_3$, 3-Pd$_2$(dba)$_2$/Pt—Bu$_3$, 4-Pd$_2$(dba)$_3$/dppf, and 5-Pd$_2$(dba)$_2$/bpy. The base may be selected from appropriate organic and inorganic bases including carbonate salts (for example, potassium carbonate, sodium carbonate, and cesium carbonate) and acetate salts (for example, sodium acetate). For further discussion of conditions and other modifications see: (a) Arcadi, A.; Cacchi, S.; Del Rosario, M.; Fabrizi, G.; Marinelli, F. *J. Org. Chem.* 1996, 61, 9280. (b) Arcadi, A.; Cacchi, S.; Giuseppe, S. D.; Fabrizi, G.; Marinelli, F. *Synlett.* 2002, 453. (c) Chaplin, J. H.; Flynn, B. L. *Chem. Commun.* 2001, 1594. (d) Hu, Y.; Nawoschik, K.; Liao, Y.; Ma, J.; Fathi, R.; Yang, Z.; *J. Org. Chem.* 2004, 69, 2235-2239. (e) Flynn, B. L.; Hamel, E.; Jung, M. K. *J. Med. Chem.* 2002, 45, 2670.

In alternative embodiments, aryl pyrazoles may be prepared according to the Scheme III:

Scheme III

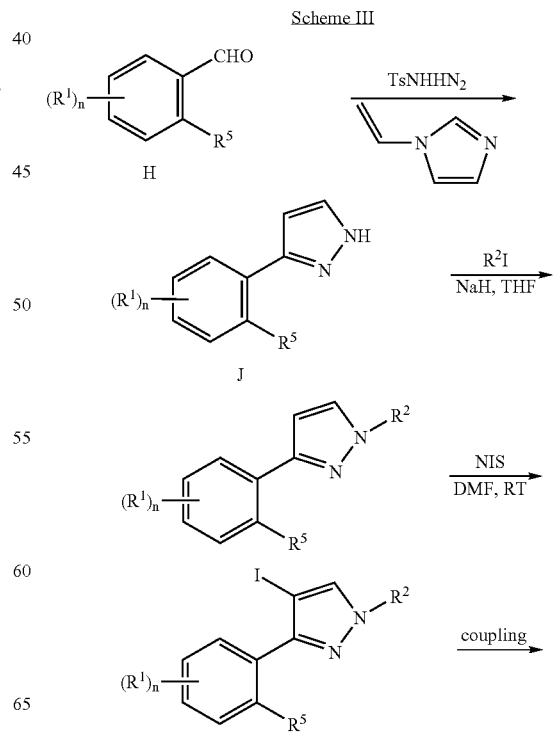

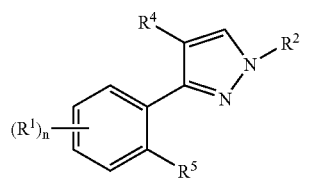

in which an aryl aldehyde H is treated with p-toluenesulfonyl hydrazide in a polar solvent, followed by treatment with base and N-vinyl imidazole. The resulting pyrazole may be further modified. For example the pyrazole may be alkylated by treatment with a strong base, such as NaH, followed by reaction with an alkylating agent. Alkylating agents may have the structure alkyl-LG, wherein LG represents a leaving group. The pyrazole ring may be further modified, for example, by treatment with iodosuccinimide followed by reaction with a terminal alkyne and metal catalyst, Boronic acid and metal catalyst, alkene and metal catalyst, alkyl tin and metal catalyst, etc. to give diversified derivatives.

Compounds of the formula VII$_a$ may be prepared, for example, according to Scheme IV:

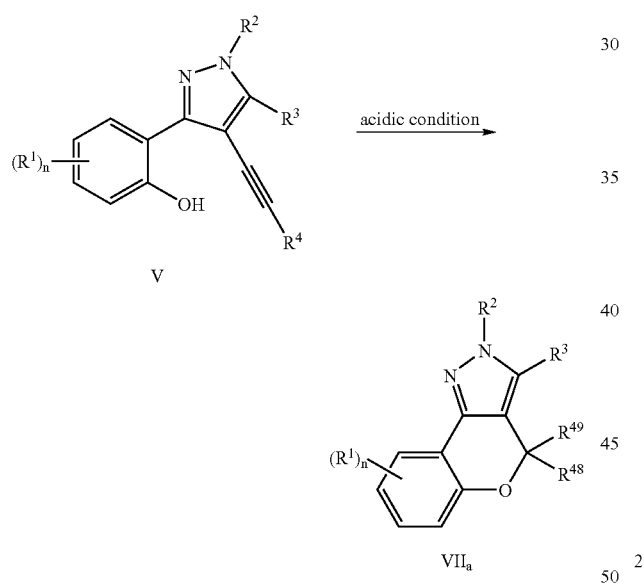

Compound V may be cyclized by treatment with a metal catalyst such as Nickel, Palladium, and Rhodium in a polar acidic solvent to give compounds VII$_a$.

Compounds of the formula VIII$_a$ may be prepared, for example, according to Scheme V:

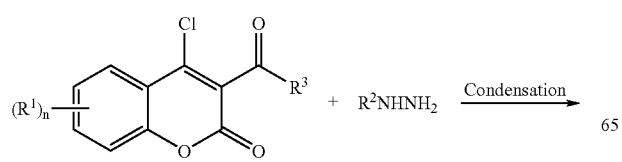

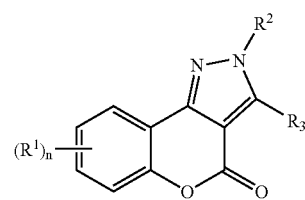

According to Scheme V, compound VIIIa can be synthesized by treating a 4-chloro-3-carbonyl-coumarin with a hydrazine using microwave in acetic acid conditions at about 150° C. for about 10 mins.

Dimeric compounds according to the present invention may be prepared according to the schemes provided below:

-continued

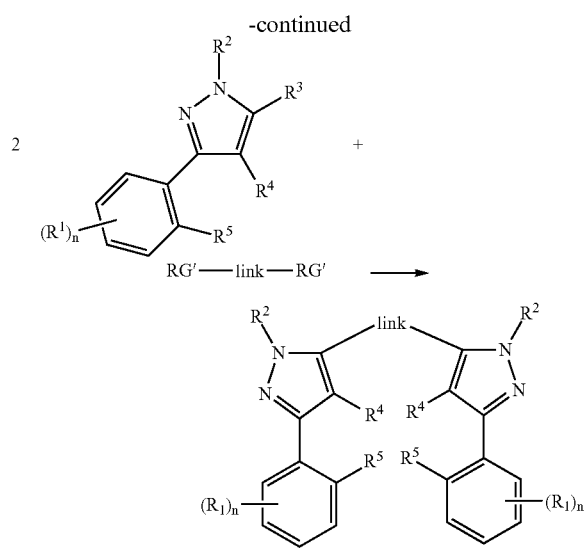

in which RG is a reactive group and RG' is its reactive partner. For example, RG may be a leaving group, such as tosylate, and RG' may be a nucleophile, such as an amine. Further examples of RG-RG' pairs include:
a) an activated carbonyl-containing group, such as an acyl halide or anhydride, which may be reacted with a nucleophile such as —$NH_2$, —OH, etc.
b) iodide which may be reacted with a terminal acetylene using a Sonogashira reaction or with boronic acid using Suzuki coupling, etc.
Other reactive groups/reactive partners will be apparent to the ordinarily skilled worker.

It may be advantageous to employ a temporary protecting group in achieving the final product. The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Further guidance for the synthesis of pyrazoles may be found in, for example, J. Elguero, Comprehensive Heterocyclic Chemistry II, Pergamon Press, Oxford, 1996, v. 3, p. 1. Starting materials useful for preparing compounds of the invention and intermediates thereof may be commercially available or can be prepared by well-known synthetic methods. Other methods for synthesis of the compounds described herein and/or starting materials are either described in the art or will be readily apparent to the skilled artisan. (see, e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Alternatives to the reagents and conditions may be found in the references provided above and in other compendiums well known to the skilled artisan. Accordingly, the synthetic methods and strategies presented herein are illustrative rather than comprehensive.

The compounds and processes disclosed herein are useful in the production of a library of pyrazole derivatives for biological screening. Derivatives of pyrazole posses a range of biological activities. Pryrazole-based compounds have shown efficacy, for example, as antivirals. Particularly, the compounds of the present invention may be used to prevent or treat infection with HCV.

The identification of inhibitors of HCV replication and/or proliferation has been facilitated by the development of a cell based system to study HCV replication and assay for HCV inhibitors. Inhibition of HCV replication may be performed using the HCV Replicon Assay developed in the laboratories of Bartenschlager (Lohman et al, *Science* 285, 110-113, 1999) and Rice (Blight et al, *Science* 290, 1972-1974, 2000). The assay is performed using the Huh-Luc-Neo cell line (Lohman et al, *Science* 285, 110-113, 1999). Huh-Luc-Neo cells are a human hepatoma cell line (Huh-7) stably expressing a bi-cistronic subgenomic replicon containing the HCV IRES in which the structural proteins of HCV had been deleted and replaced by a construct containing sequences coding for the firefly luciferase reporter gene, the neomycin selectable marker and the EMCV IRES to direct expression of a truncated HCV genome expressing the structural proteins NS3, NS4A, NS4B, NS5A, and NS5B. HCV targets through which inhibitors could act to inhibit replication include the NS3 protease, the helicase/ATPase, NS5A, the NS5B-RNA dependent RNA polymerase, and the HCV IRES.

Expression of HCV IRES driven luciferase reporter activity and HCV RNA is measured to obtain indirect and direct measures of replication of HCV RNA respectively. Inhibitors of HCV replication and/or proliferation are determined by initially identifying molecules that inhibit expression of the HCV IRES driven luciferase reporter in this HCV Replicon Luciferase Assay. Cell viability assays and control cell based luciferase assays are then run on hits identified in the HCV Replicon Luciferase Assay to eliminate cytoxic compounds and non-specific compounds which act by inhibiting the luciferase enzyme. Validated inhibitors of HCV replication and/or proliferation are identified by evaluating HCV Replicon Luciferase hits that are specific and non-cytoxic and demonstrating that these compounds inhibit expression of HCV RNA using a quantitative PCR based approach (Taqman) using primers and probes specific for HCV RNA (HCV Replicon RNA Assay).

The HCV Replicon Assay may be used to predict compound efficacy in treatment and/or prevention of HCV infection as well as inhibition of HCV replication and/or proliferation. The HCV Replicon encompasses a multiplicity of viral and host targets through which an inhibitor could work to inhibit HCV Replication. Viral targets expressed in the HCV Replicon include the HCV IRES (for translation), NS3 Protease, the HCV Helicase/ATPase, NS5A phosphorylation, and the NS5B polymerase. Without being limited to theory, it is believed that the compounds of the present invention inhibit HCV replication. The compounds of the invention may inhibit replication as by acting on the IRES, NS3 protease, NS5B polymerase, Helicase/ATPase, or NS5A phosphorylation.

Thus, in another embodiment, the present invention provides pharmaceutical compositions comprising an anti-HCV effective amount of a compound of formula I, or a pharmaceutically acceptable salt or hydrate thereof, in combination with a pharmaceutically acceptable carrier or auxiliary agent.

As used herein, the terms "pharmaceutically acceptable salts" and "hydrates" refer to those salts and hydrated forms of the compound that would favorably affect the physical or pharmacokinetic properties of the compound, such as solubility, palatability, absorption, distribution, metabolism and excretion. Other factors, more practical in nature, which those skilled in the art may take into account in the selection include the cost of the raw materials, ease of crystallization, yield, stability, solubility, hygroscopicity and flowability of the resulting bulk drug.

The invention also provides a method of treating HCV infection in a mammal, preferable a human, by administering to the mammal an effective amount of a compound of the present invention, a pharmaceutically acceptable salt or hydrate thereof, or a composition as described above. The compounds of the invention may be administered alone or may be administered in combination with other approved therapeutics, such as: an interferon (pegylated or not), preferably α-interferon, ribavirin, or interferon and ribavirin, or one or more other anti-HCV agent, such as an HCV protease inhibitor, HCV polymerase inhibitor, HCV IRES inhibitor, HCV Helicase and/or ATPase inhibitor, NS5A phosphorylation inhibitor, HCV NS2 inhibitor, or other HCV life cycle inhibitor. Combination therapies with may include a compound of the invention with multiple different inhibitors of HCV life cycle (immunomodulatory agents, Toll Like Receptor modulators, antisense therapeutics etc.). The agents that comprise a combination therapy may be administered together or separately, e.g., prior to, concurrently with or following the administration of the compound of the invention or pharmaceutically acceptable salt thereof. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of wherein a compound of formula (I), or a pharmaceutically acceptable salt thereof.

The compounds of the present invention may be employed in solid or liquid form including, for example, amorphous powder or crystalline form, in solution or in suspension. They may be administered in numerous different ways, such as orally, parenterally, topically, transdermally or by inhalation. Oral administration or administration by injection is preferred. The choice of carrier and the content of active compound in the carrier are generally determined in accordance with the solubility and chemical properties of the desired product, the particular mode of administration and well established pharmaceutical practice. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

Examples of liquid carriers include syrups, peanut oil, olive oil, water, saline and the like. For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, may be used. Injectable forms must be fluid to the extent they can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. Compounds of the invention may be enclosed in hard or soft shell gelatin capsules, or compressed into tablets. Examples of oral liquid dosage forms include solutions, suspensions, syrups, emulsions, soft gelatin capsules and the like. Carriers for oral use (solid or liquid) may include time delay materials known in the art, such as glyceryl monostearate or glyceryl distearate alone or with a wax. To prepare a capsule, it may be advantageous to use lactose and a liquid carrier, such as high molecular weight polyethylene glycols.

Compositions and dosage forms prepared in accordance with the present invention optionally may contain lactose, sodium citrate, calcium carbonate, dicalcium phosphate and disintegrating agents such as starch, alginic acids and certain complex silica gels combined with lubricants such as magnesium stearate, sodium lauryl sulfate and talc may be used for preparing tablets, capsules and the like. Various other materials may be present as coatings or to otherwise modify the physical form of the dosage unit. For instance, tablets, and capsules may be coated with shellac, sugar or both. When aqueous suspensions are used they may contain emulsifying agents or agents which facilitate suspension. Diluents such as sucrose, ethanol, polyols such as polyethylene glycol, propylene glycol and glycerol, and mixtures thereof also may be used. In addition, the active compound may be incorporated into sustained-release preparations and formulations. If desired, certain sweetening and/or flavoring and/or coloring agents may be added. Other suitable vehicles or carriers for the above noted formulations and compositions can be found in standard pharmaceutical texts, e.g. in "Remington's Pharmaceutical Sciences", The Science and Practice of Pharmacy, 19.sup.th Ed. Mack Publishing Company, Easton, Pa., (1995).

When these compounds or their pharmaceutically acceptable salts are formulated together with a pharmaceutically acceptable carrier, the resulting composition may be administered in vivo to mammals, such as man, to treat or prevent HCV virus infection. Such treatment may also be achieved using a compound of this invention in combination with other anti-viral agents which include, but are not limited to a-interferon and ribavirin. The additional agents may be combined with compounds of this invention to create a single dosage form. Alternatively these additional agents may be separately administered to a mammal as part of a multiple dosage form.

EXAMPLES

General Methods

Reaction solvents were commercially purchased from Aldrich or Acros without further purification and reagents were used as received. Reaction was monitored by thin-layer chromatography (TLC) on 0.25 mm precoated Merck Silica Gel 60 F$_{254}$, visualizing with ultraviolet light. Flash column chromatography was performed on Merck Silica Gel 60 (230-400 mesh) using reagent grade hexanes, dichloromethane, and ACS grade ethyl acetate, and methanol. LC-MS was performed on Water Separation. $^1$H and $^{13}$C NMR spectra were recorded on a Varian Unity INPVA 500 MHz spectrometer, CDCl$_3$ as solvent, TMS as internal reference. $^1$H-$^1$H coupling are assumed to be first order, and peak multiplicity is reported as a s (single), d (doublet), t (triplet), q (quartet), m (multiplet), or b (broad).

Example 1

General Procedure for Synthesis of Pyrazole 8, 9D~20D

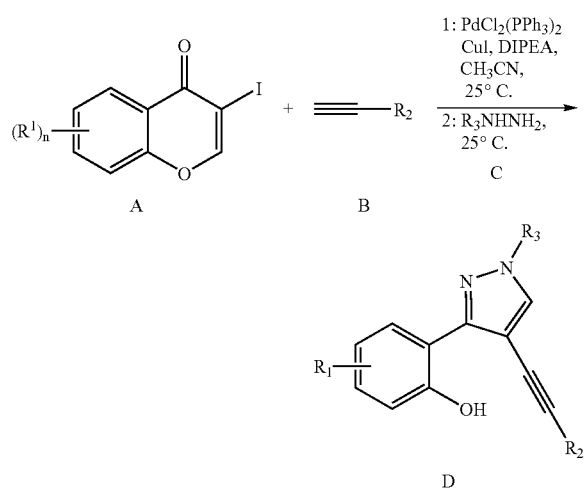

A mixture of iodochromone A (0.5 mmol), acetylene B (0.6 mmol), copper (I) iodide (0.01 mmol), and dichloribis(triphenylphosphine)palladium (0.005 mmol) in CH$_3$CN (6 ml) was added with DIEPA (2 mmol) and then stirred for 5 h at room temperature. The reaction mixture was treated with hydrazine C (1 mmol) and stirred at RT overnight. After evaporation, the crude product was directly purified by a flash column chromatography to give the pure product.

Compound 8

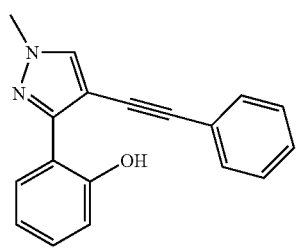

Purification by a flash chromatography (Hexanes/EtOAc=2/1) gave 8 in 92% yield. $^1$H NMR: δ 10.70 (s, 1H), 8.58 (dd, J=8.0, 1.5 Hz, 1H), 7.65 (s, 1H), 7.55 (dd, J=7.5, 1.5 Hz, 2H), 7.36 (m, 3H), 7.26 (m, 1H), 7.05 (dd, J=8.5, 1.5 Hz, 1H), 6.97 (td, J=7.5, 1.5 Hz), 3.97 (s, 3H); $^{13}$C NMR: δ 155.9, 150.4, 134.5, 131.2, 129.7, 128.4, 128.2, 127.1, 123.4, 119.1, 116.9, 116.7, 100.8, 92.6, 81.4, 39.3. LC-MS: m/z, 275 (M+1).

Compound 9D

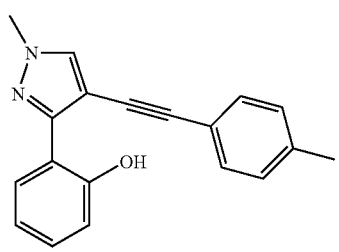

Purification by a flash chromatography (Hexanes/EtOAc=2/1) gave 9D in 72% yield. $^1$H NMR: δ 10.71 (s, 1H), 8.58 (dd, J=8.0, 1.5 Hz, 1H), 7.58 (s, 1H), 7.42 (d, J=7.5 Hz, 2H), 7.25 (m, 1H), 7.17 (d, J=7.5 Hz, 2H), 7.04 (dd, J=8.0, 1.0 Hz, 1H), 6.94 (td, J=7.0, 1.0 Hz), 3.97 (s, 3H), 2.37 (s, 3H); $^{13}$C NMR: δ 155.9, 150.3, 138.4, 134.4, 131.1, 129.6, 129.2, 127.1, 120.3, 119.1, 116.9, 116.7, 100.9, 92.7, 80.7, 39.2, 21.5. LC-MS: m/z, 289 (M+1).

Compound 10D

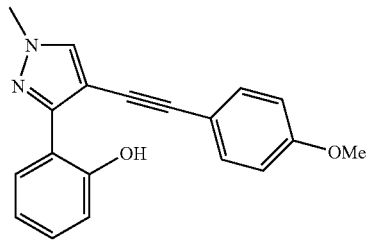

Purification by a flash chromatography (Hexanes/EtOAc=2/1) gave 10D in 78% yield. $^1$H NMR: δ 10.72 (s, 1H), 8.57 (dd, J=7.5, 1.0 Hz, 1H), 7.58 (s, 1H), 7.46 (d, J=9.0 Hz, 2H), 7.23 (td, J=8.5, 1.5 Hz, 1H), 7.03 (d, J=8.5 Hz, 1H), 6.94 (t, J=7.5 Hz, 1H), 6.89 (d, J=9.0 Hz, 2H), 3.91 (s, 3H), 3.82 (s, 3H); $^{13}$C NMR: δ 159.6, 155.9, 150.2, 134.3, 132.7, 129.6, 127.1, 119.0, 116.9, 116.8, 115.5, 114.1, 101.1, 92.5, 79.9, 55.3, 39.2.

Compound 11D

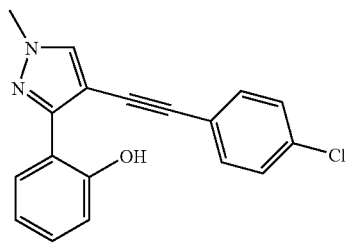

Purification by a flash chromatography (Hexanes/EtOAc=2/1) gave 11D in 63% yield. $^1$H NMR: δ 10.64 (s, 1H), 8.50 (dd, J=7.5, 1.5 Hz, 1H), 7.64 (s, 1H), 7.45 (d, J=9.0 Hz, 2H), 7.34 (d, J=9.0 Hz, 2H), 7.26 (td, J=8.5, 1.5 Hz, 1H), 7.04 (d, J=7.5 Hz, 1H), 6.96 (t, J=7.5 Hz, 1H), 3.96 (s, 3H); $^{13}$C NMR: δ 156.0, 150.6, 134.5, 134.2, 132.4, 129.8, 128.8, 127.0, 121.9, 119.1, 117.0, 116.6, 100.5, 91.5, 82.4, 39.3; LC-MS: m/z, 309 (M+1).

Compound 12D

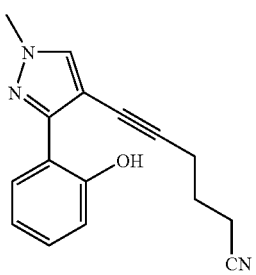

Purification by a flash chromatography (Hexanes/EtOAc=2/1) gave 12D in 54% yield. ¹H NMR: δ 10.64 (s, 1H), 8.40 (dd, J=8.0, 1.0 Hz, 1H), 7.54 (s, 1H), 7.24 (t, J=8.0 Hz, 1H), 7.02 (d, J=8.5 Hz, 1H), 6.93 (t, J=7.5 Hz, 1H), 3.92 (s, 3H), 2.67 (t, J=6.5 Hz, 2H), 2.57 (t, J=7.5 Hz, 2H), 1.99 (m, 2H); ¹³C NMR: δ 155.8, 150.2, 134.6, 129.7, 126.7, 119.1, 118.9, 117.0, 116.7, 100.6, 90.3, 74.3, 39.2, 24.6, 18.8, 16.3; LC-MS: m/z, 264 (M⁺−1).

Compound 13D

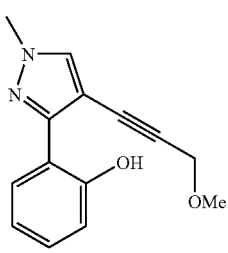

Purification by a flash chromatography (Hexanes/EtOAc=1/1) gave 13D in 74% yield. ¹H NMR: δ 10.64 (s, 1H), 8.44 (dd, J=8.0, 1.5 Hz, 1H), 7.58 (s, 1H), 7.23 (t, J=8.5 Hz, 1H), 7.02 (d, J=8.5 Hz, 1H), 6.92 (t, J=7.5 Hz, 1H), 4.38 (s, 2H), 3.92 (s, 3H), 3.47 (s, 3H); ¹³C NMR: δ 155.9, 150.5, 135.1, 129.7, 127.0, 119.0, 117.0, 116.5, 100.1, 88.6, 78.4, 60.6, 57.7, 39.2; LC-MS: m/z, 242 (M+).

Compound 14D

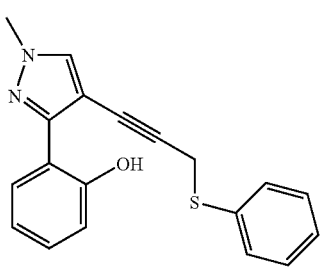

Purification by a flash chromatography (Hexanes/EtOAc=3/1) gave 14D in 67% yield. ¹H NMR: δ 10.63 (s, 1H), 8.29 (d, J=8.0 Hz, 1H), 7.50 (s, 1H), 7.48 (m, 2H), 7.33 (t, J=8.0 Hz, 2H), 7.20 (m, 2H), 7.00 (d, J=8.0 Hz, 1H), 6.77 (t, J=7.5 Hz, 1H), 3.91 (s, 2H), 3.88 (s, 3H); ¹³C NMR: δ 155.8, 150.5, 135.3, 134.8, 130.0, 129.6, 127.0, 126.9, 119.1, 116.8, 116.5, 100.3, 88.6, 75.4, 39.2, 23.9.

Compound 15D

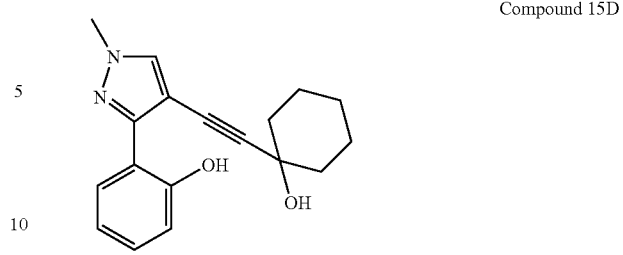

Purification by a flash chromatography (Hexanes/EtOAc=1/1) gave 15D in 84% yield. ¹H NMR: δ 10.65 (s, 1H), 8.48 (d, J=8.0 Hz, 1H), 7.50 (s, 1H), 7.23 (t, J=8.0 Hz, 1H), 7.00 (d, J=8.0 Hz, 1H), 6.88 (t, J=7.5 Hz, 1H), 3.86 (s, 3H), 2.35 (bs, 1H), 2.05 (m, 2H), 1.77-1.57 (bm, 8H); ¹³C NMR: δ 155.8, 150.3, 134.7, 129.6, 127.0, 118.8, 116.9, 116.6, 100.3, 96.3, 76.2, 69.4, 39.9, 39.1, 25.2, 23.3; LC-MS: m/z, 297 (M+1).

Compound 16D

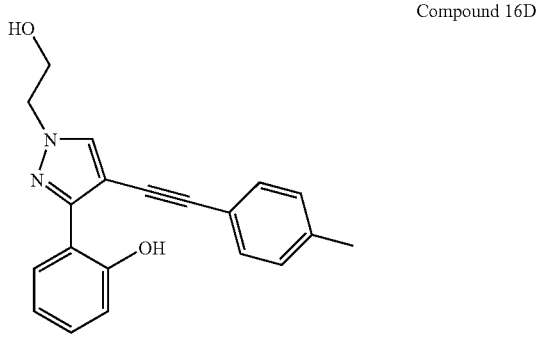

Purification by a flash chromatography (Hexanes/EtOAc=1/1) gave 16D in 82% yield. ¹H NMR: δ 10.61 (s, 1H), 8.58 (dd, J=8.5, 1.5 Hz, 1H), 7.78 (s, 1H), 7.43 (d, J=8.0 Hz, 2H), 7.28 (td, J=8.5, 1.5 Hz, 1H), 7.18 (d, J=8.0 Hz, 1H), 7.04 (d, J=8.5 Hz, 1H), 6.96 (t, J=8.0 Hz, 1H), 4.30 (t, J=5.0 Hz, 2H), 4.06 (t, J=5.0 Hz, 2H), 2.39 (s, 3H); ¹³C NMR: δ 155.8, 150.8, 138.5, 134.9, 131.2, 129.8, 129.2, 127.3, 120.2, 119.2, 116.9, 116.7, 101.1, 92.9, 80.5, 61.2, 54.6, 21.5; LC-MS: m/z, 319 (M+1).

Compound 17D

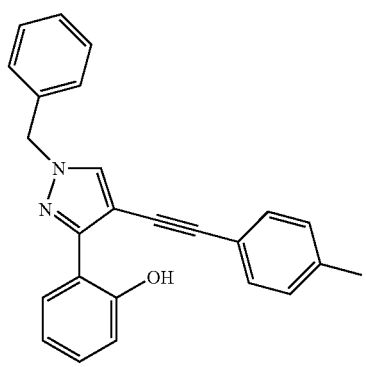

Purification by a flash chromatography (Hexanes/EtOAc=3/1) gave 17D in 43% yield. ¹H NMR: δ 10.71 (s, 1H), 8.58 (dd, J=8.0, 1.5 Hz, 1H), 7.63 (s, 1H), 7.38 (bm, 5H), 7.27 (m, 3H), 7.16 (d, J=7.5 Hz, 2H), 7.03 (d, J=8.0 Hz, 1H), 6.94 (t, J=7.0 Hz, 1H), 5.31 (s, 2H), 2.37 (s, 3H); $^{13}$C NMR: δ 156.0, 150.4, 138.4, 134.9, 133.7, 131.1, 129.7, 129.2, 129.1, 128.7, 128.0, 127.2, 120.2, 119.1, 116.9, 116.7, 101.3, 92.9, 80.6, 56.4, 21.5.

Compound 18D

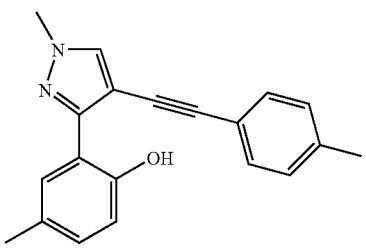

Purification by a flash chromatography (Hexanes/EtOAc=3/1) gave 18D in 57% yield. $^1$H NMR: δ 10.49 (s, 1H), 8.43 (d, J=2.0 Hz, 1H), 7.59 (s, 1H), 7.43 (d, J=8.0 Hz, 2H), 7.17 (d, J=8.0 Hz, 2H), 7.05 (d, J=8.0, 2.0 Hz, 1H), 6.93 (d, J=7.5 Hz, 1H), 3.92 (s, 3H), 2.37 (s, 3H), 2.34 (s, 3H); $^{13}$C NMR: δ 153.7, 150.4, 138.3, 134.2, 130.9, 130.3, 129.2, 127.9, 127.5, 120.4, 116.6, 116.3, 100.9, 92.8, 81.0, 39.2, 21.5, 20.8.

Compound 19D

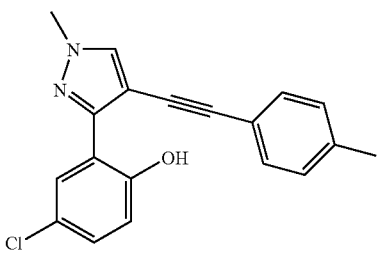

Purification by a flash chromatography (Hexanes/EtOAc=2/1) gave 19D in 67% yield. $^1$H NMR: δ 10.69 (s, 1H), 8.70 (d, J=2.5 Hz, 1H), 7.62 (s, 1H), 7.49 (d, J=8.0 Hz, 2H), 7.19 (m, 3H), 6.97 (d, J=8.0 Hz, 1H), 3.93 (s, 3H), 2.37 (s, 3H); $^{13}$C NMR: δ 154.6, 149.0, 138.5, 134.1, 131.0, 129.3, 129.2, 126.6, 123.8, 120.0, 118.2, 117.8, 101.4, 93.7, 80.2, 39.3, 21.5.

Compound 20D

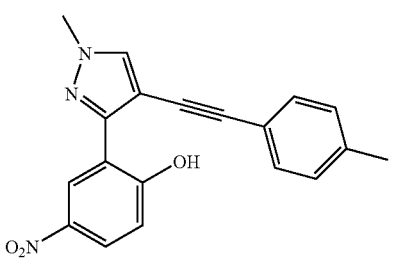

Purification by a flash chromatography (Hexanes/EtOAc=2/1) gave 20D in 90% yield. $^1$H NMR: δ 11.63 (s, 1H), 9.70 (s, 1H), 8.15 (dd, J=9.0, 2.5 Hz, 1H), 7.66 (s, 1H), 7.58 (d, J=7.5 Hz, 2H), 7.21 (d, J=8.0 Hz, 2H), 7.06 (d, J=9.0 Hz, 1H), 3.97 (s, 3H), 2.38 (s, 3H); $^{13}$C NMR: δ 161.7, 148.1, 141.8, 138.8, 134.5, 131.4, 129.3, 125.3, 123.3, 119.7, 117.5, 116.7, 102.0, 94.8, 79.2, 39.4, 21.5.

Example 2

General Procedure for Synthesis of Pyrazolo[3,4]benzopyran 1E~12E

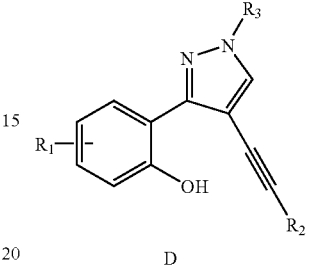

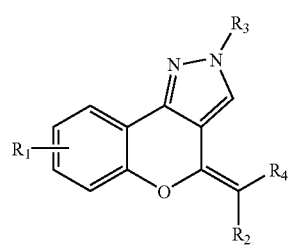

To a mixture of Pd$_2$(dba)$_3$ (0.01 mmol), Bpy (0.02 mmol), K$_2$CO$_3$ (0.8 mmol) and ArI (0.4 mmol) in DMF (3 mL) was added with the DMF (1 mL) solution of Pyrazole D (0.2 mmol) and then stirred for overnight at 60° C. The reaction mixture was added with aq. NH$_4$Cl (10 ml) and then extracted with EtOAc (3×20 mL). The organic phase was washed by H$_2$O, brine and then dried over Na$_2$SO$_4$. After evaporation, the crude product was directly purified by a flash column chromatography to give the pure product.

Compound 1E

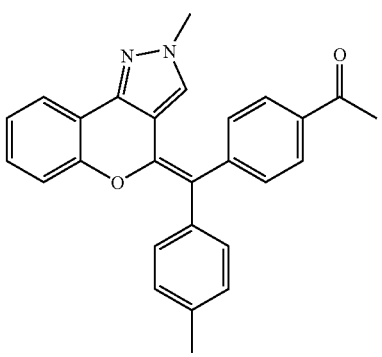

Purification by a flash chromatography (Hexanes/EtOAc=1/1) gave 1E in 74% yield. $^1$H NMR: δ 8.04 (d, J=8.5 Hz, 2H), 7.78 (dd, J=8.0, 1.5 Hz, 1H), 7.45 (d, J=8.5 Hz, 2H), 7.33 (d, J=8.0 Hz, 2H) 7.25 (td, J=9.0, 1.5 Hz, 1H), 7.12 (d, J=7.5 Hz, 2H), 7.06 (m, 2H), 5.93 (s, 1H), 3.73 (s, 3H), 2.68 (s, 3H), 2.35 (s, 3H); $^{13}$C NMR: δ 197.9, 152.5, 146.6, 143.5, 141.1, 136.1, 135.9, 135.8, 131.8, 129.5, 129.4, 129.3, 128.6, 128.0, 122.6, 121.8, 116.3, 116.0, 114.2, 111.7, 39.4, 26.7, 21.2; LC-MS: m/z, 407 (M+1).

Compound 2E

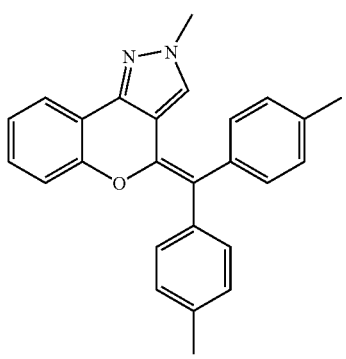

Purification by a flash chromatography (Hexanes/EtOAc=2/1) gave 2E in 78% yield. $^1$H NMR: δ 7.77 (d, J=7.5 Hz, 1H), 7.42 (d, J=6.0 Hz, 2H), 7.20 (bm, 5H) 7.10 (d, J=8.0 Hz, 2H), 7.04 (d, J=8.0 Hz, 1H), 7.01 (t, J=7.0 Hz, 1H), 5.75 (s, 1H), 3.67 (s, 3H), 2.42 (s, 3H), 2.33 (s, 3H); $^{13}$C NMR: δ 152.6, 143.3, 140.8, 138.0, 136.4, 135.3, 131.1, 130.2, 129.3, 129.2, 128.4, 128.3, 122.3, 121.6, 116.2, 114.8, 112.2, 39.1, 21.4, 21.14; LC-MS: m/z, 379 (M+1).

Compound 3E

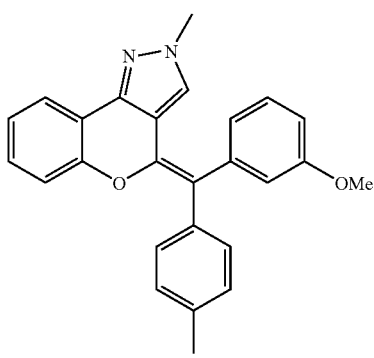

Purification by a flash chromatography (Hexanes/EtOAc=2/1) gave 3E in 74% yield. $^1$H NMR: δ 7.78 (d, J=7.5 Hz, 1H), 7.44 (d, J=8.0 Hz, 2H), 7.38 (t, J=7.5 Hz, 1H), 7.24 (m, 1H) 7.12 (d, J=7.5 Hz, 2H), 7.05 (d, J=7.5 Hz, 1H), 7.03 (t, J=7.5 Hz, 1H), 6.96 (dd, J=7.0, 1.0 Hz, 1H), 6.92 (d, J=7.5 Hz, 1H), 6.84 (s, 1H), 5.76 (s, 1H), 3.79 (s, 3H), 3.72 (s, 3H), 2.34 (s, 3H); $^{13}$C NMR: δ 160.6, 152.6, 143.3, 142.4, 140.9, 136.0, 135.5, 130.4, 129.4, 129.1, 128.5, 128.4, 123.7, 122.4, 121.7, 116.2, 116.1, 116.1, 114.7, 113.6, 112.1, 55.3, 39.2, 21.1; LC-MS: m/z, 395 (M+1).

Compound 4E

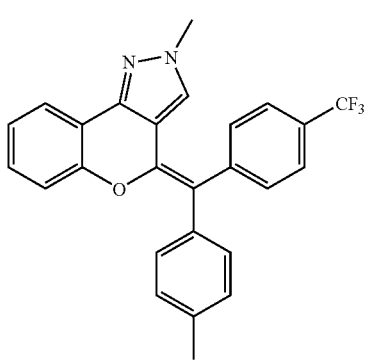

Purification by a flash chromatography (Hexanes/EtOAc=2/1) gave 4E in 72% yield. $^1$H NMR: δ 7.79 (d, J=8.0 Hz, 1H), 7.72 (d, J=7.5 Hz, 2H), 7.47 (d, J=7.5 Hz, 2H), 7.34 (d, J=8.0 Hz, 2H), 7.25 (d, J=6.0 Hz, 1H), 7.13 (d, J=7.5 Hz, 2H), 7.06 (t, J=8.0 Hz, 2H), 5.79 (s, 1H), 3.73 (s, 3H), 2.35 (s, 3H); $^{13}$C NMR: δ 152.4, 145.2, 143.5, 141.3, 135.8, 132.0, 129.5, 129.2, 128.6, 127.9, 126.4, 126.3, 122.6, 121.8, 116.2, 115.9, 113.8, 111.6, 39.3, 21.2; LC-MS: m/z, 433 (M+1).

Compound 5E

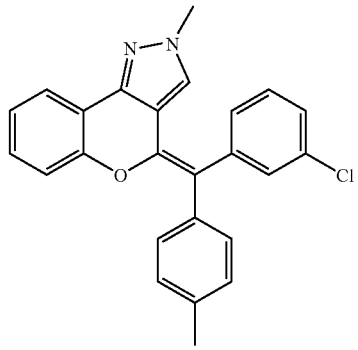

Purification by a flash chromatography (Hexanes/EtOAc=2/1) gave 5E in 80% yield. $^1$H NMR: δ 7.78 (d, J=8.0 Hz, 1H), 7.38 (m, 4H), 7.32 (s, 1H), 7.23 (m, 2H), 7.13 (d, J=8.0 Hz, 2H), 7.04 (t, J=8.0 Hz, 2H), 5.82 (s, 1H), 3.72 (s, 3H), 2.34 (s, 3H); $^{13}$C NMR: δ 152.4, 143.4, 143.0, 141.3, 135.8, 135.7, 135.1, 131.5, 130.7, 129.7, 129.4, 129.2, 128.6, 128.1, 127.7, 122.5, 121.7, 116.2, 116.0, 113.7, 111.7, 39.3, 21.2; LC-MS: m/z, 399 (M+1).

Compound 6E

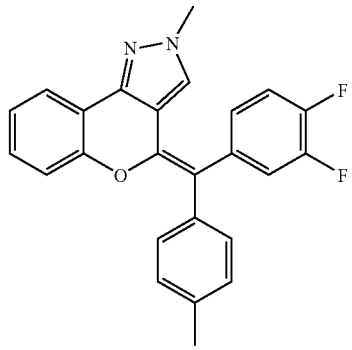

Purification by a flash chromatography (Hexanes/EtOAc=2/1) gave 6E in 62% yield. $^1$H NMR: δ 7.79 (d, J=7.5 Hz, 1H), 7.35 (d, J=7.0 Hz, 2H), 7.24 (t, J=8.5 Hz, 2H), 7.13 (m, 3H), 7.04 (m, 3H), 5.92 (s, 1H), 3.77 (s, 3H), 2.34 (s, 3H); $^{13}$C NMR: δ 152.4, 152.0 (d, J=12.8 Hz), 150.9 (d, J=12.8 Hz), 149.9 (d, J=12.8 Hz), 148.9 (d, J=12.3 Hz), 143.4, 141.4, 138.0 (t, J=5.0 Hz), 135.8, 135.7, 129.5, 129.0, 128.6, 127.7, 127.7 (t, J=3.0 Hz), 122.6, 121.7, 120.3 (d, J=15.5 Hz), 118.2 (d, J=16.5 Hz), 116.2, 115.9, 113.0, 111.6, 39.3, 21.1; LC-MS: m/z, 401 (M+1).

Compound 7E

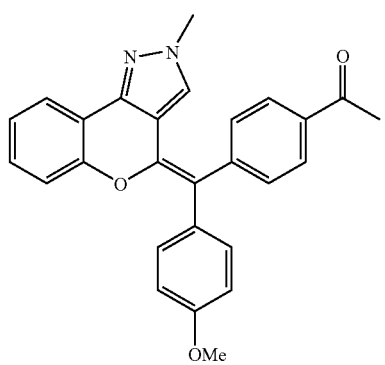

Purification by a flash chromatography (Hexanes/EtOAc=3/1) gave 7E in 78% yield. $^1$H NMR: δ 8.06 (d, J=8.0 Hz, 2H), 7.79 (d, J=6.5 Hz, 1H), 7.45 (d, J=8.0 Hz, 2H), 7.38 (d, J=7.0 Hz, 2H), 7.25 (t, J=8.5 Hz, 1H), 7.06 (t, J=8.0 Hz, 2H), 6.86 (d, J=7.0 Hz, 2H), 5.92 (s, 1H), 3.82 (s, 3H), 3.72 (s, 3H), 2.68 (s, 3H); $^{13}$C NMR: δ 197.9, 157.8, 152.5, 146.7, 143.4, 140.6, 136.1, 131.8, 131.4, 130.6, 129.5, 129.4, 127.9, 122.6, 121.8, 116.2, 116.0, 113.9, 113.3, 111.7, 55.2, 39.4, 26.7; LC-MS: m/z, 423 (M+1).

Compound 8E

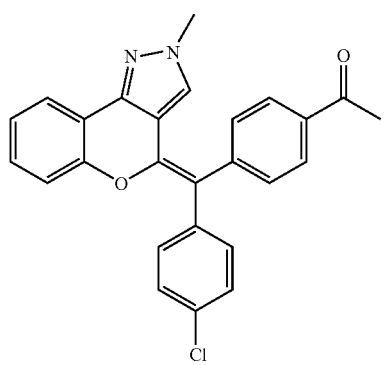

Purification by a flash chromatography (Hexanes/EtOAc=3/1) gave 8E in 50% yield. $^1$H NMR: δ 8.06 (d, J=7.5 Hz, 2H), 7.81 (d, J=7.5 Hz, 1H), 7.44 (d, J=7.0 Hz, 2H), 7.37 (d, J=7.0 Hz, 2H), 7.28 (m, 2H), 7.09 (t, J=7.5 Hz, 1H), 7.05 (d, J=8.6 Hz, 1H), 5.95 (s, 1H), 3.74 (s, 3H), 2.68 (s, 3H); $^{13}$C NMR: δ 197.7, 152.2, 146.0, 143.5, 142.0, 137.3, 136.3, 131.8, 131.6, 130.7, 129.6, 129.5, 128.2, 128.0, 122.8, 121.9, 116.2, 115.9, 112.9, 111.3, 39.4, 26.7; LC-MS: m/z, 427 (M+1).

Compound 9E

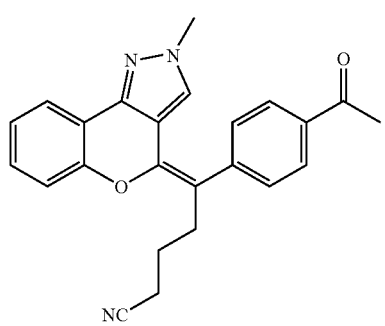

Purification by a flash chromatography (Hexanes/EtOAc=2/1) gave 9E in 68% yield. $^1$H NMR: δ 8.02 (d, J=8.0 Hz, 2H), 7.75 (d, J=7.5 Hz, 1H), 7.36 (d, J=7.5 Hz, 2H), 7.26 (t, J=7.5 Hz, 1H), 7.17 (d, J=7.5 Hz, 1H), 7.04 (t, J=8.0 Hz, 1H), 6.07 (s, 1H), 3.70 (s, 3H), 2.80 (t, J=7.5 Hz, 2H), 2.65 (s, 3H), 2.42 (t, J=7.5 Hz, 2H), 1.77 (m, 2H); $^{13}$C NMR: δ 197.7, 152.6, 145.8, 143.1, 141.6, 136.2, 130.2, 129.6, 129.4, 127.5, 122.5, 121.8, 119.9, 116.1, 115.8, 111.8, 110.6, 39.3, 30.3, 26.7, 23.8, 16.6; LC-MS: m/z, 384 (M+1).

Compound 10E

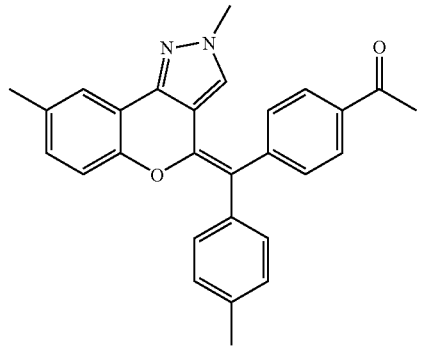

Purification by a flash chromatography (Hexanes/EtOAc=2/1) gave 10E in 52% yield. $^1$H NMR: δ 8.04 (d, J=8.0 Hz, 2H), 7.60 (s, 1H), 7.44 (d, J=7.5 Hz, 2H), 7.33 (d, J=8.0 Hz, 2H), 7.11 (d, J=8.0 Hz, 2H), 7.05 (d, J=8.5 Hz, 1H), 6.94 (d, J=8.0 Hz, 1H), 5.91 (s, 1H), 3.71 (s, 3H), 2.67 (s, 3H), 2.34 (s, 3H), 2.33 (s, 3H); $^{13}$C NMR: δ 197.9, 150.5, 146.8, 143.6, 141.3, 136.0, 136.0, 135.7, 132.0, 131.8, 130.2, 129.4, 129.3, 128.6, 128.5, 128.0, 121.9, 115.9, 115.5, 113.9, 111.7, 39.3, 26.7, 21.2, 20.7; LC-MS: m/z, 421 (M+1).

Compound 11E

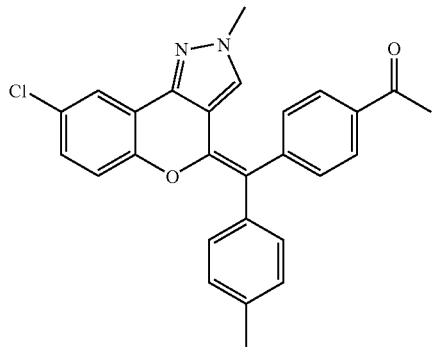

Purification by a flash chromatography (Hexanes/EtOAc=2/1) gave 11E in 91% yield. $^1$H NMR: δ 8.05 (d, J=7.0 Hz, 2H), 7.76 (s, 1H), 7.44 (d, J=7.5 Hz, 2H), 7.31 (d, J=8.0 Hz, 2H), 7.18 (d, J=8.5 Hz, 1H), 7.12 (d, J=8.0 Hz, 2H), 6.96 (d, J=7.5 Hz, 1H), 5.92 (s, 1H), 3.73 (s, 3H), 2.68 (s, 3H), 2.35 (s, 3H); $^{13}$C NMR: δ 197.8, 150.9, 146.3, 142.4, 140.6, 136.2, 136.1, 135.6, 131.6, 129.4, 129.3, 129.2, 128.6, 128.1, 127.7, 121.5, 117.5, 117.4, 114.8, 111.8, 39.4, 26.7, 21.2; LC-MS: m/z, 441 (M+1).

Compound 12E

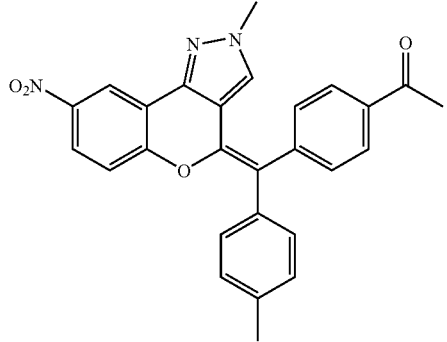

Purification by a flash chromatography (Hexanes/EtOAc=1/1) gave 12E in 81% yield. $^1$H NMR: δ 8.66 (s, 1H), 8.12 (d, J=8.0 Hz, 1H), 8.07 (d, J=7.5 Hz, 2H), 7.45 (d, J=6.5 Hz, 2H), 7.29 (d, J=8.0 Hz, 2H), 7.15 (d, J=7.0 Hz, 2H), 7.07 (d, J=8.5 Hz, 1H), 5.98 (s, 1H), 3.76 (s, 3H), 2.69 (s, 3H), 2.37 (s, 3H); $^{13}$C NMR: δ 197.7, 156.7, 145.6, 142.9, 141.4, 140.0, 136.7, 136.4, 135.1, 131.4, 129.5, 129.4, 128.8, 128.2, 124.9, 117.9, 116.8, 116.8, 111.6, 39.6, 26.7, 21.2; LC-MS: m/z, 452 (M+1).

Example 3

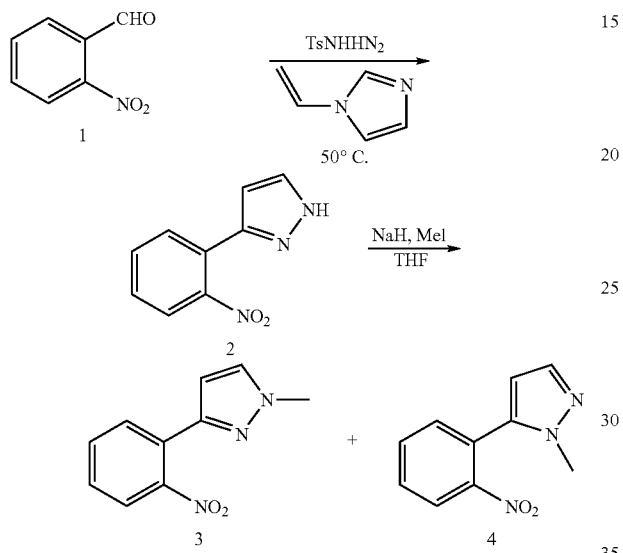

Procedure for Synthesis of 2.

The aldehyde 1 (1.5 mmol) was added to a solution of p-Toluenesulfonyl hydrazide (1.5 mmol) in acetonitrile (250 mL). After the mixture was stirred for 3 h at room temperature, a solution of 5 N NaOH (1.5 mmol) was added and the mixture was stirred for a further 20 min. The N-vinylimidazole (7.5 mmol) was added, and the mixture was stirred at 50° C. for 2 days. The volatiles were evaporated under reduced pressure, and the residue was dissolved in a 1:1 mixture of H$_2$O-EtOAc (70 mL). The organic layer was separated and dried over Na$_2$SO$_4$. After filtration and removal of the solvent under reduced pressure, the crude material was purified by flash chromatography on silica gel to give pure product 2 in 40% yield.

$^1$H NMR: δ 7.71 (d, J=8 Hz, 1H), 7.69 (d, J=8 Hz, 1H), 7.59 (d, J=2.5 Hz, 1H), 7.58 (t, J=7.5 Hz, 1H), 7.47 (t, J=7.5 Hz, 1H), 6.47 (d, J=2.5 Hz, 1H). LC-MS: (4.01 min, m/z, ES$^+$): calcd: 189.05. Found: 190.08.

Procedure for Synthesis of 3 and 4.

To the suspension of NaH (1.15 mmol) in dry THF (2 mL), 2 (0.53 mmol) in THF (3 mL) was added dropwise. After added up, the given mixture was stirred for 20 min at room temperature and then iodomethane (2.57 mmol) was added slowly. Stirred overnight, the reaction was quenched with H$_2$O and extracted with EtOAc. After removal of the solvent, the residue was purified by flash chromatography to afford 3 (49% yield) and 4 (22% yield).

3: $^1$H NMR: δ 7.73 (d, J=8 Hz, 1H), 7.69 (d, J=8 Hz, 1H), 7.57 (t, J=7.0 Hz, 1H), 7.43 (t, J=7.0 Hz, 1H), 7.39 (d, J=2.5 Hz, 1H), 6.38 (d, J=2.5 Hz, 1H), 3.94 (s, 3H). LC-MS: (4.44 min, m/z, ES$^+$): calcd: 203.07. Found: 204.06.

4: $^1$H NMR: δ 8.08 (d, J=8.5 Hz, 1H), 7.71 (t, J=7.5 Hz, 1H), 6.64 (t, J=8.5 Hz, 1H), 7.54 (d, J=1.5 Hz, 1H), 7.45 (d, J=7.0 Hz, 1H), 6.25 (d, J=2.0 Hz, 1H), 3.70 (s, 3H). LC-MS: (4.40 min, m/z, ES$^+$): calcd: 203.07. Found: 204.06.

Example 4

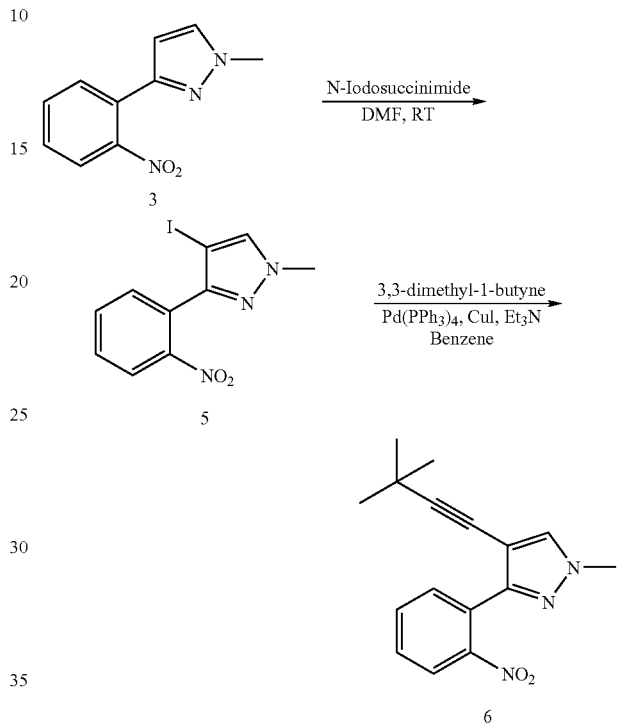

General Procedure for Synthesis of 5.

The mixture of 3 (2.94 mmol) and N-Iodosuccinimide (4.41 mmol) in DMF (5.0 mL) was stirred for 3 days at room temperature. The DMF was removed in vacuo, the residue was dissolved in EtOAc and washed with Na$_2$SO$_3$, brine and dried over MgSO$_4$. After removal of the solvent, the residue was purified by flash chromatography on silica gel (eluent: EtOAc/Petroleum=1:3) to give 5 in 84% yield.

$^1$H NMR: δ 7.99 (d, J=8.0 Hz, 1H), 7.65 (t, J=8.0 Hz, 1H), 7.55 (d, J=8.0 Hz, 1H), 7.55 (t, J=8.0 Hz, 1H), 7.49 (s, 1H), 3.94 (s, 3H). LC-MS: (4.63 min, m/z, ES$^+$): calcd: 328.97. Found: 329.93.

General Procedure for Synthesis of 6.

To a degassed solution of 5 (0.15 mmol), CuI (0.003 mmol) and Et$_3$N (0.6 mmol) in dry benzene (1 mL), Pd(PPh$_3$)$_4$ (0.015 mmol) and 3,3-Dimethyl-1-butyne (0.6 mmol) was added sequentially at room temperature and the reaction mixture was stirred overnight. The reaction mixture was filtered over Celite and washed with EtOAc. After removal of the solvent, the residue was purified by flash chromatography on silica gel (eluent: EtOAc/petroleum ether=1:3) to give 6 in 88% yield.

$^1$H NMR: δ 7.91 (d, J=8.0 Hz, 1H), 7.76 (d, J=8.0 Hz, 1H), 7.61 (t, J=8.0 Hz, 1H), 7.49 (t, J=8.0 Hz, 1H), 7.45 (s, 1H), 3.81 (s, 3H), 1.22 (s, 9H). LC-MS: (5.45 min, m/z, ES$^+$): calcd: 283.13. Found: 284.07.

Example 5

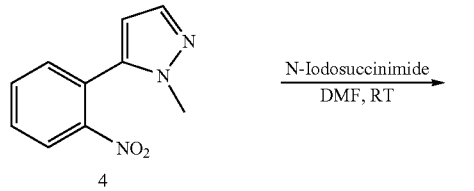

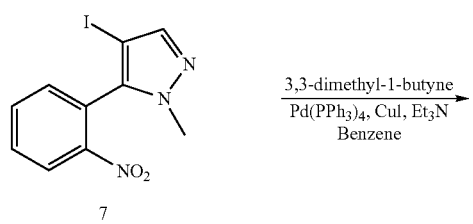

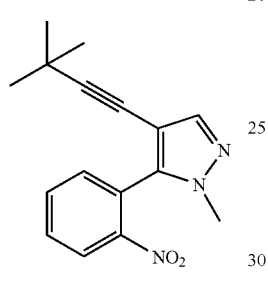

Procedure for Synthesis of 7.

7 was synthesized in 80% yield by similar procedure as of 5.

$^1$H NMR: δ 8.18 (d, J=8.0 Hz, 1H), 7.76 (t, J=8.0 Hz, 1H), 7.69 (t, J=8.0 Hz, 1H), 7.52 (s, 1H), 7.38 (d, J=8.0 Hz, 1H), 3.72 (s, 3H). LC-MS: (4.62 min, m/z, ES$^+$): calcd: 328.97. Found: 329.93.

Procedure for Synthesis of 8A.

8A was synthesized in 86% yield by similar procedure as of 6.

$^1$H NMR: δ 8.11 (d, J=8.5 Hz, 1H), 7.11 (t, J=7.5 Hz, 1H), 7.63 (t, J=8.0 Hz, 1H), 7.51 (s, 1H), 7.44 (d, J=8.0 Hz, 1H) 3.69 (s, 3H), 1.07 (s, 9H). LC-MS: (5.45 min, m/z, ES$^+$): calcd: 283.13. Found: 284.07.

Example 6

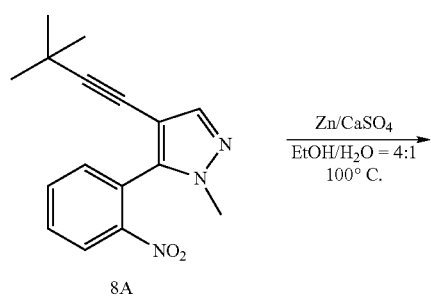

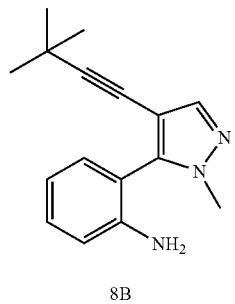

General Procedure for Synthesis of 8B.

A solution of 8A (0.16 mmol), zinc dust (0.8 mmol) and CaSO$_4$ (0.8 mmol) in 4:1 ethanol/H$_2$O (2 mL) was refluxed for 3 h. The reaction mixture was filtered over Celite and washed with 4:1 ethanol/H$_2$O. The filtrate was concentrated in vacuo and the residue was purified by flash chromatography on silica gel (eluent: EtOAc:Petroleum ether=1:3) to afford pure product 8B in 92% yield.

$^1$H NMR: δ 7.59 (s, 1H), 7.23 (t, J=6.5 Hz, 1H), 7.11 (d, J=7.0 Hz, 1H), 6.82 (t, J=6.5 Hz, 1H), 6.79 (d, J=8.5 Hz, 1H), 3.80 (br, 2H), 3.72 (s, 3H), 1.18 (s, 9H). $^{13}$C NMR: δ 145.418, 142.861, 141.149, 131.373, 130.602, 118.385, 116.133, 114.578, 103.843, 101.117, 70.265, 37.714, 31.199, 28.229. LC-MS: (5.12 min, m/z, ES$^+$): calcd: 253.16. Found: 254.14.

Example 7

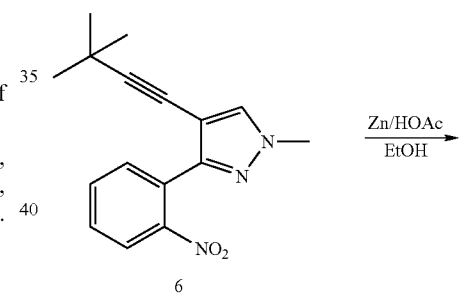

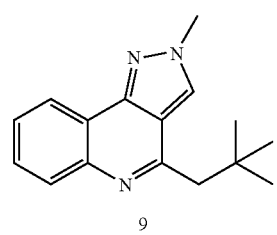

Procedure for Synthesis of 9.

A solution of 6 (0.06 mmol) in EtOH (1 mL) was added to a solution of zinc dust (3.07 mmol) and acetic acid (1.5 mL). The reaction mixture was stirred overnight under reflux. The reaction mixture was filtered over Celite and washed with EtOAc. The filtrate was adjusted to pH 7 with 5% NaHCO$_3$, washed with H$_2$O, dried over Na$_2$SO$_4$ and taken to dryness under reduced pressure. The crude was purified flash chromatography (eluent: EtOAc/Petroleum=1:3) to give 9 in 32% yield.

$^1$H NMR: δ 8.44 (d, J=8.0 Hz, 1H), 8.08 (d, J=7.5 Hz, 1H), 8.02 (s, 1H), 7.65 (t, J=8.0 Hz, 1H), 7.55 (t, J=8.0 Hz, 1H), 4.28 (s, 3H), 3.0 (s, 2H), 1.08 (s, 9H). LC-MS: (3.56 min, m/z, ES$^+$): calcd: 253.16. Found: 254.20.

Example 10

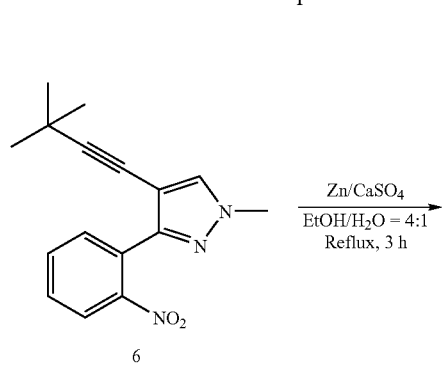

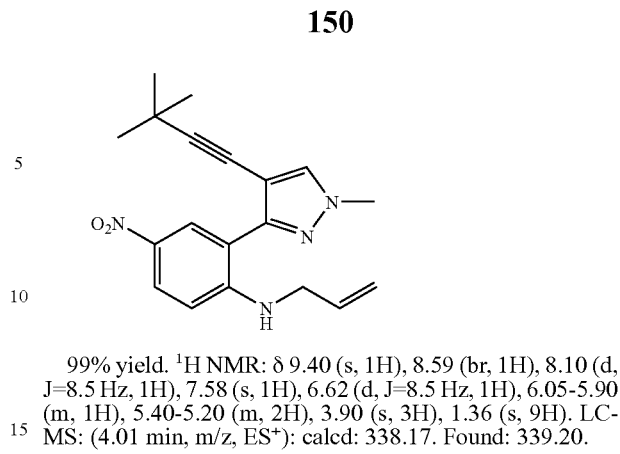

99% yield. ¹H NMR: δ 9.40 (s, 1H), 8.59 (br, 1H), 8.10 (d, J=8.5 Hz, 1H), 7.58 (s, 1H), 6.62 (d, J=8.5 Hz, 1H), 6.05-5.90 (m, 1H), 5.40-5.20 (m, 2H), 3.90 (s, 3H), 1.36 (s, 9H). LC-MS: (4.01 min, m/z, ES⁺): calcd: 338.17. Found: 339.20.

Example 12

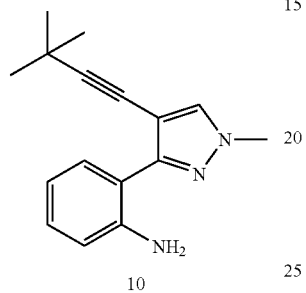

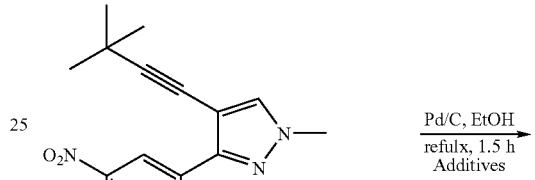

Procedure for Synthesis of 10.

Compound 10 was synthesized in 89% yield by similar procedure as of 8B.

¹H NMR: δ 8.22 (d, J=9.0 Hz, 1H), 7.48 (s, 1H), 7.13 (t, J=8.5 Hz, 1H), 6.75 (d, J=7.5 Hz, 1H), 6.74 (t, J=8.0 Hz, 1H), 5.27 (br, 1H), 3.89 (s, 3H), 1.31 (s, 9H). ¹³C NMR: δ 151.464, 145.140, 133.680, 129.608, 128.879, 116.891, 116.622, 116.327, 102.262, 100.998, 71.635, 39.346, 31.121, 28.462. LC-MS: (4.42 min, m/z, ES⁺): calcd: 253.16. Found: 254.20.

Example 11

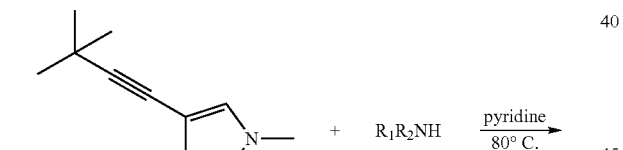

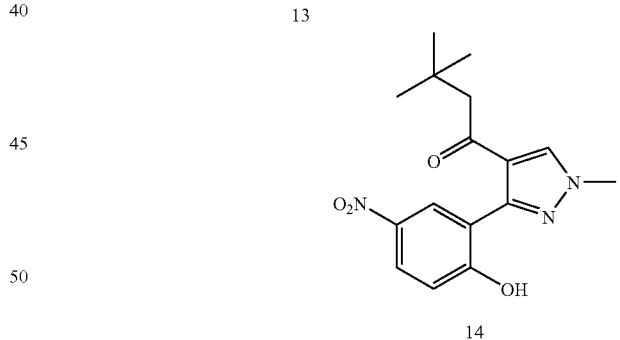

General Procedure for Synthesis of 12.

The mixture of 11 and R₁R₂NH (5 equiv.) was heated to 80° C. in Pyridine overnight. After removal of the solvent, the residue was purified by flash chromatography on silica gel (eluent: EtOAc/Petroleum ether=1:3) to give 12 as yellow solid.

Procedure for Synthesis of 13 and 14.

A mixture of 12 (0.08 mmol), 10% Pd/C and additives (CF₃SO₃H or BF₃-Et₂O, 0.08 mmol)) in absolute ethanol (1 mL) was heated to 95° C. for 1.5 h. The reaction mixture was filtered through a Celite pad and concentrated in vacuo. The residue was purified by plate chromatography (eluent: EtOAc/Petroleum ether=1:1) to give 13 (31% yield) and 14 (46% yield).

13: ¹H NMR: δ 9.36 (d, J=2.5 Hz, 1H), 8.44 (dd, J=9.0, 2.5 Hz, 1H), 8.16 (d, J=9.0 Hz, 1H), 8.12 (s, 1H), 4.32 (s, 3H), 3.02 (s, 2H), 1.18 (s, 9H). ¹³C NMR: δ 161.488, 148.072, 145.227, 130.675, 127.666, 127.502, 122.625, 119.168, 118.906, 118.734, 51.028, 40.920, 33.322, 30.626. LC-MS: (3.80 min, m/z, ES⁺): calcd: 298.14. Found: 299.19.

14: ¹H NMR: δ 11.01 (s, 1H), 9.19 (d, J=2.5 Hz, 1H), 8.17 (dd, J=9.0, 2.5 Hz, 1H), 7.99 (s, 1H), 7.08 (d, J=9.0 Hz, 1H), 4.04 (s, 3H), 2.70 (s, 2H), 1.09 (s, 9H). ¹³C NMR: δ 161.836, 148.921, 140.550, 136.261, 127.402, 126.121, 123.207, 118.137, 117.177, 54.454, 39.803, 32.097, 30.403. LC-MS: (3.81 min, m/z, ES⁺): calcd: 317.14. Found: 318.15.

Example 13

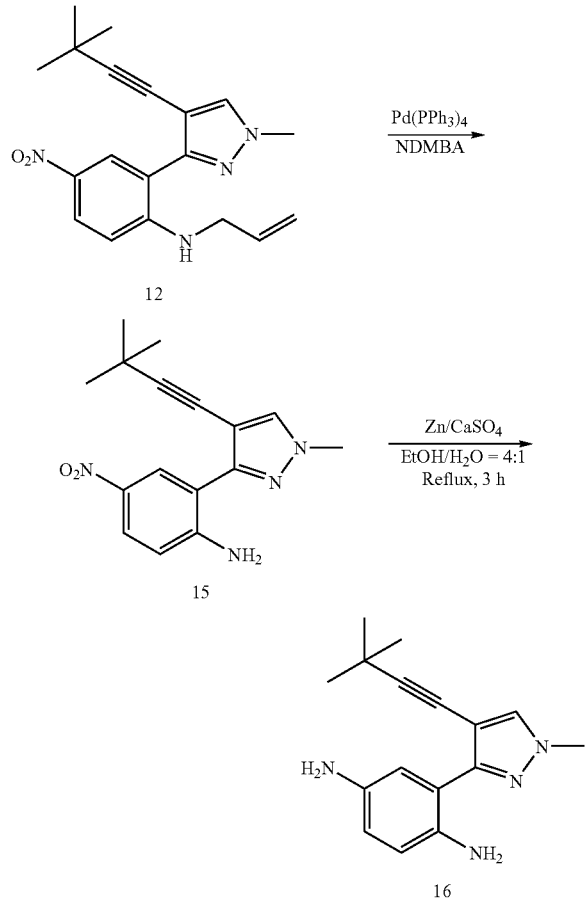

Procedure for Synthesis of 15.

To a degassed solution of 12 (19.5 mmol) and N,N'-dimethylbarbituric acid (NDMBA, 39.0 mmol) in dry CH₂Cl₂ (200 mL), Pd(PPh₃)₄ (3.9 mmol) was added quickly and the reaction mixture was heated to 35° C. and stirred overnight. After cooling, the CH₂Cl₂ was removed under vacuum and the residue was dissolved in EtOAc. The formed solution was washed with saturated Na₂CO₃, H₂O and brine and dried over Na₂SO₄. After removal of the solvent, the residue was purified by flash chromatography (eluent: EtOAc/petroleum ether=1:3) to give 15 in 62% yield.

15: ¹H NMR: δ 9.41 (d, J=2.5 Hz, 1H), 8.02 (dd, J=9.0, 2.5 Hz, 1H), 7.55 (s, 1H), 6.68 (d, J=9.0 Hz, 1H), 6.35 (br, 2H), 3.92 (s, 3H), 1.36 (s, 9H). LC-MS: (5.58 min, m/z, ES⁺): calcd: 298.14. Found: 299.19.

Procedure for Synthesis of 16.

16 was synthesized in 78% yield by similar procedure as of 8B.

¹H NMR: δ 7.62 (d, J=2.0 Hz, 1H), 7.43 (s, 1H), 6.65 (d, J=8.0 Hz, 1H), 6.59 (dd, J=8.0, 2.0 Hz, 1H), 3.81 (s, 3H), 1.56 (br, 4H), 1.32 (s, 9H). LC-MS: (3.35 min, m/z, ES⁺): calcd: 268.17. Found: 269.20.

Example 14

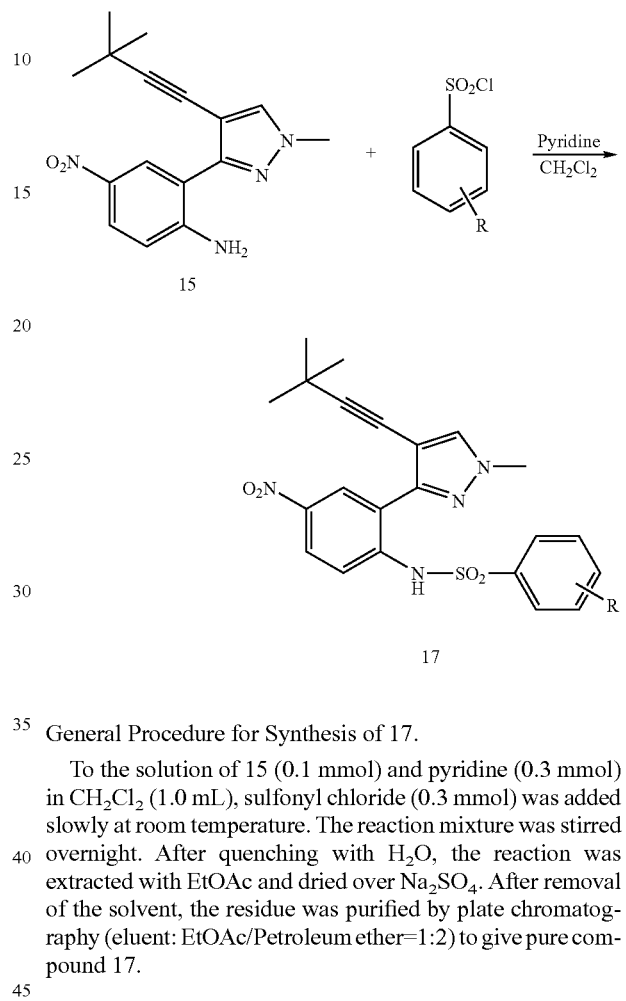

General Procedure for Synthesis of 17.

To the solution of 15 (0.1 mmol) and pyridine (0.3 mmol) in CH₂Cl₂ (1.0 mL), sulfonyl chloride (0.3 mmol) was added slowly at room temperature. The reaction mixture was stirred overnight. After quenching with H₂O, the reaction was extracted with EtOAc and dried over Na₂SO₄. After removal of the solvent, the residue was purified by plate chromatography (eluent: EtOAc/Petroleum ether=1:2) to give pure compound 17.

73% yield. ¹H NMR: δ 11.54 (s, 1H), 9.42 (d, J=2.0 Hz, 1H), 8.06 (dd, J=8.0, 2.0 Hz, 1H), 7.71 (AABB, J=8.5, 7.0 Hz, 4H), 7.57 (s, 1H), 7.22 (d, J=8.0 Hz, 1H), 4.0 (s, 3H), 2.37 (s, 3H), 1.34 (s, 9H). ¹³C NMR: δ 147.391, 144.473, 142.903, 141.177, 136.376, 134.908, 129.997, 127.444, 124.151, 124.060, 120.508, 118.494, 103.840, 103.690, 69.584, 39.816, 31.067, 28.579, 23.902, 21.796. LC-MS: (6.50 min, m/z, ES⁺): calcd: 452.15. Found: 453.11.

Example 15

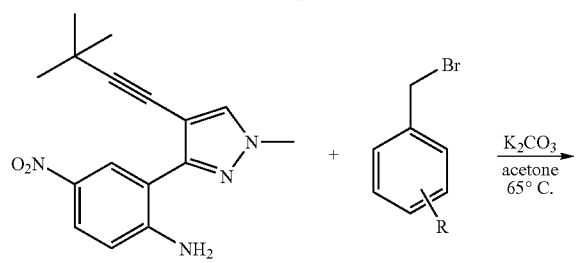

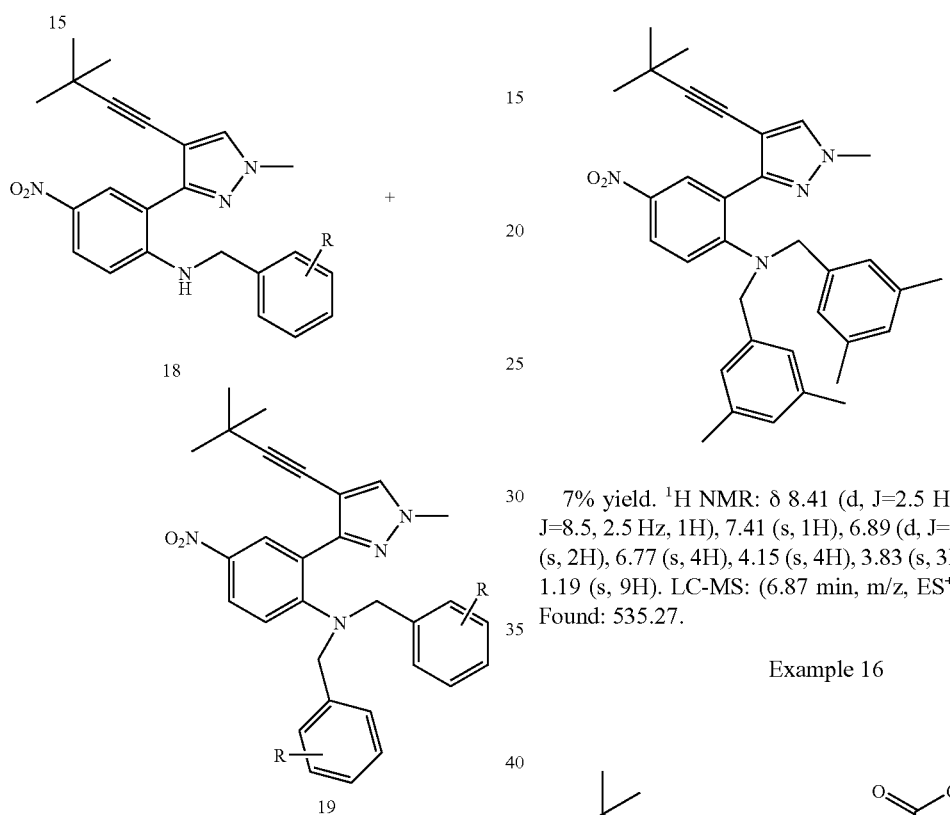

General Procedure for Synthesis of 18 and 19.

To the suspension of 15 (0.1 mmol) and K₂CO₃ (0.5 mmol) in acetone (1.0 mL), benzyl bromide (0.3 mmol) was added at room temperature. The reaction mixture was sealed and raised to 65° C. and stirred overnight. After cooled, the reaction mixture was filtered over Celite and washed with EtOAc. After removal of the solvent, the residue was purified by plate chromatography on silica gel (eluent: EtOAc/Petrpleum ether=1:3) to give pure compound 18 and 19 (in some cases, only compound 18 was isolated).

87% yield. $^1$H NMR: δ 9.45 (d, J=2.0 Hz, 1H), 8.90 (t, J=4.5 Hz, 1H), 8.07 (dd, J=9.5, 2.5 Hz, 1H), 7.56 (s, 1H), 6.99 (s, 2H), 6.94 (s, 1H), 6.62 (d, J=9.5 Hz, 1H), 4.50 (d, J=5.0 Hz, 2H), 3.88 (s, 3H), 2.32 (s, 6H), 1.37 (s, 9H). $^{13}$C NMR: δ 151.253, 149.261, 138.623, 138.071, 136.796, 134.385, 129.291, 125.763, 125.477, 124.889, 115.003, 109.970, 103.121, 102.835, 70.417, 47.593, 39.432, 31.205, 28.612, 21.581. LC-MS: (6.75 min, m/z, ES⁺): calcd: 416.22. Found: 417.19.

7% yield. $^1$H NMR: δ 8.41 (d, J=2.5 Hz, 1H), 8.17 (dd, J=8.5, 2.5 Hz, 1H), 7.41 (s, 1H), 6.89 (d, J=8.5 Hz, 1H), 6.86 (s, 2H), 6.77 (s, 4H), 4.15 (s, 4H), 3.83 (s, 3H), 2.26 (s, 12H), 1.19 (s, 9H). LC-MS: (6.87 min, m/z, ES⁺): calcd: 534.30. Found: 535.27.

Example 16

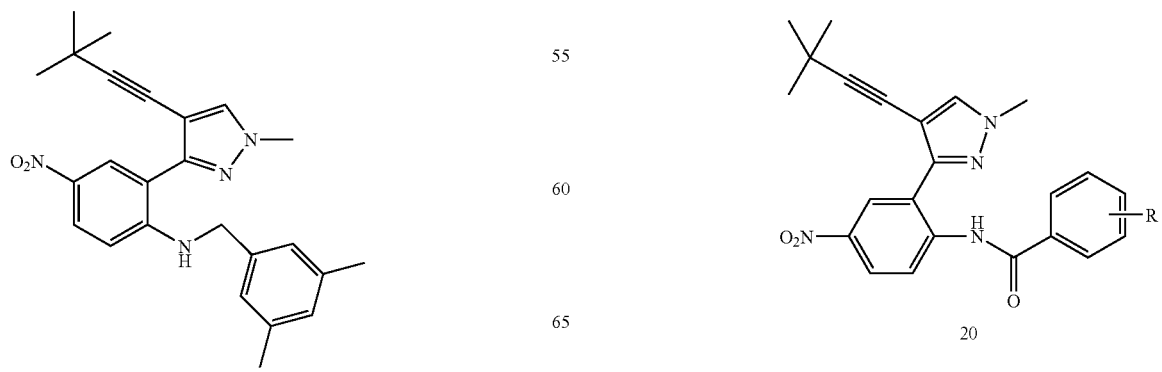

General Procedure for Synthesis of 20.

To the solution of 15 (0.1 mmol) and DMAP (0.1 mmol) in CH₂Cl₂ (1.0 mL), benzoyl chloride (0.3 mmol) was added slowly at 0° C. The reaction mixture was raised to room temperature and stirred overnight. After removal of the solvent, the residue was purified by plate chromatography (eluent: EtOAc/Petroleum ether=1:3) to give pure compound 20.

A mixture of iodochromone A (0.5 mmol), acetylene B (0.2 mmol), Copper (I) iodide (0.01 mmol), and dichloribis(triphenylphosphine)palladium (0.005 mmol) in CH₃CN (6 ml) was added with DIEPA (2 mmol) and then stirred for 5 h at room temperature. The reaction mixture was treated with methyl hydrazine (1 mmol) and stirred at RT overnight. After evaporation, the crude product was directly purified by a flash column chromatography to give the pure product.

VQ25048

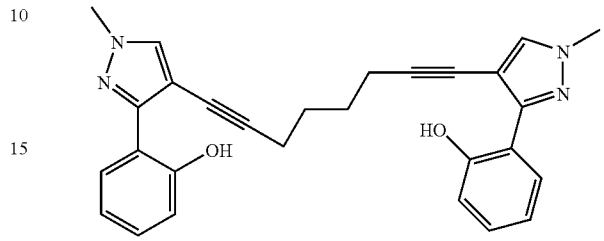

Purification by a flash chromatography (Hexanes/EtOAc=2/1) gave VQ25048. $^1$H NMR: δ 10.73 (s, 2H), 8.54 (d, J=7.5 Hz, 2H), 7.46 (s, 2H), 7.21 (m, 2H), 7.02 (d, J=8.0 Hz, 2H), 6.92 (m, 2H), 3.87 (s, 6H), 2.56 (m, 4H), 1.86 (m, 4H); LC-MS: m/z, 451 (M+1).

VQ25049

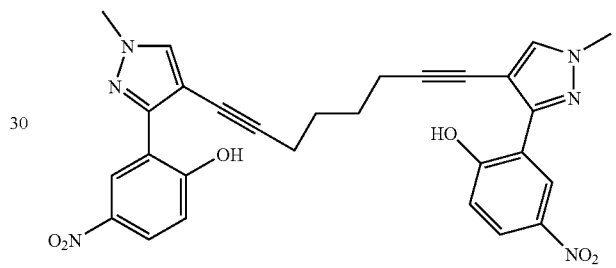

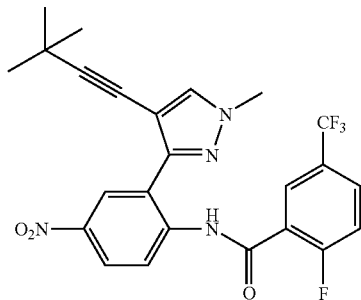

95% yield. $^1$H NMR: δ 12.25 (s, 1H), 9.38 (d, J=3.0 Hz, 1H), 8.98 (d, J=9.5 Hz, 1H), 8.45-8.3 (m, 1H), 8.24 (dd, J=9.5, 3.0 Hz, 1H), 7.9-7.75 (m, 1H), 7.60 (s, 1H), 7.34 (t, J=9.5 Hz, 1H), 3.92 (s, 3H), 1.34 (s, 9H). $^{13}$C NMR: δ 162.947, 161.162, 160.907, 147.737, 143.262, 141.331, 134.931, 130.954 (m), 129.722 (m), 128.034 (q), 124.293, 124.142, 121.591, 121.464, 117.626, 117.426, 103.898, 103.625, 69.525, 39.347, 31.065, 28.551. LC-MS: (6.85 min, m/z, ES⁺): calcd: 488.15. Found: 489.06.

Example 17

Preparation of Pyrazole Dimers

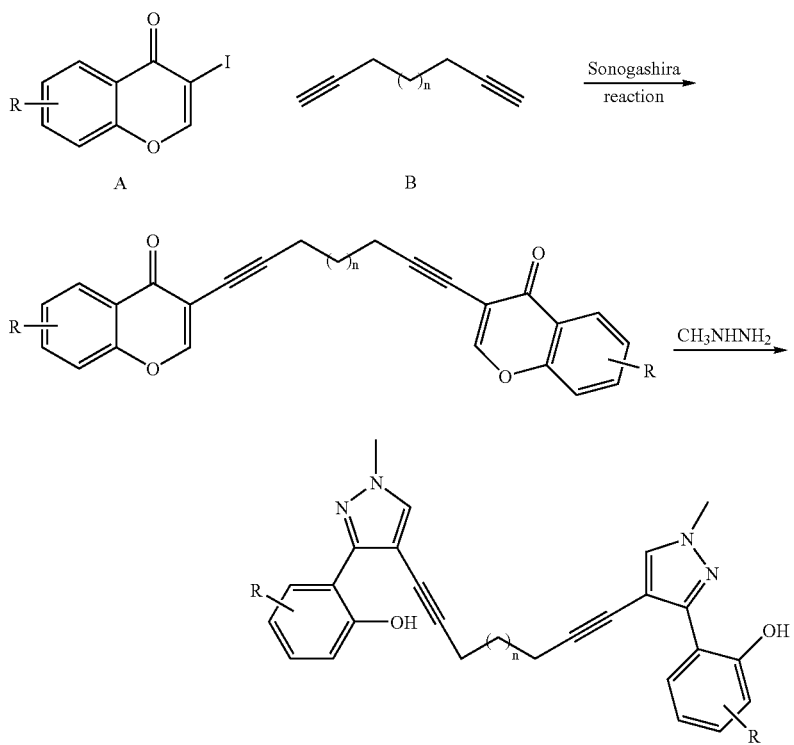

Purification by a flash chromatography (Hexanes/EtOAc=2/1) gave VQ25049. ¹H NMR: δ 11.64 (s, 2H), 9.56 (d, J=2.5 Hz, 2H), 8.03 (dd, J=3.0, 9.0 Hz, 2H), 7.58 (s, 2H), 7.00 (d, J=9.0 Hz, 2H), 3.94 (s, 6H), 2.64 (m, 4H), 1.95 (m, 4H); LC-MS: m/z, 541 (M+1).

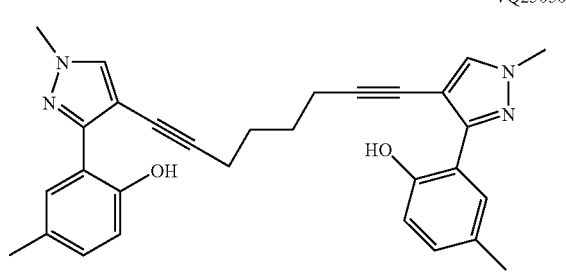
VQ25050

Purification by a flash chromatography (Hexanes/EtOAc=2/1) gave VQ25050. ¹H NMR: δ 10.52 (s, 2H), 8.32 (s, 2H), 7.45 (s, 2H), 7.02 (d, J=8.0 Hz, 2H), 6.91 (d, J=8.5 Hz, 2H), 3.89 (s, 6H), 2.56 (m, 4H), 2.97 (s, 6H), 1.89 (m, 4H); LC-MS: m/z, 479 (M+1).

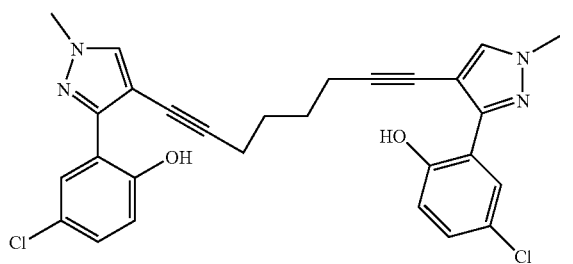
VQ25052

Purification by a flash chromatography (Hexanes/EtOAc=2/1) gave VQ25052. ¹H NMR: δ 10.72 (s, 2H), 8.56 (d, J=2.5 Hz, 2H), 7.48 (s, 2H), 7.16 (dd, J=2.5, 8.5 Hz, 2H), 6.93 (d, J=8.5 Hz, 2H), 3.90 (s, 6H), 2.58 (m, 4H), 1.92 (m, 4H); LC-MS: m/z, 519 (M⁺).

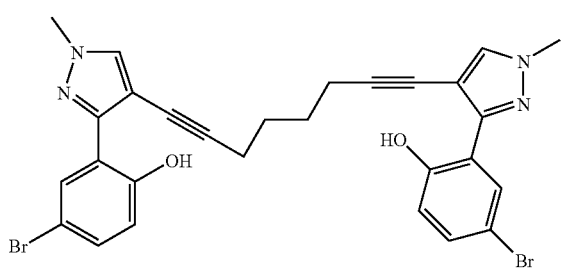
VQ25053

Purification by a flash chromatography (Hexanes/EtOAc=2/1) gave VQ25053. ¹H NMR: δ 10.75 (s, 2H), 8.69 (d, J=2.5 Hz, 2H), 7.48 (s, 2H), 7.29 (dd, J=2.0, 7.5 Hz, 2H), 6.88 (d, J=7.5 Hz, 2H), 3.90 (s, 6H), 2.59 (m, 4H), 1.94 (m, 4H); LC-MS: m/z, 609 (M+1).

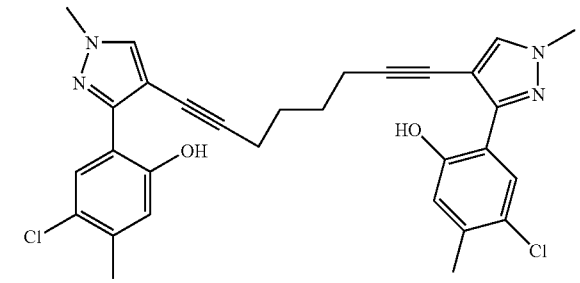
VQ25055

Purification by a flash chromatography (Hexanes/EtOAc=2/1) gave VQ25055. ¹H NMR: δ 10.60 (s, 2H), 8.53 (s, 2H), 7.47 (s, 2H), 6.87 (s, 2H), 3.89 (s, 6H), 2.58 (m, 4H), 2.34 (s, 6H), 1.93 (m, 4H); LC-MS: m/z, 547 (M+).

Example 18

General Procedure for Synthesis of Dimers

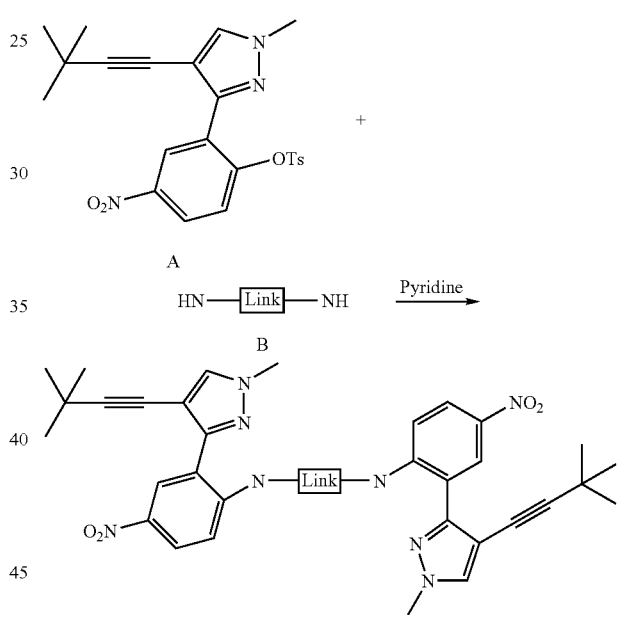

A mixture of A (0.11 mmol), B (0.055 mmol) and pyridine (1.0 mL) in a sealed tube was heated to 100° C. and stirred overnight. After removal of the solvent, the residue was purified by column chromatography (eluent: MeOH:CH₂Cl₂=1:100) to give the pure product.

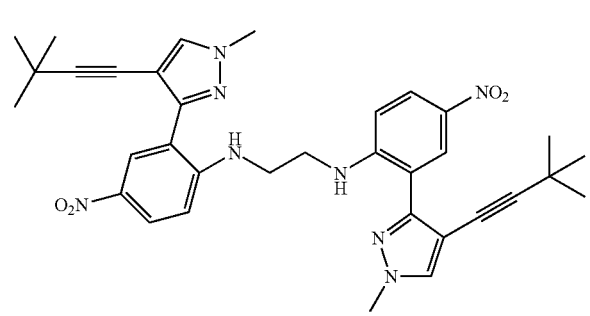

¹H NMR: δ 9.42 (d, J=3 Hz, 2H), 8.73 (br, 2H), 8.14 (dd, J=9.5, 3.0 Hz, 2H), 7.43 (s, 2H), 6.75 (d, J=9 Hz, 2H), 3.75-3.68 (m, 4H), 3.54 (s, 6H), 1.38 (s, 18H). LC-MS: (6.98 min, m/z, ES⁺): calcd: 622.30. Found: 623.26.

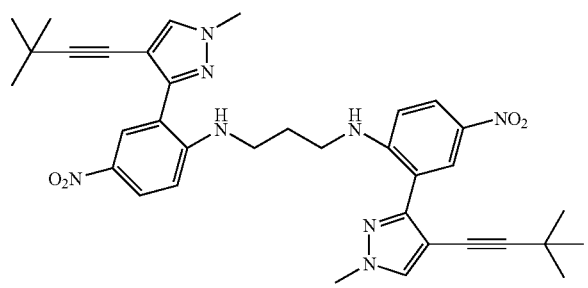

¹H NMR: δ 9.41 (d, J=3 Hz, 2H), 8.73 (t, J=5.5 Hz, 2H), 8.11 (dd, J=9.5, 3.0 Hz, 2H), 7.49 (s, 2H), 6.68 (d, J=9 Hz, 2H), 3.70 (s, 6H), 3.60-3.48 (m, 4H), 2.20-2.10 (m, 2H), 1.38 (s, 18H). LC-MS: (7.08 min, m/z, ES⁺): calcd: 636.32. Found: 637.29.

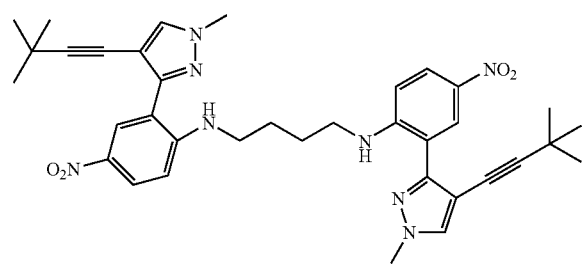

¹H NMR: δ 9.41 (d, J=3 Hz, 2H), 8.49 (t, J=5.5 Hz, 2H), 8.12 (dd, J=9.5, 3.0 Hz, 2H), 7.51 (s, 2H), 6.65 (d, J=9 Hz, 2H), 3.80 (s, 6H), 3.45-3.35 (m, 4H), 1.98-1.90 (m, 4H), 1.36 (s, 18H). LC-MS: (7.18 min, m/z, ES⁺): calcd: 650.33. Found: 651.28.

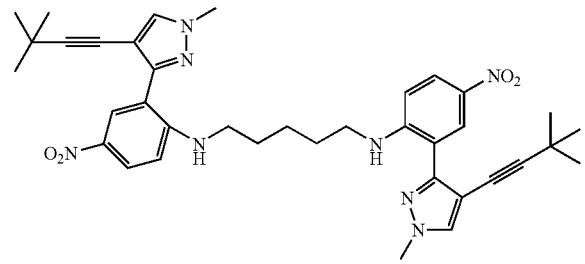

¹H NMR: δ 9.40 (d, J=3 Hz, 2H), 8.44 (t, J=5.5 Hz, 2H), 8.12 (dd, J=9.5, 3.0 Hz, 2H), 7.50 (s, 2H), 6.64 (d, J=9 Hz, 2H), 3.78 (s, 6H), 3.40-3.30 (m, 4H), 1.90-1.75 (m, 4H), 1.72-1.68 (m, 2H), 1.38 (s, 18H). LC-MS: (7.34 min, m/z, ES⁺): calcd: 664.35. Found: 665.33.

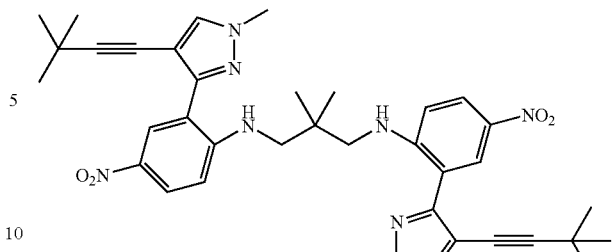

¹H NMR: δ 9.43 (d, J=3 Hz, 2H), 8.80 (t, J=5.5 Hz, 2H), 8.08 (dd, J=9.5, 3.0 Hz, 2H), 7.46 (s, 2H), 6.68 (d, J=9 Hz, 2H), 3.60 (s, 6H), 3.35 (d, J=5.5 Hz, 4H), 1.38 (s, 18H), 1.24 (s, 6H). LC-MS: (7.37 min, m/z, ES⁺): calcd: 636.35. Found: 665.41.

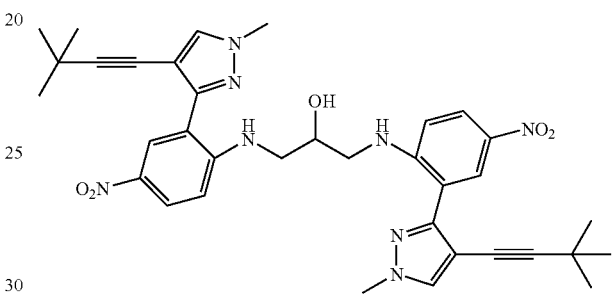

¹H NMR: δ 9.38 (d, J=3 Hz, 2H), 8.63 (br, 2H), 8.10 (dd, J=9.5, 3.0 Hz, 2H), 7.54 (s, 2H), 6.72 (d, J=9 Hz, 2H), 4.35-4.25 (m, 2H), 3.82 (s, 6H), 3.65-3.48 (m, 4H), 1.35 (s, 18H). LC-MS: (6.547 min, m/z, ES⁺): calcd: 652.31. Found: 653.36.

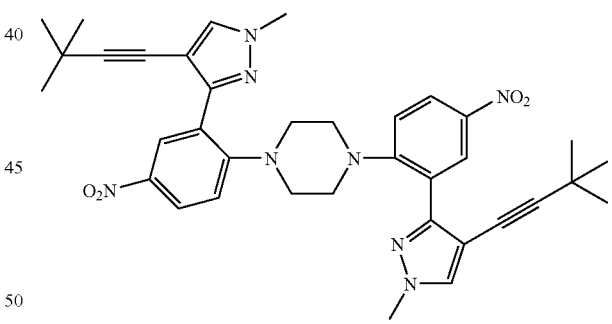

¹H NMR: δ 9.42 (d, J=3 Hz, 2H), 8.73 (br, 2H), 8.14 (dd, J=9.5, 3.0 Hz, 2H), 7.43 (s, 2H), 6.75 (d, J=9 Hz, 2H), 3.90 (s, 6H), 3.10 (s, 8H), 1.28 (s, 18H). LC-MS: (6.57 min, m/z, ES⁺): calcd: 648.32. Found: 649.32.

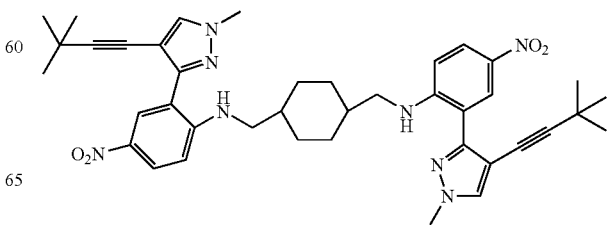

¹H NMR: δ 9.41 (d, J=3 Hz, 2H), 8.56 (t, J=5.5 Hz, 2H), 8.11 (dd, J=9.5, 3.0 Hz, 2H), 7.56 (s, 2H), 6.74 (d, J=9 Hz, 2H), 3.88 (s, 6H), 3.20 (t, J=9 Hz, 4H), 2.04-1.96 (m, 4H), 1.78-1.65 (m, 2H), 1.35 (s, 18H), 1.24-1.1 (m, 4H). LC-MS: (7.64 min, m/z, ES⁺): calcd: 704.38. Found: 705.40.

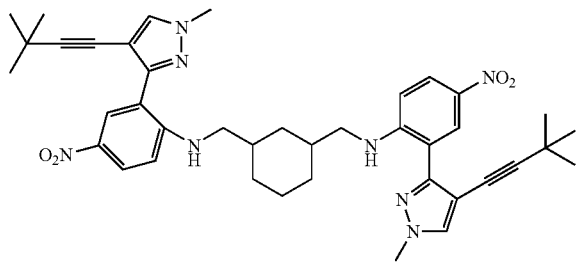

¹H NMR: δ 9.42 (d, J=3 Hz, 2H), 8.62 (t, J=5.5 Hz, 2H), 8.12 (dd, J=9.5, 3.0 Hz, 2H), 7.48 (s, 2H), 6.65 (d, J=9 Hz, 2H), 3.72 (s, 6H), 3.30-3.20 (m, 4H), 3.20-3.10 (m, 2H), 2.14-2.05 (m, 2H), 1.95-1.85 (m, 4H), 1.85-1.70 (m, 2H), 1.38 (s, 18H). LC-MS: (7.64 min, m/z, ES⁺): calcd: 704.38. Found: 705.39.

Example 18

HCV Replicon Luciferase Assay

Day 0, Cell Seeding and Compound Treatment: Huh-Luc-Neo Cells are seeded at 25,000/well in an opaque-walled 96 plate with Growth Medium (DMEM phenol red free+PS+2 mM glutamine; 100 µl/well). The compounds to be tested are added to the experimental wells (10 µl/well at 10× assay concentration) and the cells are then incubated (5% $CO_2$, 37° C.) for 48 h.

Day 2, Reagent Preparation and Luciferase Assay: The Bright-Glo Luciferase Assay Buffer (Promega) is thawed and equilibrated to room temperature prior to use. The lyophilized Bright-Glo Luciferase Assay Substrate is equilibrated to room temperature prior to use. 10 ml of Bright-Glo Luciferase Assay Buffer is transferred to 1 vial of Bright-Glo Luciferase Assay Substrate bottle and mixed by gently with a Vortex. 100 ul of Bright-Glo Luciferase Assay reagent (Bright-Glo Luciferase Assay Buffer+Bright-Glo Luciferase Assay Substrate Mixture) is added to each well. The well contents are mixed for 5 min. on an orbital shaker at room temperature to induce cell lysis and the luminescence is then measured using a luminometer. The data is analyzed and IC50s are determined using GraphPad Prism 4 software. Hits validated in the Replicon Luciferase assay have IC50s<8.0 µM and show <30% inhibition of Cell Viability at a compound concentration of 100 µM (Cell Titer Glow Assay, cell viability assay conditions identical to HCV Replicon Luciferase Assay conditions).

Example 19

HCV Replicon RNA Assay

Day 0, Cell Seeding and Compound Treatment: Huh-Luc-Neo Cells are seeded at 25,000/well in an opaque-walled 96 plate with Growth Medium (DMEM phenol red free+PS+2 mM glutamine; 100 µl/well). The compounds to be tested are added to the experimental wells (10 µl/well at 10× assay concentration) and the cells are then incubated (5% $CO_2$, 37° C.).

Day 1, Media Change and Compound Treatment: 24 hours after the initial compound treatment the cell culture media is aspirated from the wells and fresh Growth Medium is added (DMEM phenol red free+PS+2 mM glutamine; 100 µl/well). The compounds to be tested are then added to the appropriate experimental wells (10 µl/well at 10× assay concentration) and the cells are then incubated (5% $CO_2$, 37° C.) for an additional 24 hrs.

Day 2, RNA Isolation and cDNA Synthesis: The cells are washed with 1× Phosphate Buffered Saline (PBS) once. Cells are then lysed and RNA is isolated in 96 well format using a vacuum manifold and the RNAeasy 96 kit (Qiagen) according to the manufacturer's suggested protocol. cDNA is then synthesized from RNA isolated from each well using the Taqman Reverse Transcription Reagents kit (Applied Biosystems) according to manufacturer's suggested protocol.

Day 3, Quantitative PCR Based Measurement of HCV RNA (Taqman Assay): Quantitative PCR analysis to measure HCV RNA expression from cDNA synthesized on Day 2 is performed using the ABI 9700 HT Sequence Detection System (Applied Biosystems) as previously described (Lohman et al, Science 285, 110-113, 1999). The data is analyzed and IC50s are determined using GraphPad Prism 4 software. Hits validated in the Replicon RNA Assay have IC50s<8.0 µM and show <30% inhibition of Cell Viability at a compound concentration of 50 µM (Cell Titer Glow Assay, cell viability assay conditions identical to HCV Replicon RNA Assay conditions).

Example 20

Cell Titer-Glo Cell Viability Assay (Promega)

Day 0, Cell Seeding and Compound Treatment: Huh-Luc-Neo Cells are seeded at 25,000/well in an opaque-walled 96 plate with Growth Medium (DMEM phenol red free+PS+2 mM glutamine; 100 ul/well). The compounds to be tested for inhibition of cell viability are added to the experimental wells (10 µL/well at 10× assay concentration) and the cells are then incubated (5% $CO_2$, 37° C.) for 48 h.

Day 2, Reagent Preparation and Assay: The CellTiter-Glo Buffer is thawed and equilibrated to room temperature prior to use. The lyophilized CellTiter-Glo Substrate is equilibrated to room temperature prior to use. 10 ml of CellTiter-Glo Buffer is transferred to 1 vial of CellTiter-Glo Substrate and mixed by gently with a Vortex. 100 µl of CellTiter-Glo Assay reagent (CellTiter-Glo Buffer+CellTiter-Glo Substrate Mixture) is added to each well. The well contents are mixed for 5 min. on an orbital shaker at room temperature to induce cell lysis and the luminescence is then measured using a luminometer.

TABLE 5

| Compound | Structure | Luciferase IC50 | Toxicity % Inhibition at 100 µM (1 dose) | TaqMan IC50 | Toxicity % Inhibition at 50 µM (2 doses) |
| --- | --- | --- | --- | --- | --- |
| VQ_23705 | 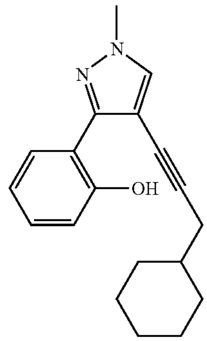 | 6.47 | 26.4 | 1.1 | 14.7 |
| VQ_23708 | 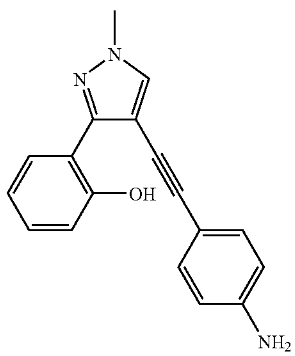 | 0.55 | 63.8 | 0.7 | 21.8 |
| VQ_23307 | 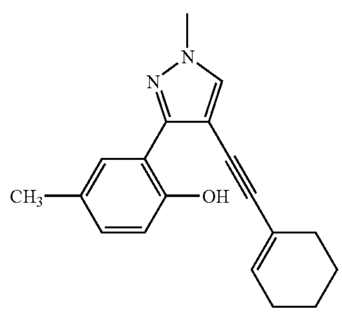 | 7.25 | 44.8 | 8.1 | 14.8 |
| VQ_23317 | 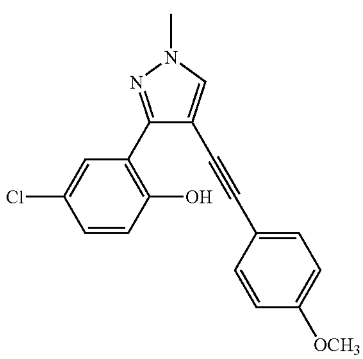 | 4.37 | 10.7 | 2.7 | 2.1 |

TABLE 5-continued

| Compound | Structure | Luciferase IC50 | Toxicity % Inhibition at 100 μM (1 dose) | TaqMan IC50 | Toxicity % Inhibition at 50 μM (2 doses) |
| --- | --- | --- | --- | --- | --- |
| VQ_23374 | 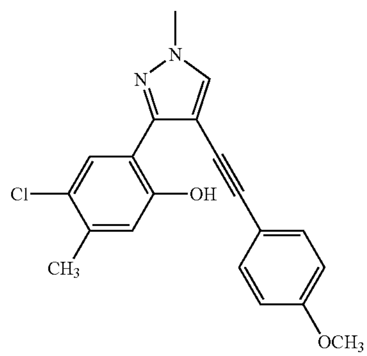 | 3.92 | 19.1 | 5.7 | 13.0 |
| VQ_23714 | 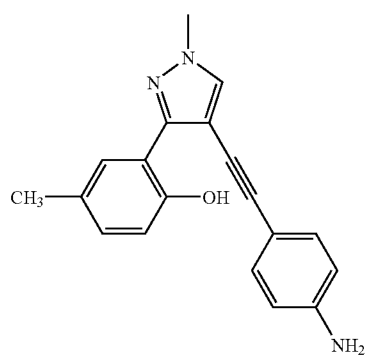 | 1.16 | 31.5 | 0.1 | 33.4 |
| VQ_23720 | 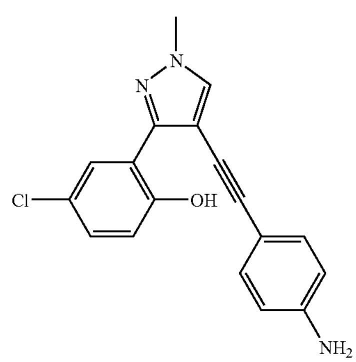 | 1.28 | 49.2 | 0.3 | 32.6 |
| VQ_24691 | 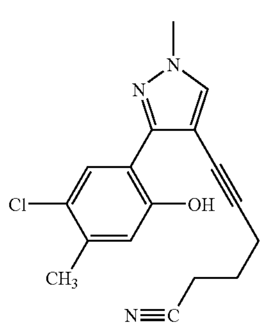 | 5.13 | 21.1 | 0.09 | 28.3 |

TABLE 5-continued

| Compound | Structure | Luciferase IC50 | Toxicity % Inhibition at 100 μM (1 dose) | TaqMan IC50 | Toxicity % Inhibition at 50 μM (2 doses) |
| --- | --- | --- | --- | --- | --- |
| VQ_23310 | 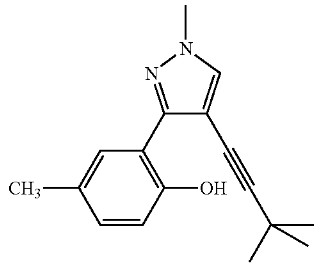 | 7.21 | 33.3 | 1.15 | 7.1 |
| VQ_23382 | 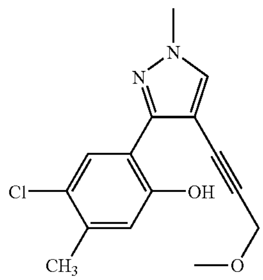 | 14.92 | 18.5 | 3.03 | 8.8 |
| VQ_34145 | 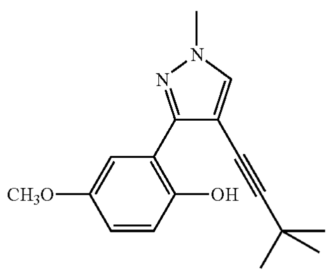 | 1.87 | 19.8 | 0.82 | 13.1 |
| VQ_34298 | 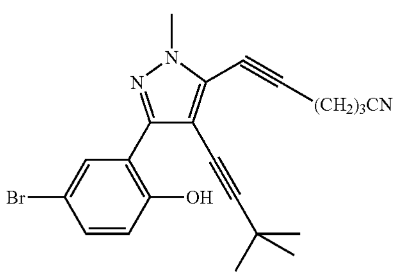 | 5.5 | 18.3 | 3.86 | 23.9 |
| VQ_34394 | 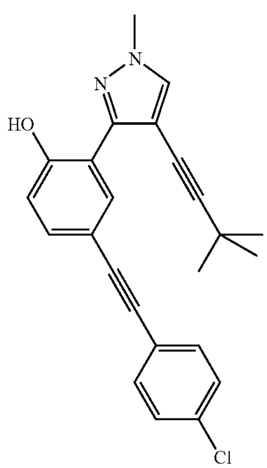 | 4.8 | 31.8 | 1.07 | 24.5 |

TABLE 5-continued
| Compound | Structure | Luciferase IC50 | Toxicity % Inhibition at 100 μM (1 dose) | TaqMan IC50 | Toxicity % Inhibition at 50 μM (2 doses) |
|---|---|---|---|---|---|
| VQ_34395 | 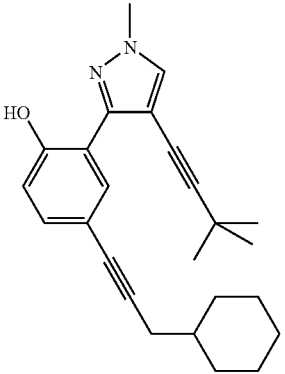 | 3.7 | 45.4 | 0.68 | 23.6 |
| VQ_34432 | 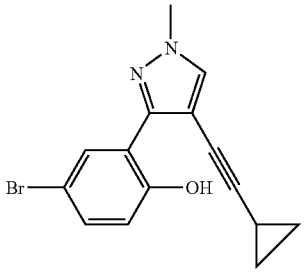 | 11.5 | 45.5 | 0.82 | 8.2 |
| VQ_95538 | 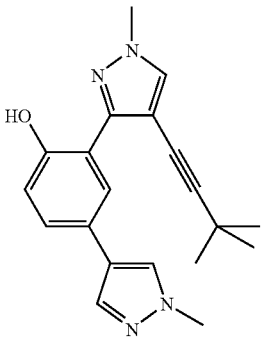 | 9.8 | 24.3 | 1.35 | 6.1 |
| VQ_35543 | 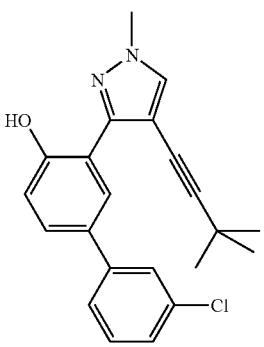 | 10.1 | 25.3 | 2.16 | 8.2 |

TABLE 5-continued

| Compound | Structure | Luciferase IC50 | Toxicity % Inhibition at 100 μM (1 dose) | TaqMan IC50 | Toxicity % Inhibition at 50 μM (2 doses) |
|---|---|---|---|---|---|
| VQ_35556 | 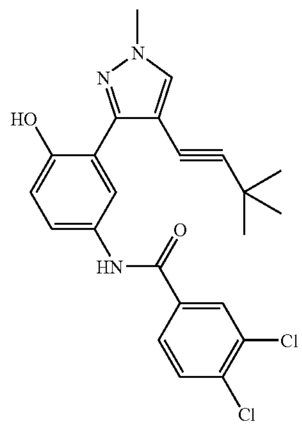 | 9.3 | 28.8 | 0.99 | 13.7 |
| VQ_35559 | 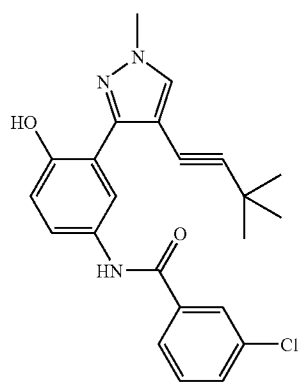 | 9.5 | 24.2 | 1.98 | 15.8 |
| VQ_36658 | 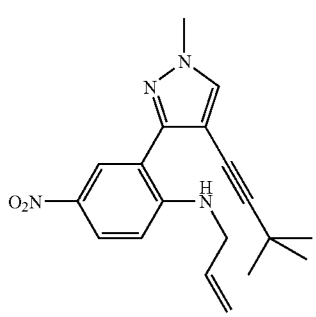 | 0.04 | 21.8 | 0.40 | 38.8 |
| VQ_36659 | 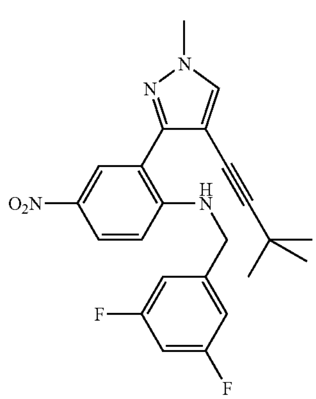 | 0.04 | 13.0 | 0.30 | 21.9 |

TABLE 5-continued

| Compound | Structure | Luciferase IC50 | Toxicity % Inhibition at 100 μM (1 dose) | TaqMan IC50 | Toxicity % Inhibition at 50 μM (2 doses) |
|---|---|---|---|---|---|
| VQ_36660 | 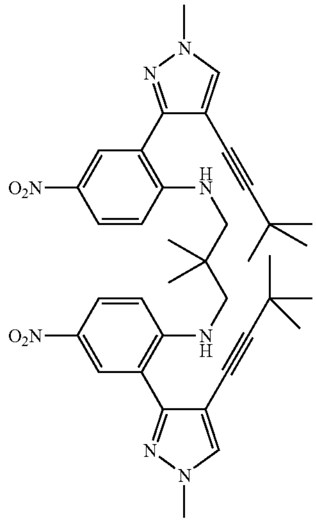 | 10.36 | 15.3 | 0.59 | 15.8 |
| VQ_36661 | 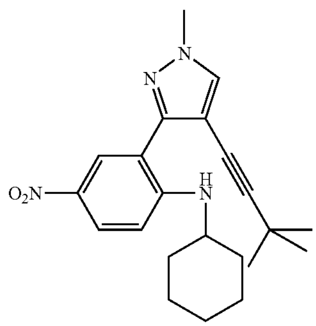 | 0.63 | 9.5 | 0.55 | 14.4 |
| VQ_36663 | 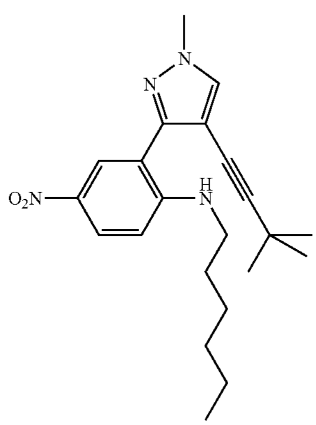 | 0.00 | 15.5 | 0.75 | 23.8 |

TABLE 5-continued

| Compound | Structure | Luciferase IC50 | Toxicity % Inhibition at 100 μM (1 dose) | TaqMan IC50 | Toxicity % Inhibition at 50 μM (2 doses) |
|---|---|---|---|---|---|
| VQ_36665 | 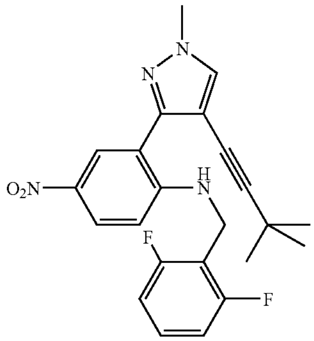 | 0.03 | 12.8 | 0.72 | 25.6 |
| VQ_36666 | 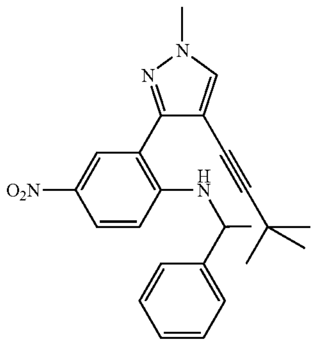 | 0.35 | 12.9 | 0.38 | 19.0 |
| VQ_36669 | 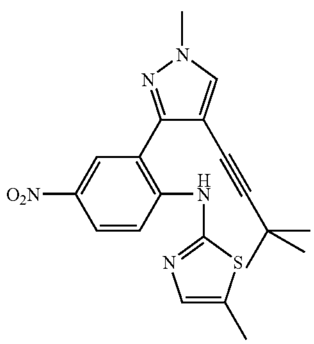 | 0.01 | 23.2 | 0.90 | 26.7 |
| VQ_36673 | 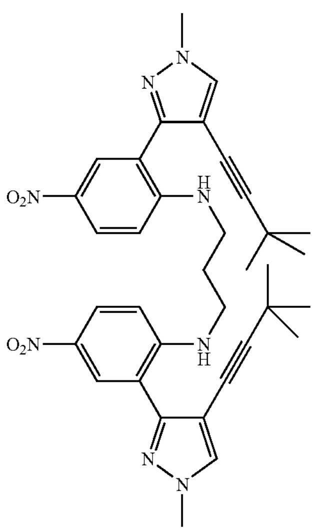 | 2.09 | 15.9 | 0.42 | 19.7 |

TABLE 5-continued

| Compound | Structure | Luciferase IC50 | Toxicity % Inhibition at 100 μM (1 dose) | TaqMan IC50 | Toxicity % Inhibition at 50 μM (2 doses) |
| --- | --- | --- | --- | --- | --- |
| VQ_36649 | 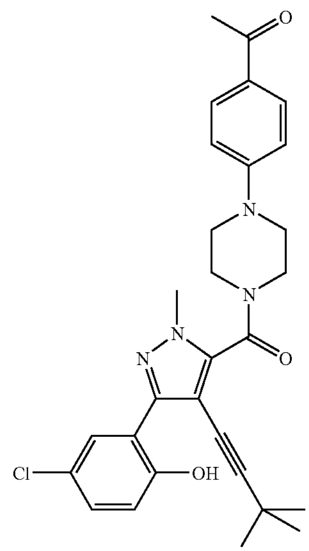 | 9.70 | 7.3 | 0.40 | 12.1 |
| VQ_36877 | 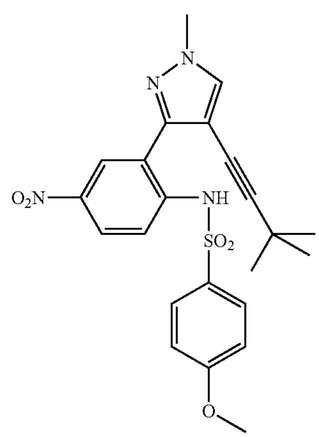 | | | 0.20 | 10.9 |
| VQ_36885 | 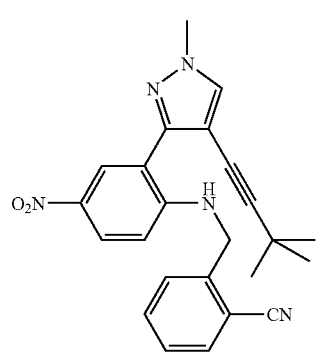 | | | 0.03 | 35.7 |

TABLE 5-continued

| Compound | Structure | Luciferase IC50 | Toxicity % Inhibition at 100 µM (1 dose) | TaqMan IC50 | Toxicity % Inhibition at 50 µM (2 doses) |
|---|---|---|---|---|---|
| VQ_36886 | 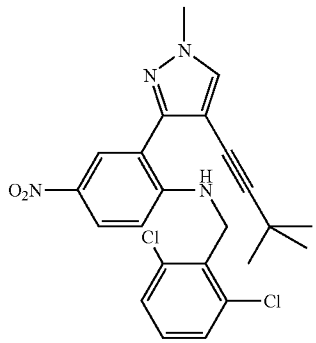 | 0.19 | 12.6 | | |
| VQ_36887 | 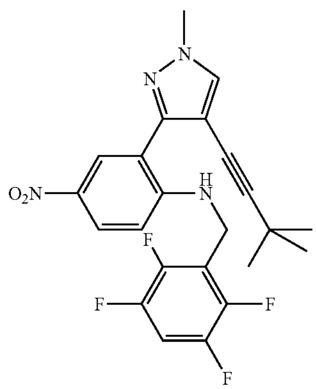 | 0.06 | 18.7 | | |
| VQ_36893 | 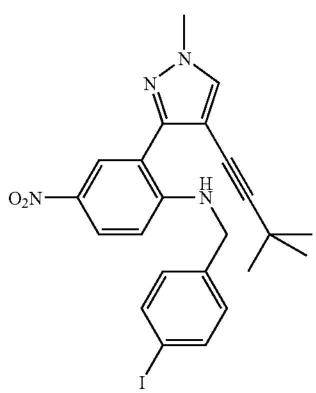 | 0.09 | 16.6 | | |
| VQ_36894 | 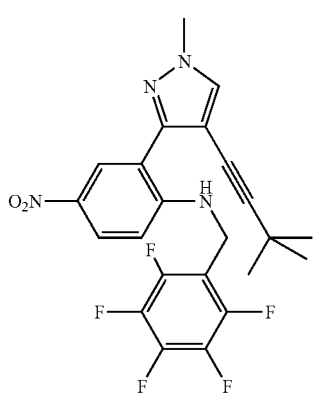 | 0.12 | 12.5 | | |

TABLE 5-continued
| Compound | Structure | Luciferase IC50 | Toxicity % Inhibition at 100 μM (1 dose) | TaqMan IC50 | Toxicity % Inhibition at 50 μM (2 doses) |
| --- | --- | --- | --- | --- | --- |
| VQ_36895 | 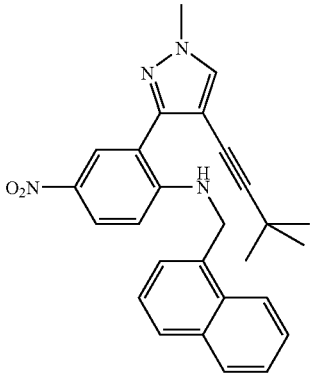 | 0.10 | 10.4 | | |
| VQ_36905 | 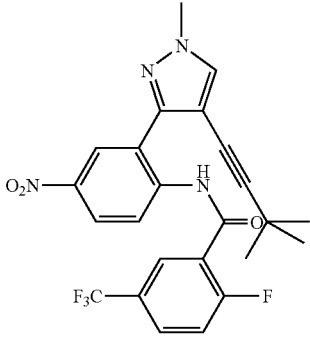 | 1.63 | 10.9 | | |
| VQ_36906 | 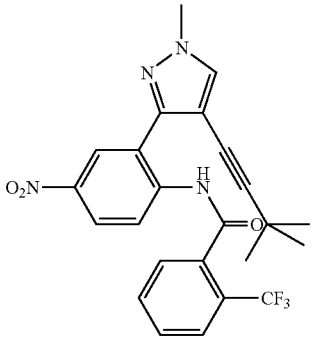 | 2.69 | 14.0 | | |
| VQ_36907 | 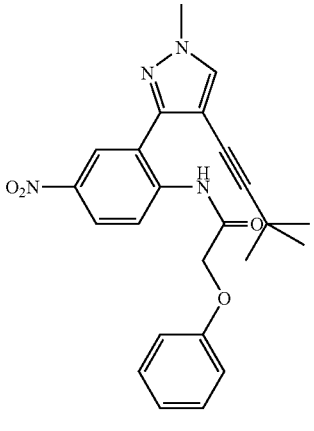 | 0.20 | 34.7 | | |

TABLE 5-continued

| Compound | Structure | Luciferase IC50 | Toxicity % Inhibition at 100 μM (1 dose) | TaqMan IC50 | Toxicity % Inhibition at 50 μM (2 doses) |
|---|---|---|---|---|---|
| VQ_36908 | 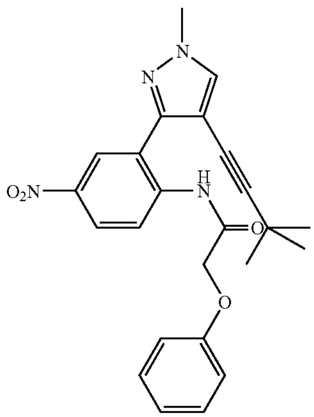 | 1.72 | 22.7 | | |
| VQ_23322 | 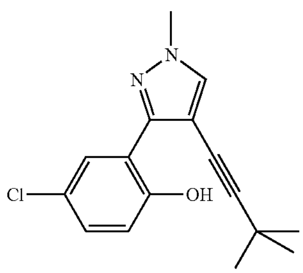 | 2.00 | 21.5 | 2.47 | 1.5 |
| VQ_23324 | 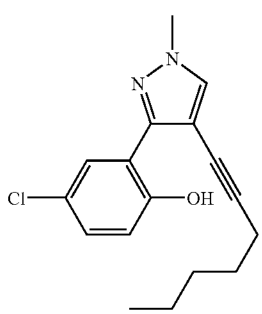 | 5.51 | 39.8 | 0.03 | 8.8 |
| VQ_23382 | 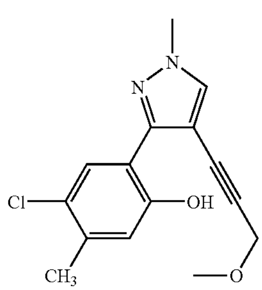 | 6.47 | 16.2 | 2.26 | −1.6 |

TABLE 5-continued

| Compound | Structure | Luciferase IC50 | Toxicity % Inhibition at 100 μM (1 dose) | TaqMan IC50 | Toxicity % Inhibition at 50 μM (2 doses) |
|---|---|---|---|---|---|
| VQ_30716 | 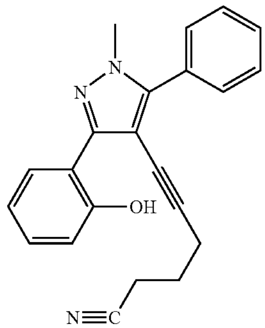 | 3.96 | 13.7 | 0.11 | 6.8 |
| VQ_33518 | 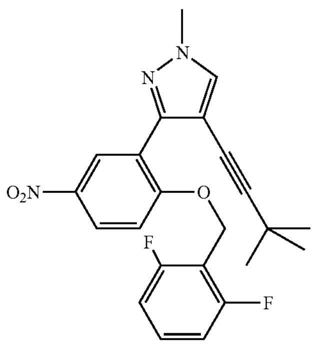 | 1.85 | 40.4 | 0.42 | 22.8 |
| VQ_34072 | 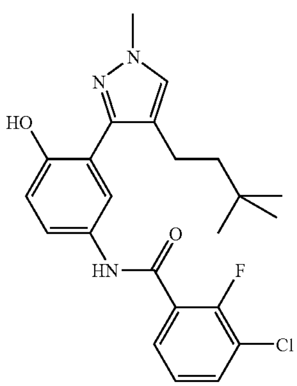 | 2.87 | 4.2 | 1.09 | 6.2 |

What is claimed is:

1. The compound having the formula V:

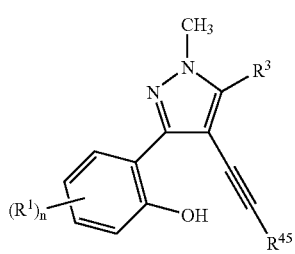

wherein:

each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3R^{11}$, —SO$_2$N($R^{12}$)($R^{13}$), -alkyl-O—$R^{11}$, cycloalkyl, cycloalkenyl, halo, aryl or heteroaryl;

additionally or alternatively two $R^1$ substituents on adjacent ring atoms may be combined to form a fused 5 or 6-membered ring, wherein the fused 5- or 6-membered ring may contain from 0 to 3 ring heteroatoms;

each $R^{11}$ is independently selected from H, alkyl, alkyl-O-alkyl, alkyl-O-aryl, alkenyl, alkynyl, cycloalkyl, cycloalkenyl, aralkyl, aryl or heteroaryl;

each $R^{12}$ and $R^{13}$ is independently selected from H, alkyl, cycloalkyl, cycloalkenyl, alkyl-O-alkyl, alkyl-O-aryl, alkenyl, alkynyl, aralkyl, aryl or heteroaryl; or $R^{12}$ and $R^{13}$ may be taken together with the nitrogen to which they are attached to form a 5- to 7-membered ring which may optionally contain a further heteroatom;

n is 0 to 4;

$R^3$ is H;

$R^{45}$ is selected from the group consisting of H, alkyl, -alkyl-O-alkyl, -alkyl-O-aryl, aryl, aralkyl, cycloalkyl, cycloalkenyl, and $-(CH_2)_a-R^{42}$;

$R^{42}$ is selected from the group consisting of $-N(R^{421})C(O)R^{421}$, $-N(R^{421})SO_2R^{421}$, $-OR^{421}$, $-SR^{421}$, $-C(O)R^{421}$, $-C(O)OR^{421}$ $-C(O)N(R^{422})(R^{423})$, $-OC(O)R^{421}$, $-OC(O)N(R^{422})(R^{423})$, CN, CF$_3$, NO$_2$, SO$_2$, $-SOR^{421}$, $-SO_3R^{421}$, $-SO_2N(R^{422})(R^{423})$, -alkyl-O-alkyl, -alkyl-O-aryl, halo, cycloalkyl, cycloalkenyl, aryl and heteroaryl; or $R^{42}$ is

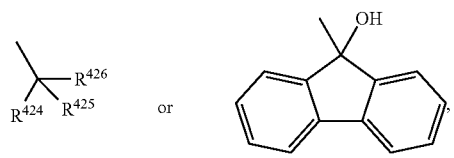

each $R^{421}$ is independently selected from H, alkyl, cycloalkyl, alkenyl, alkynyl, aralkyl, aryl or heteroaryl;

each $R^{422}$ and $R^{423}$ is independently selected from H, alkyl, cycloalkyl, alkenyl, alkynyl, aralkyl, aryl or heteroaryl; or $R^{422}$ and $R^{423}$ may be taken together with the nitrogen to which they are attached to form a 5- to 7-membered ring which may optionally contain a further heteroatom;

each $R^{424}$ is independently selected from H, OH, alkyl, cycloalkyl, alkenyl, alkynyl, aralkyl, aryl or heteroaryl;

each $R^{425}$ and $R^{426}$ is independently selected from H, alkyl, cycloalkyl, alkenyl, alkynyl, aralkyl, aryl or heteroaryl; or $R^{425}$ and $R^{426}$ may be taken together with the carbon to which they are attached to form a 5- to 7-membered ring which may optionally contain a further heteroatom;

a is 1 to 6;

or a pharmaceutically acceptable salt thereof.

2. The compound of claim 1 having the formula

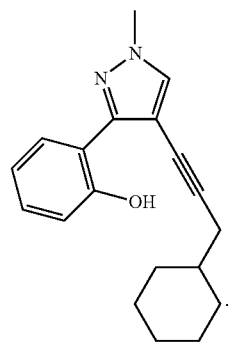

3. The compound of claim 1 having the formula

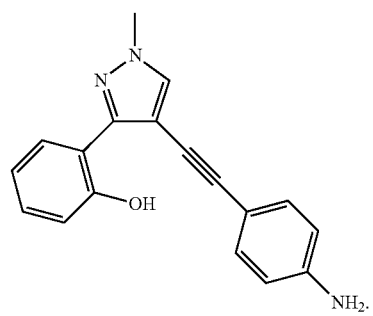

4. The compound of claim 1 having the formula

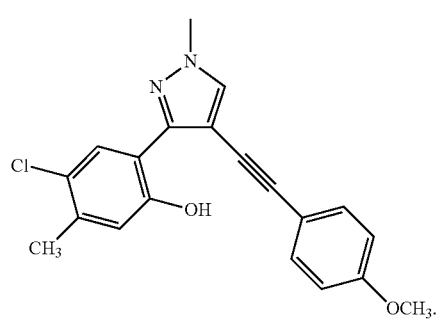

5. The compound of claim 1 having the formula

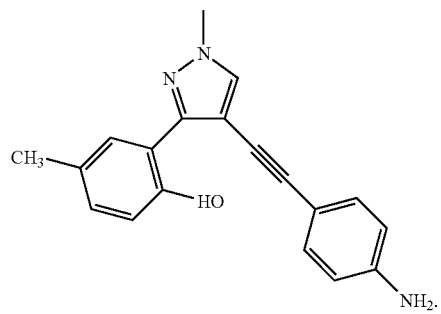

6. The compound of claim 1 having the formula

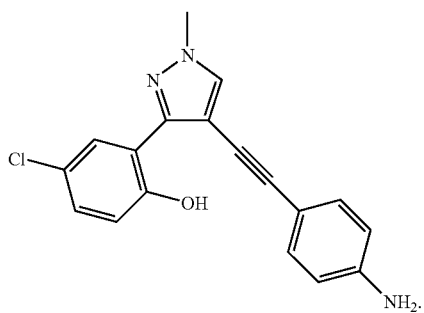

7. The compound of claim 1 having the formula

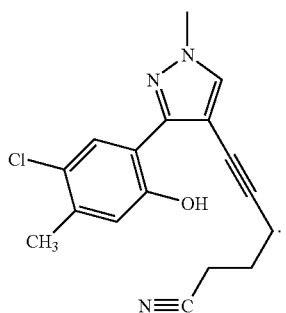

8. The compound of claim 1 having the formula

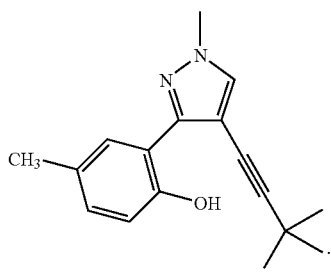

9. The compound of claim 1 having the formula

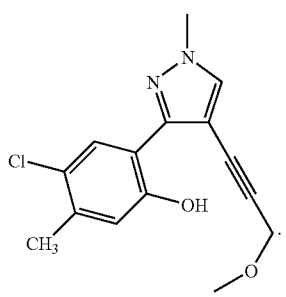

10. The compound of claim 1 having the formula

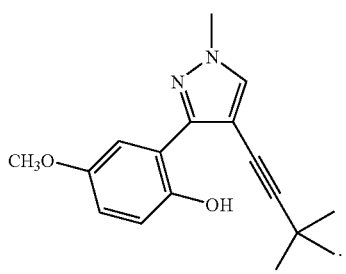

11. The compound of claim 1 having the formula

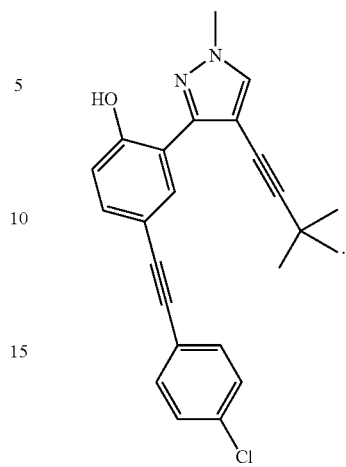

12. The compound of claim 1 having the formula

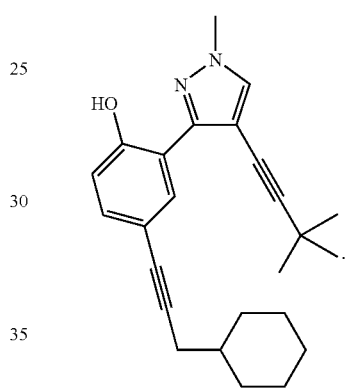

13. The compound of claim 1 having the formula

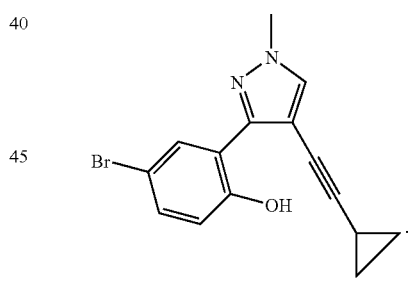

14. The compound of claim 1 having the formula

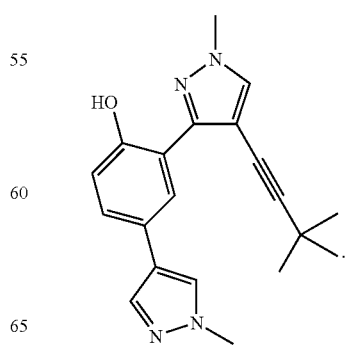

15. The compound of claim 1 having the formula

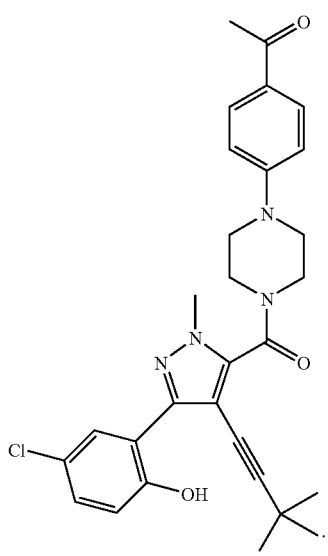

16. A pharmaceutical composition for the treatment of HCV infection, comprising a therapeutically effective amount of a compound of according to claim 1 in a pharmaceutically acceptable carrier.

17. The pharmaceutical composition of claim 16, further comprising a second antiviral agent.

18. The pharmaceutical composition of claim 17, wherein the second anti-viral agent is selected from the group consisting of an interferon, ribavirin, an HCV protease inhibitor, an HCV polymerase inhibitor, an HCV IRES inhibitor, an HCV Helicase, and an HCV ATPase inhibitor.

19. The pharmaceutical composition of claim 18, wherein the second agent is an interferon.

20. The pharmaceutical composition of claim 19, wherein the second agent is α-interferon.

* * * * *